United States Patent
Palese et al.

(10) Patent No.: US 6,890,710 B1
(45) Date of Patent: May 10, 2005

(54) IDENTIFICATION AND USE OF ANTIVIRAL COMPOUNDS THAT INHIBIT INTERACTION OF HOST CELL PROTEINS AND VIRAL PROTEINS REQUIRED FOR VIRAL REPLICATION

(75) Inventors: Peter Palese, Leoma, NJ (US); Robert O'Neill, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 0 days.

(21) Appl. No.: 08/444,994

(22) Filed: May 19, 1995

Related U.S. Application Data

(63) Continuation-in-part of application No. 08/246,583, filed on May 20, 1994, now Pat. No. 5,750,394.

(51) Int. Cl.[7] ............................................... C12Q 1/70
(52) U.S. Cl. ........................ 435/5; 435/7.1; 424/206.1
(58) Field of Search .................... 435/5, 7.1; 424/206.1

(56) References Cited

U.S. PATENT DOCUMENTS

| | | | | |
|---|---|---|---|---|
| 5,110,906 A | * | 5/1992 | Maddon et al. | 530/350 |
| 5,738,985 A | * | 4/1998 | Miles et al. | 435/5 |
| 5,744,343 A | * | 4/1998 | Draetta et al. | 435/193 |

OTHER PUBLICATIONS

Stedman's Medical Dictionary, 26th Ed. Baltimore: Williams & Wilkins. 1995, pp. 1508–1510, 8/95.*
Martin, C.R. (1995) Dictionary of Endocrinology and Related Biomedical Sciences. New York: Oxford University Press. p. 623, 9/95.*
Merriam–Webster's Medical Desk Dictionary. Springfield, MA: Merriam–Webster Inc. 1993, p. 605, 7/94.*
Lawrence, E. (1989) Henderson's Dictionary of Biological Terms, 10th Ed. New York: John Wiley & Sons. p. 460, 10/90.*
Kalpana et al., 1994, "Binding and Stimulation of HIV–1 Intergrase a Human Homolog of Yeast Transcription Factor SNF5", *Science* 266:2002–2006.
Luban et al., 1993, "Human Immunodeficiency Virus Type 1 Gag Protein Binds CyclophiliinsA and B", *Cell* 73:1067–1078.
Baez et al., 1981, "Nucleotide sequence of the influenza A/duck/Alberta/60/76 virus NS RNA: Conservation of the NS1/NS2 overlapping gene structure in a divergent influenza virus RNA segment", *Virol.* 113:397–402.

(Continued)

*Primary Examiner*—James Housel
*Assistant Examiner*—Jeffrey S. Parkin
(74) *Attorney, Agent, or Firm*—Jones Day

(57) ABSTRACT

The present invention relates to the identification of host cell proteins that interact with viral proteins required for virus replication, and high throughput assays to identify compounds that interfere with the specific interaction between the viral and host cell protein. Interfering compounds that inhibit viral replication can be used therapeutically to treat viral infection.

Figure 1A:
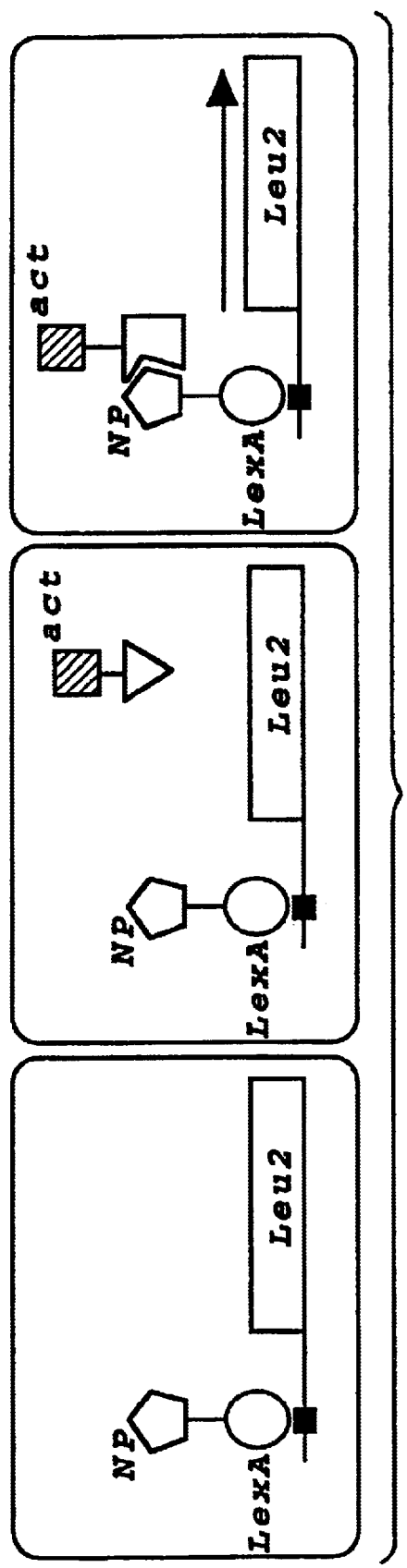

The invention is based, in part, on the Applicants' discovery of novel interactions between proteins of the influenza virus and a human host cell proteins. One of these host cell proteins, referred to herein as NPI-1, interacts with influenza virus protein NP, and may be an accessory protein required for replication of influenza virus. Another of these host cell proteins, referred to herein as NS1I-1, interacts with influenza virus protein $NS_1$. Compounds that interfere with the binding of the host cell and viral proteins, and inhibit viral replication can be useful for treating viral infection in vivo.

31 Claims, 32 Drawing Sheets

OTHER PUBLICATIONS

Baudin et al., 1994, "Structure of influenza virus RNP. 1. Influenza virus nucleoprotein melts secondary structure in panhandle RNA and exposes the bases to the solvent", *EMBO J.* 13:3158–3165.

Barik & Banerjee, 1992, "Sequential phosphorylation of the phosphoprotein of vesicular stomatitis virus by cellular and viral protein kinases is essential for transcription activation", *J. of Virol.* 66:1109–1118.

Barik & Banerjee, 1992, "Phosphorylation by cellular casein kinase II is essential for transcriptional activity of vesicular stomatitis virus phosphoprotein P", *PNAS USA* 89:6570–6574.

Bean, 1984. "Correlation of influenza A virus nucleoprotein genes with host species", *Virol.* 133:438–442.

Beaton & Krug, 1986, "Transcription antitermination during influenza viral template RNA synthesis requires the nucleocapsid protein and the absence of a 5' capped end", *PNAS USA* 83:6282–6286.

Belanger et al., "Genetic and physical interactions between Srp 1p and nuclear pore complex proteins Nup1p and Nup2p", *J. of Cell Biol*, 126:619–630.

Buckler–White & Murphy, 1986, "Nucleotide sequence analysis of the nucleoproteins gene of an avian and a human influenza virus strain identifies two classes of nucleoproteins", *Virol.* 155:345–355.

Buonagurio et al., 1986, "Evolution of human influenza A viruses over 50 years: Rapid, uniform rate of change in NS gene", *Science* 232:980–982.

Chelsky et al., 1989. "Sequence requirements for synthetic peptide–mediated translocation to the nucleus", *Mol. Cell. Biol.* 9:2487–2492.

Chen et al., 1993, "Site–specific mutagenesis of Drosophila alcohol dehydrogenase: Evidence for involvement of tyrosine–0 152 and lysine– 156 in catalysis". *Biochem.* 32:3342–3346.

Chien et al., 1991, "The two–hybrid system: A method to identify and clone genes for proteins that interact with a protein of interest", *PNAS USA* 88:9578–9582.

Cortes et al., 1994, "RAG 1 interacts with the repeated amino acid motif of the human homologue of the yeast protein SRP1" *PNAS USA* 91:7633–7637.

Cuomo et al., 1994, "Rch1, a protein that specifically interacts with the RAG–1 recombination–activating protein", *PNAS USA* 91:6156–6160.

Cuomo et al., 1994, Mtg abstr. F015, keystone Symp. on Recombination.

Dalton & Treisman, 1992, "Characterization of SAP–1, a protein recruited by serum response factor to the c–fos serum response element", *Cell* 68:597–612.

de Hopp & Ab, 1992, "Import of proteins into peroxisomes and other microbodies", *Biochem. J.* 286:657–669.

Durfee et al., 1993, "The retinoblastoma protein associates with the protein phosphatase type 1 catalytic subunit", *Genes Dev.* 7:555–569.

Enami et al., 1990, "Introduction of site–specific mutations into the genome of influenza virus", *PNAS USA* 87:3802–3805.

Fortes et al., 1994, "Influenza virus NS1 protein inhibits pre–mRNA splicing and blocks mRNA nucleocytoplasmic transport", *EMBO J.* 13:704–712.

Gammelin et al., 1989, "Two subtypes of nucleoproteins (NP) of influenza A viruses", *Virol.* 170:71–80.

Ge & Roeder, 1994, "Purification, cloning, and characterization of a human coactivator, PC4, that mediates transcriptional activation of class II genes", *Cell* 78:513–523.

Ge et al., 1994, "Phosphorylation negatively regulates the function of coactivator PC4", *PNAS USA* 91:12691–12695.

Greenspan et al., 1988, "Two nuclear location signals in the influenza virus NS1 nonstructural protein", *J. Virol.* 62:3020–3026.

Gyuris et al., 1993, "Cdi1, a human G1 and S phase protein phosphatase that associates with Cdk2", *Cell* 75:791–803.

Hall et al., 1984, "Targeting of *E. coli* β–Galactosidase to the nucleus in yeast", *Cell* 36:1057–1065.

Hatada et al., 1990, "Analysis of influenza A virus temperature–sensitive mutants with mutations in RNA segment 8", *J. Gen. Virol.* 71:1283–1292.

Hatada & Fukada. 1992, "Binding of influenza A virus NS1 protein to dsRNA in vitro", *J. Gen. Virol.* 73:3325–3329.

Hatada et al., 1992, "Specific binding of influenza A virus NS1 protein to the virus minus sense RNA in vitro", *J. Gen. Virol.* 73:17–25.

Hentze, 1994, "Enzymes as RNA–binding proteins: A role for (di)nucleotide–binding domains?". *TIBS* 19:101–103.

Honda et al., 1988, "RNA polymerase of influenza virus: Role of NP in RNA chain elongation", *J. Biochem.* 104:1021–1026.

Huang et al., 1990, "Determination of influenza virus proteins required for genome replication", *J. of Virol.* 64:5669–5673.

Jackson et al., 1982, "Influenza virus RNA is synthesized at fixed sites in the nucleus", *Nature* 296:366–368.

Joklik et al. (eds), 1992, "Antiviral chemotherapy, interferon, and vaccines", *Zinsser Microbiology* Appleton & Lange, Norwalk, Conn. Chap. 58, pp. 854–861.

Koennecke et al., 1981, "Isolation and properties of a temperature–sensitive mutant (ts 412) of an influenza A virus recombinant with a ts lesion in the gene coding for the nonstructural protein", *Virol.* 110:16–25.

Lahiri & Thomas, 1986, "A cDNA clone of the hnRNP C proteins and its homology with the single–stranded DNA binding protein UP2", *Nucl. Acid Res.* 14:4077–4094.

Leenders et al., 1994, "Molecular cloning and amino acid sequence of the porcine 17β–estradiol dehydrogenase", *Eur. J. Biochem.* 222:221–227.

Lu et al., 1994, "The influenza virus NS1 protein: A novel inhibitor of pre–mRNA splicing", *Genes Dev.* 8:1817–1828.

Ludwig et al., 1991, "Phylogenetic relationship of the nonstructural (NS) genes of influenza A viruses", *Virol.* 183:566–577.

McCrea et al., 1991, "A homolog of the armadillo protein in Drosphila (Plakoglobin) associated with E–Cadherin", *Science* 254:1359–1361.

Nakada et al., 1984, "Complete nucleotide sequence of the influenza C/California/78 virus nucleoprotein gene", *Virus Res.* 1:433–441.

Norton et al., 1987, "Infectious influenza A and B virus variants with long carboxyl terminal deletions in the NS1 polypeptides", *Virol.* 156:204–213.

O'Neill & Palese, 1994, "Cis–acting signals and trans–acting factors involved in influenza virus RNA synthesis", *Infections Agents and Disease* 3:77–84.

O'Neill & Palese, 1995, "NPI–1, the human homolog of SRP–1, interacts with influenza virus nucleoprotein", *Virol.* 206:116–125.

O'Neill & Palese, 1995, "Cis–acting signals and trans–acting factors involved in influenza virus RNA synthesis", *Chem. Abstracts* 122:198, abstr. 124020P.

Parvin et al., 1989. "Promoter analysis of influenza virus RNA polymerase", *J. Virol.* 63:5142–5152.

Peelman et al., 1995, "The BAT1 gene in the MHC encodes and evolutionarily conserved putative nuclear RNA helicase of the DEAD family". *Genomics* 26:210–218.

Peifer et al., 1994, "A repeating amino acid motif shared by proteins with diverse cellular roles", *Cell* 76:789–791.

Persson et al., 1991, "Characteristics of short chain alcohol dehydrogenases and related enzymes", *Eur. J. Biochem.* 200:537–543.

Qiu & Krug, 1994, "The influenza virus NS1 protein is a poly(A)–binding protein that inhibits nuclear export of mRNAs containing poly(A)", *J. Virol.* 68 2425–2432.

Riggleman et al., 1989, "Molecular analysis of the armadillo locus: Uniformly distributed transcripts and a protein with novel internal repeats are associated with a Drosophila segment polarity gene", *Genes & Dev.* 3:96–113.

Scholtissek et al., 1978, "Host range recombinants of fowl plague (Influenza A) virus", *Virol.* 91:79 85.

Scholtissek et al., 1985, "The nucleoprotein as a possible major factor in determining host specificity of influenza H3N2 viruses", *Virol.* 147:287–294.

Shapiro & Krug, 1988, "Influenza virus RNA replication in vitro: Synthesis of viral template RNAs and virion RNAs in the absence of an added primer", *J. of Virol.* 62:2285–2290.

Vojtek et al., 1993, "Mammalian Ras interacts directly with the Serine/Threonine kinase Raf", *Cell* 74:205–214.

Wolstenholme et al., 1980, "Influenza virus–specific RNA and protein synthesis in cells infected with temperature–sensitive mutants defective in the genome segment encoding nonstructural proteins", *J. Virol.* 35:1–7.

Yano et al., 1992, "Cloning and characterization of SRP1, a suppressor of temperature–sensitive RNA polymerase I mutations, in *Saccharomyces cerevisiae*", *Mol. Cell. Biol* 12:5640–5651.

Yano et al., 1994, "Yeast Srp1p has homology to armadillo/plakoglobin/β–catenin and participates in apparently multiple nuclear functions including the maintenance of the nucleolar structure", *PNAS USA* 91:6880–6884.

Zervos et al., 1993, "Mxi1, a protein that specifically interacts with Max to bind Myc–Max recognition sites", *Cell* 72:222–232.

* cited by examiner

```
              20                    40                    60
CTAACTTCAG CGGTGGCACC GGGATCGGTT GCCTTGAGCC CCACCCCAGG
                                              M  T  T  P  G>

80                   100                   120
AAAAGAGAAC TTTCGCCTGA AAAGTTACAA GAACAAATCT CTGAATCCCG ATGAGATGCG
 K  E  N  F  R  L  K  S  Y  K  N  K  S  L  N  P  D  E  M  R>

140                   160                   180
CAGGAGGAGG GAGGAAGAAG GACTGCAGTT ACGAAAGCAG AAAAGAGAAG AGCAGTTATT
 R  R  R  E  E  E  G  L  Q  L  R  K  Q  K  R  E  E  Q  L  F>

200                   220                   240
CAAGCGGAGA AATGTTGCTA CAGCAGAAGA AGAAACAGAA GAAGAAGTTA TGTCAGATGG
 K  R  R  N  V  A  T  A  E  E  E  T  E  E  E  V  M  S  D  G>

260                   280                   300
AGGCTTTCAT GAGGCTCAGA TTAGTAACAT GGAGATGGCA CCAGGTGGTG TCATCACTTC
 G  F  H  E  A  Q  I  S  N  M  E  M  A  P  G  G  V  I  T  S>

320                   340                   360
TGACATGATT GAGATGATAT TTTCCAAAAG CCCAGAGCAA CAGCTTTCAG CAACACAGAA
 D  M  I  E  M  I  F  S  K  S  P  E  Q  Q  L  S  A  T  Q  K>
```

FIG. 2A

```
                         380                           400                          420
ATTCAGGAAG CTGCTTTCAA AAGAACCTAA CCCTCCTATT GATGAAGTTA TCAGCACACC
 F  R  K   L  L  S     K  E  P  N     P  P  I      D  E  V     I  S  T  P>

440                           460                          480
AGGAGTAGTG GCCAGGTTTG TGGAGTTCCT CAAACGAAAA GAGAATTGTT CACTGCAGTT
 G  V  V   A  R  F     V  E  F  L     Q  T  K  R  K     E  N  C     S  L  Q  F>

500                           520                          540
TGAATCAGCT TGGGTACTGA CAAATATTGC TTCAGGAAAT TCTCTTCAGA CCCGAATTGT
 E  S  A   W  V  L     T  N  I  A     S  G  N     S  L  Q     T  R  I  V>

560                           580                          600
GATTCAGGCA AGAGCTGTGC CCATCTTCAT AGAGTTGCTC AGCTCAGAGT TTGAAGATGT
 I  Q  A   R  A  V     P  I  F  I     E  L  L     S  S  E     F  E  D  V>

620                           640                          660
CCAGGAACAG GCAGTCTGGG CTCTTGGCAA CATTGCTGGA GATAGTACCA TGTGCAGGA
 Q  E  Q   A  V  W     A  L  G  N     I  A  G     D  S  T     M  C  R  D>

680                           700                          720
CTATGTCTTA GACTGCAATA TCCTTCCCCC TCTTTTGCAG TTATTTCAA AGCAAAACCG
 Y  V  L   D  C  N     I  L  P  P     L  L  Q     L  F  S     K  Q  N  R>
```

FIG. 2B

```
                                  740                              760                              780
CCTGACCATG ACCCGGAATG CAGTATGGGC TTTGTCTAAT CTCTGTAGAG GGAAAAGTCC
 L    T    M    T    R    N    A    V    W    A    L    S    N    L    C    R    G    K    S    P>

800                              820                              840
ACCTCCAGAA TTTGCAAAGG TTTCTCCATG TCTGAATGTG CTTTCCTGGT TGCTGTTTGT
 P    P    E    F    A    K    V    S    P    C    L    N    V    L    S    W    L    L    F    V>

860                              880                              900
CAGTGACACT GATGTACTGG CTGATGCCTG CTGGGCCCTC TCATATCTAT CAGATGGACC
 S    D    T    D    V    L    A    D    A    C    W    A    L    S    Y    L    S    D    G    P>

920                              940                              960
CAATGATAAA ATTCAAGCGG TCATCGATGC GGGAGTATGT AGGAGACTTG TGGAACTGCT
 N    D    K    I    Q    A    V    I    D    A    G    V    C    R    R    L    V    E    L    L>

980                              1000                             1020
GATGCATAAT GATTATAAAG TGGTTTCTCC TGCTTTGCGA GCTGTGGGAA ACATTGTCAC
 M    H    N    D    Y    K    V    V    S    P    A    L    R    A    V    G    N    I    V    T>

1040                             1060                             1080
AGGGGATGAT ATTCAGACAC AGGTAATTCT GAATTGCTCA GCTCTGCAGA GTTTATTGCA
 G    D    D    I    Q    T    Q    V    I    L    N    C    S    A    L    Q    S    L    L    H>

FIG. 2C
```

```
                                              1100                          1120                          1140
TTGCTGAGT AGCCCAAAGG AATCTATCAA AAAGGAAGCA TGTTGGACGA TATCTAATAT
 L  L  S    S  P  K    E  S  I  K   K  E  A   C  W  T   I  S  N  I>

1160                          1180                          1200
TACAGCTGGA AATAGGGCAC AGATCCAGAC TGTGATAGAT GCCAACATTT TCCCAGCCCT
 T  A  G    N  R  A    Q  I  Q  T   V  I  D   A  N  I   F  P  A  L>

1220                          1240                          1260
CATTAGTATT TTACAAACTG CTGAATTTCG GACAAGAAAA GAAGCAGCTT GGGCCATCAC
 I  S  I    L  Q  T    A  E  F  R   T  R  K   E  A  A   W  A  I  T>

1280                          1300                          1320
AAATGCAACT TCTGGAGGAT CAGCTGAACA GATCAAGTAC CTAGTAGAAC TGGGTTGTAT
 N  A  T    S  G  G    S  A  E  Q   I  K  Y   L  V  E   L  G  C  I>

1340                          1360                          1380
CAAGCCGCTC TGTGATCTCC TCACGGTCAT GGACTCTAAG ATTGTACAGG TTGCCCTAAA
 K  P  L    C  D  L    L  T  V  M   D  S  K   I  V  Q   V  A  L  N>

1400                          1420                          1440
TGGCTTGGAA AATATCCTGA GGCTTGGAGA ACAGGAAGCC AAAGGAACG GCACTGGCAT
 G  L  E    N  I  L    R  L  G  E   Q  E  A   K  R  N   G  T  G  I>

FIG. 2D
```

```
                    1460                                     1480                                     1500
TAACCCTTAC TGTGCTTTGA TTGAAGAAGC TTATGGTCTG GATAAAATTG AGTTCTTACA
 N  P  Y    C  A  L    I  E  E  A    Y  G  L    D  K  I    E  F  L  Q>
                    1520                                     1540                                     1560
GAGTCATGAA AACCAGGAGA TCTACCAAAA GGCCTTTGAT CTTATTGAGC ATTACTTCGG
 S  H  E  N    Q  E    I  Y  Q  K    A  F  D    L  I  E    H  Y  F  G>
                    1580                                     1600                                     1620
GACCGAAGAT GAAGACAGCA GCATTGCACC CCAGGTTGAC CTTAACCAGC AGCAGTACAT
 T  E  D  E  D  S    S  I  A  P    Q  V  D    L  N  Q    Q  Q  Y  I>
                    1640                                     1660                                     1680
CTTCCAACAG TGTGAGGCTC CTATGGAAGG TTTCCAGCTT TGAAGCAATA CTCTGCTTTC
 F  Q  Q    C  E  A    P  M  E  G    F  Q  L>
                    1700                                     1720                                     1740
ACGTACCTGT GCTCAGACCA GGCTACCCAG TCGAGTCCTC TTGTGGAGCC CACAGTCCTC
                    1760                                     1780                                     1800
ATGGAGCTAA CTTCTCAAAT GTTTTCCATA ATACTGTTTG CGCTCATTTG CTTGCCTTGC
                    1820                                     1840                                     1860
GCACCTGCTC TCTTACACAC ATCTGGAAAA CCTCCGGCTC TCTGTGGTGG GATACCCTTC
```

FIG. 2E

```
                1880                      1900                      1920
TAATAAAAGG GTAACCAGAA CGGCCCCACTC TCTTTTACGG AAAAATCCCT AGGCTTTGGA
                1940                      1960                      1980
GATCCGCACT TACATTAGAG TTATGGGAAT ATACACATAT TAATGTGGCT CCCTTTTTCT
                2000                      2020                      2040
TGTGGGGGAA TAAAAGAGGA CTCCTCCTCA TTCCCTTTAA CATGGGGGAA AAAACTGACA
                2060                      2080                      2100
TTAAAAGATG AGACTAAATC TTTATCTTGA ATTTTACACA ACTACTTACG ACAAGGGAGA
                2120                      2140                      2160
TGTTTAGACC TGTTGGTATA CTTCAGAGTA CTTTTCATGA GTTCTTCCAC AGTGAACCCT
                2180                      2200                      2220
TGGATTACCT GGTGGCTTTT TCTAGCCAGA TTGCATTAAT CCTTACTGAG ATTGGATGGT
                2240                      2260                      2280
TTTCTTTCCT CTATTGGCGC CATTCTTCAG ATATTAAAGT TAAACCATCC ACTCCCTCAC
                2300                      2320                      2340
CTTCAGCCTT CAGTGAATGT GCTTTCTAGT TGTCAGGAAT GCTGAAGAAT TAACACTTTG
```

FIG. 2F

```
        2360                           2380                         2400
ACTCCTAAAT GTGATACTGG TGGGTAAGAG CAGGGCACAT TTAATTGTTT CGCTTTTGCT
        2420                           2440                         2460
TCTCTTTGGT CTGGGCACAT TTAATTGTT CGCTTTTGCT TCTCTTTGCT CTTTTCGAAT
        2480                           2500                         2520
ACTTAGTAAT CGAAAACCAT ATCCTGTAAT TTAATAAAAA AAACTAAGGA CGAAAAAACC
        2540                           2560                         2580
CCTCCAATTT TCCAAATGC AATCAGTGTA ACTAGGGGCT GTGTTTCTGC ATTAAAATAA
        2600                           2620                         2640
ATGTTTCAGG CTTTGTGGTC CTGATCAAGG TCCTCATTAA AAAATTGGAG TTCACCCTAG
        2660                           2680                         2700
GCTTTTCCCC TCTGTGACTG GCAGATAACA CATACTTTTG AAAGTAACTT TGGGATTTTT
        2720                           2740                         2760
TTTCTTAGGT GCAGCTCGAT TCTAAATCTTT TCATGCTGCA CACGATTCCT TTAATCGATA
        2780                           2800                         2820
GCATCCCTTAT CTGAAAGAAA TAACCATCTT CTCAACATGA CCTGCTTAAC CCAAATAAGA
```

FIG. 2G

```
                              2840                  2860                  2880
                    ACAGTGATCT TATAACCTCA TTGTTTCCTA ATCTATTTTA TTTCATCTCC TGCTAGTACT
                              2900                  2920                  2940
                    GTGCCGCTTC CCCCTCCCCC CACACAAAAT AAAAACAGTA TCTCGCTTCT GGCTCATTTT
```

FIG. 2H

```
                                     1            12
NPI-1                                MTTPGKENFRLK
                                     |:      |||.
SRP1                                 MDNGTDSSTSKFVPEYRRT
        13                                              58
NPI-1   SYKNKS-LNPDVWRRRREEEGLQLRKLKREEQLFKRRNVVTAEEETE
        ||||||  ||||  ||||||.. |||||||||.| |||| |.|.|.||
SRP1    NFKNKGRFSADELRRRRDTQQVELRKAKRDEALAKRRNFIPPTDGAD
        59                                              105
NPI-1   EEVMSDGGFHEAQISNMEMAPGGVITSDMIEMIFSKSPEQQLSATQK
        .|  .|||  ..|    ||..   |||.|||..  ||||||| |
SRP1    SDEEDESSVSADQQFYSQLQQ——ELPQMTQQLNSDDMQEQLSATVK
        106                                             150
NPI-1   FRKLLSKEPDPPIDE-VISTPGVVARFVEFLKR-KENCSLQFESAWV  |
        ||::||:|. ||||  |:  :|||:|:||:::   ::   ||:|:||. |Repeat #1
SRP1    FRQILSREHRPPID——VVIQAGVVPRLVEFMRE-NQPEMLQLEAAWA  |
        151                                      192
NPI-1   LTNIASGNSLQTRI——VIQARAV-PIFIELLSS-ESEDVQE-QAVWA  |
        |||||||.| ||::   |::| || |:|::||  : .| :|:| ||:|| |Repeat #2
SRP1    LTNIASGTSAQTKV——VVDADAV-PLFIQLLYT-GSVEVKE-QAIWA  |
        193                                      235
NPI-1   LGNIAGDSTMCRDY——VLDCNIL-PPLLQLFSKQNRLTMTR-NAVWA  |
        |||:||||| .|||  ||||| :   |:| ||:. |: :::.| .|.|: |Repeat #3
SRP1    LGNVAGDSTDYRDY——VLQCNAM-EPILGLFNS-NKPSLIR-TATWT  |
        236                                      277
NPI-1   LSNLCRGKSPPPEF——AKVSPCL-NVLSWLLFV-SDTDVLA-DACWA  |
        |||||||.|.|:.   :  ||. |  .|:  |::    ||:.|. |||| |Repeat #4
SRP1    LSNLCRGKKPQPDW——SVVSQAL-PTLAKLIYS-MDTETLV-DACWA  |
        278                                      318
NPI-1   LSYLSDGPNDKIQA———VIDAEYVET-VELLMH-NDYKVVS-PALRA  |
        :|||||||::  |||   |||.  . ||||  |:.   | : ||||| |Repeat #5
SRP1    ISYLSDGPQEAIQA———VIDVRIPKRLVELLSH-ESTLVQT-PALRA  |
        319                                      360
NPI-1   VGNIVTGDDIQTQV————ILNCSALQSLLHLLSS-PKESIKK-EACWT |
        ||||||:|:||||    ::| :.|.:| |||| |||:||| ||||| |Repeat #6
SRP1    VGNIVTGNDLQTQV————VINAGVLPALRLLLSS-PKENIKK-EACWT |
        361                                      402
NPI-1   ISNITAGNRAQIQT————VIDANIFPALISILQT-AEFRTRK-EAAWA |
        ||||||||.|||:   |||||::|:|:..|:. ||::|:| || || |Repeat #7
SRP1    ISNITAGNTEQIQA————VIDANLIPPLVKLLEV-AEYKTKK-EACWA |
```

FIG.3A

```
           403                                              445
NPI-1   ITNATSGG---SAEQIKYLVELGCIKPLCDLLTV-MDSKIVQ-VALNG  |
        |:||:|||   .::  |:|||. |||||||||.:  |::|::  |:|::  |Repeat #8
SRP1    ISNASSGGLQRPDIIRYLVSQGCIKPLCDLLEI-ADNRIIE-VTLDA   |
           446                                        490
NPI-1   LENILRLGEQEAKRNGTGINPYCALIEEAYGLDKIEFL-LSHENQEI
        ||||||:||.:  .| .||   .:||.| |::|| |    :||:.|
SRP1    LENILKMGEADKEARGLNINENADFIEKAGGMEKI-FNCQQNENDKI 491
NPI-1   YQKAFDLIEHYFGTEDE---DSSIAPQVDLNQQQYIFQQCEAPMEGFQL
        |:||:.:|| |||.|::   |.:::|| . |
SRP1    YEKAYKIIETYFGEEEDAVDETMAPQNAGNTFGFGSNVNQQFNFN
```

Repeat element Consensuses:
```
ARM:       L+NLS*+***N+*---ALL**GGL-PALV+LL*S-*+E**L*-*AA*A
              A           II   I  I              I
                          W    V  V              V NPI-1
& SRP1:    LSNI*SG***QPQ---*WI*AGV*PPLV-LL*S-*--*E*K+E-ACWA
              i               V A
```

FIG.3B

```
                    20                    40                    60
GGAGGCACCG AAGGGCAGCG CCGAGTCGGA GGGGGCGAAG ATTGACGCCA GTAAGAACGA 80                   100                   120
GGAGGATGAA GGCCATTCAA ACTCCTCCCC ACGACACTCT GAAGCAGCGA CGGCACAGCG 140                   160
GGAAGAATGG AAAATGTTTA TAGGAGGCCT TAGCTGGGAC ACTACAAAGA
```

FIG. 7

```
GAGGTCAATG TGGAGCTGAG GAAAGCTAAG AAGGATGACC AGATGCTGAA GAGGAGAAAT      60
 E  V  N    V  E  L  R    K  A  K    K  D  D    Q  M  L  K    R  R  N >

GTAAGCTCAT TTCCTGATGA TGCTACTTCT CCGCTGCAGG AAAACCGCAA CAACCAGGGC     120
 V  S  S    F  P  D  D    A  T  S    P  L  Q    E  N  R  N    N  Q  G >

ACTGTAAATT GGTCTGTTGA TGACATTGTC AAAGGCATAA ATAGCAGCAA TGTGGAAAAT     180
 T  V  N    W  S  V  D    D  I  V    K  G  I    N  S  S  N    V  E  N >

CAGCTCCAAG CTACTCAAGC TGCCAGGAAA CTACTTTCCA GAGAAAAACA GCCCCCCATA     240
 Q  L  Q    A  T  Q  A    A  R  K    L  L  S    R  E  K  Q    P  P  I >

GACAACATAA TCCGGGCTGG TTTGATTCCG AAATTTGTGT CCTTCTTGGG CAGAACTGAT     300
 D  N  I    I  R  A  G    L  I  P    K  F  V    S  F  L  G    R  T  D >

TGTAGTCCCA TTCAGTTTGA ATCTGCTTGG GCACTCACTA ACATTGCTTC TGGGACATCA     360
 C  S  P    I  Q  F  E    S  A  W    A  L  T    N  I  A  S    G  T  S >

FIG. 8A
```

```
GAACAAACCA AGGCTGTGGT AGATGGAGGT GCCATCCCAG CATTCATTTC TCTGTTGGCA
 E  Q  T    K  A  V  V   D  G  G    A  I  P    A  F  I  S   L  L  A>
         380                400                420

TCTCCCCATG CTCACATCAG TGAACAAGCT GTCTGGGCTC TAGGAAACAT TGCAGGTGAT
 S  P  H    A  H  I  S   E  Q  A    V  W  A    L  G  N  I   A  G  D>
         440                460                480

GGCTCAGTGT TCCGAGACTT GGTTATTAAG TACGGTGCAG TTGACCCACT GTTGGCTCTC
 G  S  V    F  R  D  L   V  I  K    Y  G  A    V  D  P  L   L  A  L>
         500                520                540

CTTGCAGTTC CTGATATGTC ATCTTTAGCA TGTGGCTACT TACGTAATCT TACCTGGACA
 L  A  V    P  D  M  S   S  L  A    C  G  Y    L  R  N  L   T  W  T>
         560                580                600

CTTTCTAATC TTTGCCGCAA CAAGAATCCT GCACCCCCGA TAGATGCTGT TGAGCAGATT
 L  S  N    L  C  R  N   K  N  P    A  P  P    I  D  A  V   E  Q  I>
         620                640                660

CTTCCTACCT TAGTTCGGCT CCTGCATCAT GATGATCCAG AAGTGTTAGC AGATACCTGC
 L  P  T    L  V  R  L   L  H  H    D  D  P    E  V  L  A   D  T  C>
         680                700                720
```

FIG. 8B

```
                                                                        780
                 740                        760
TGGGCTATTT  CCTACCTTAC  TGATGGTCCA  AATGAACGAA  TTGGCATGGT  GGTGAAAACA
 W  A  I    S  Y  L  T    D  G  P    N  E  R    I  G  M  V    V  K  T>

800                        820                        840
GGAGTTGTGC  CCCAACTTGT  GAAGCTTCTA  GGAGCTTCTG  AATTGCCAAT  TGTGACTCCT
 G  V  V    P  Q  L  V    K  L  L    G  A  S    E  L  P  I    V  T  P>

860                        880                        900
GCCCTAAGAG  CCATAGGGAA  TATTGTCACT  GGTACAGATG  AACAGACTCA  GGTTGTGATT
 A  L  R    A  I  G  N    I  V  T    G  T  D    E  Q  T  Q    V  V  I>

920                        940                        960
GATGCAGGAG  CACTCGCCGT  CTTTCCCAGC  CTGCTCACCA  ACCCCAAAAC  TAACATTCAG
 D  A  G    A  L  A  V    F  P  S    L  L  T    N  P  K  T    N  I  Q>

980                       1000                       1020
AAGGAAGCTA  CGTGGACAAT  GTCAAACATC  ACAGCCGGCC  GCCAGGACCA  GATACAGCAA
 K  E  A    T  W  T  M    S  N  I    T  A  G    R  Q  D  Q    I  Q  Q>

1040                       1060                       1080
GTTGTGAATC  ATGGATTAGT  CCCATTCCTT  GTCAGTGTTC  TCTCTAAGGC  AGATTTAAG
 V  V  N    H  G  L  V    P  F  L    V  S  V    L  S  K  A    D  F  K>

FIG. 8C
```

```
                                    1100                           1120                           1140
ACACAAAAGG  AAGCTGTGTG  GGCCGTGACC  AACTATACCA  GTGGTGGAAC  AGTTGAACAG
 T  Q  K     K  L  V       A  V  T     N  Y  T     S  G  G     T  V  E  Q>

1160                           1180                           1200
ATTGTGTACC  TTGTTCACTG  TGGCATAATA  GAACCGTTGA  TGAACCTCTT  AACTGCAAAA
 I  V  Y     L  V  H  C     G  I  I     E  P  L     M  N  L  L     T  A  K>

1220                           1240                           1260
GATACCAAGA  TTATTCTGGT  TATCCTGGAT  GCCATTTCAA  ATATCTTTCA  GGCTGCTGAG
 D  T  K     I  I  L  V     I  L  D     A  I  S     N  I  F  Q     A  A  E>

1280                           1300                           1320
AAACTAGGTG  AAACTAGCTG  CCCGTCTTCA  CAGATTCAAG  AACAAGGGAA  AAGACAGTAC
 K  L  G     E  T  S  C     P  S  S     Q  I  Q     E  Q  G  K     R  Q  Y>

1340                           1360                           1380
AGAAATGAGG  CGTCCGAGGC  GTCGCAGAAT  AGAGAAACTT  AGTATAATGA  TTGAAGAATG
 R  N  E     A  S  E  A     S  Q  N     R  E  T>

1400                           1420                           1440
TGGAGGCTTA  GACAAAATTG  AAGCTCTACA  AAACCATGAA  AATGAGTCTG  TGTATAAGGC
```

FIG. 8D

```
                           1460                     1480                     1500
TTCGTTAAGC TTAATTGAGA AGTATTCTC TGTAGAGGAA GAGGAAGATC AAAACGTTGT 1520                     1540                     1560
ACCAGAAACT ACCCTCGAAG GCTACACTTT CCAAGTTCAG GATGGGGCTC CTGGGACCTT 1580                     1600                     1620
TAACTTTTAG ATCATGTAGC TGAGACATAA ATTGTGTGTG TACTACGTTT GGTATTTTGT 1640                     1660                     1680
CTTATTGTTT CTCTACTAAG AACTCTTTCT TAAATGTGGT TTGTTACTGT AGCACTTTTT 1700                     1720                     1740
ACACTGAAAC TATACTTGAA CAGTTCCAAC TGTACATACA TACTGTATGA AGCTGTCCT 1760                     1780                     1800
CTGACTAGGT TTCTAATTTC TATGTGGAAT TTCCTATCTT GCAGCATCCT GTAAATAAAC

1820
ATTCAAGTCC ACCCTTTTCT TGACTTC
```

FIG. 8E

```
              20                  40                  60
GAACGACCAA GAGGGTGTTC GACTGCTAGA GCCGAGCAGA AGCGTGCCTA AATCAAAGGA 80                 100                 120
ACTTGTTTCT TCAAGCTCTT CTGGCAGTGA TTCTGACAGT GAGGTTGACA AAAAGTTAAG 140                 160                 180
CAGGAAAAAG CAAGTTGCTC CAGAAAAACC TGTAAAGAAA CAAAAGACAG GTGAGACTTC 200                 220                 240
GAGAGCCCTG TCATCTTCTA AACAGAGCAG CAGCAGCAGA GATGATAACA TGTTTCAGAT

TGGGAAAATG AGGTCAGTT
```

FIG. 9

```
                                        20                    40                    60
TGTCGACTGT GGCTTTGAGC ATCCGTCAGA AGTCCAGCAT GAGTGCATCC CTCAGGCCAT
                                        80                   100                   120
TCTGGGAATG GATGTCCTGT GCCAGGCCAA GTCGGGCATG GGAAAGACAG CAGTGTTTGT
                                       140                   160                   180
CTTGGCCACA CTGCAACAGC TGGAGCCAGT TACTGGGCAG GTGTCTGTAC TGGTGATGTG
                                       200                   220
TCACACTCGG GAGTTGGCTT TTCAGATCAG CAAGGAATAT G
```

FIG. 10

```
                  20         40         60
ATTTGTAAAC CCCGGAGCGA GGTTCTGCTT ACCCGAGGCC GCTGCTGTGC GGAGACCCCC
                  80         100        120
GGGTGAAGCC ACCGTCATCA TGTCTGACCA GGAGGCAAAA CCTTCAACTG AGGACTTGGG
                  140        160        180
GGATAAGAAG GAAGGTGAAT ATATTAAACT CAAAGTCATT GGACAGGATA GCAGTGAGAT
                  200        220        240
TCACTTCAAA GTGAAAATGA CAACACATCT CAAGAAACTC AAAGAATCAT ACTGTCAAAG
                  260        280        300
ACAGGGTGTT CCAATGAATT CACTCAGGTT TCTCTTTGAG GGTCAGAGAA TTGCTGATAA
                  320        340        360
TCATACTCCA AAAGAACTGG GAATGGAGGA AGAAGTTGTG ATTGAAGTTT ATCAGGAACA
AACGGGGGT CA
```

FIG. 11

```
-103  TCTGACCCCTCGTCCCGCCCCCGC                                                                                        -80

-81   CATTCGCCGCCTCCTCCTGTCCCGCAGTCGGCTCCAGGGCTCTGCTTGTCGTTCGTGTCGTTGCAGGCCTTATTC                                      -1

1    ATGGGCTCACCGCTGAGGTTCGACGGTTGTACTGGTCGCGGGCGGGTGGTGCTGGTCACCGGCGCGGCAGGATTGGGCCGAGCCTATGCCT                       80
      M  G  S  P  L  R  F  D  G  R  V  V  L  V  T  G  A  G  A  G  L  G  R  A  Y  A  L                                27

81    GGCTTTTGCAGAAAGAGGAGCGTTAGTGTTGTGAATGATTGGGAGGGACTTCAAAGGAGTTGGTAAAGGCTCCTTAG                                    160
      A  F  A  E  R  G  A  L  V  V  V  N  D  L  G  G  D  F  K  G  V  G  K  G  S  L                                   53

161   CTGATAAGGTTGTTGAAGAAATAAGAAGGAGAGGTGAAAAGCAGTGGCCAACTATGATTCAGTGGAAGAAGGAGAGAAG                                   240
      A  D  K  V  V  E  E  I  R  R  R  G  G  K  A  V  A  N  Y  D  S  V  E  E  G  E  K                                80

241   GTTGTGAAGACAGCCCTGATGCTTTTGGAAGAATAGATGTTGTGAACAATGCTGAATTCTGAGGGATCATTCCTT                                      320
      V  V  K  T  A  L  D  A  F  G  R  I  D  V  V  V  N  N  A  G  I  L  R  D  H  S  F                                107

321   TGCTAGGATAAGTGATGAAGACTGGGATATAATCCACAGAGTTCATTTGCGGGTTCATTCCAAGTGACACGGCAGCAT                                   400
      A  R  I  S  D  E  D  W  D  I  H  R  V  H  L  R  G  S  F  Q  V  T  R  A  A                                     133

401   GGGAACACATGAAGAAACAGAAGTATGGAAGGATTATTATGACTTCAGCAGCTTCATCAGCTTCAGGAATATATGGCAACTTTGGCCAG                        480
      W  E  H  M  K  K  Q  K  Y  G  R  I  I  M  T  S  S  A  S  G  I  Y  G  N  F  G  Q                                160

481   GCCAATTATAGTGCTGCAAAGTTGGGTCTTCTCTGGGCTTGCAAATTCTCTTGCAATGAAGGCAGGAAAAGCAACATTCA                                  560
      A  N  Y  S  A  A  K  L  G  L  L  G  L  A  N  S  L  A  I  E  G  R  K  S  N  I  H                                187

561   TTGTAACACCATTGCTCCTAATGCGGGATGACTCAGACAGTTATGCCTGAAGATCTTGTGGAAGCCTTGAAGC                                        640
      C  N  T  I  A  P  N  A  G  S  R  M  T  Q  T  V  M  P  E  D  L  V  E  A  L  K                                  213

641   CAGAGTATGTGGCACCTCTTTGTCCTTTGGCTTTGTGGCTCCATGAGTCTTGTGAGGAGAATGGTGGCTTGTTTGAGGTTGGTGCA                           720
      P  E  Y  V  A  P  L  V  L  W  L  C  H  E  S  C  E  E  N  G  G  L  F  E  V  G  A                                240
```

FIG. 12A

```
 721  GGATGGATTGGAAATTACGCTGGGAGCGGACTCTTGAGCTATTGTAAGACAAAAGAATCACCCAATGACTCCTGAGGC  800
       G  W  I  G  K  L  R  W  E  R  T  L  G  A  I  V  R  Q  K  N  H  P  M  T  P  E  A   267

801  AGTCAAGGCTAACTGGAAGAGATCTGTGACTTTGAGAATGCCAGCAAGCCTCAGAGTATCCAAGAATCAACTGGCAGTA  880
       V  K  A  N  W  K  K  I  C  D  F  E  N  A  S  K  P  Q  S  I  Q  E  S  T  G  S    293

881  TAATTGAAGTTCTGAGTAAAATAGATTCAGAAGGAGGAGTTTCAGCAAATCATAGTCGTGCAACGTCTACAGCAACA   960
       I  I  E  V  L  S  K  I  D  S  E  G  G  V  S  A  N  H  T  S  R  A  T  S  T  A  T   320

961  TCAGGATTTGCTGGAGCTATTGGCCAGAAACTCCCTCCATTTCTTATGCTTATACGAACTGGAAGCTATTATGTATGC  1040
       S  G  F  A  G  A  I  G  Q  K  L  P  P  F  S  Y  A  Y  T  E  L  E  A  I  M  Y  A   347

1041  CCTTGGAGTGGGAGCGTCAATCAAGGATCCAAAGATTTGAAATTTATTTATGAAGGAAGTTCTGATTTCTCCTGTTGC  1120
       L  G  V  G  A  S  I  K  D  P  K  D  L  K  F  I  Y  E  G  S  S  D  F  S  C  L     373

1121  CCACCTTCGGAGTTATCATAGGTCAGAAATTCCTGGAGGATTAGCAGAAATTCCTGGACTTTCAATCAACTTT      1200
       P  T  F  G  V  I  I  G  Q  K  S  M  M  G  G  G  L  A  E  I  P  G  L  S  I  N  F   400

1201  GCAAAGGTTCTTCATGGAGAGCAGTACTTAGAGTTATATAAACCACTTCCCAGAGCAGGAAAATTAAAATGTGAAGCAGT  1280
       A  K  V  L  H  G  E  Q  Y  L  E  L  Y  K  P  L  P  R  A  G  K  L  K  C  E  A  V   427

1281  TGTTGCTGATGTCCTAGATAAAGGATCCGGTGTAGTGATTATTATGGATGTCTATTCTTATTCTGAGAAGGAACTTATAT  1360
       V  A  D  V  L  D  K  G  S  G  V  V  I  I  M  D  V  Y  S  Y  S  E  K  E  L  I     453

1361  GCCACAATCAGTTCTCTCTTTTCTTTGTTGGCTCTGGAGGCTTTGGTGGTGGAAAACGACATCAGACAAAGTAGCT    1440
       C  H  N  Q  F  S  L  F  L  V  G  S  G  G  F  G  G  G  K  R  T  S  D  K  V  K  V  A  480
```

FIG. 12B

```
1441  GTAGCCATACCTAATAGACCTCCTGATGCTGTACTTACAGATACCACCACCTCTCTTAATCAGGTGCTGTTTGTACCGCCTCAG  1520
       V  A  I  P  N  R  P  P  D  A  V  L  T  D  T  T  S  L  N  Q  A  A  L  Y  R  L  S      507

1521  TGGAGACCGGAATCCCTTACACATTGATCTCTAACTTGCTAGTCTTGCTAGTTTGACAAGCCATATTACATGATTAT  1600
       G  D  R  N  P  L  H  I  D  P  N  F  A  S  L  A  G  F  D  K  P  I  L  H  G  L        533

1601  GTACATTTGGATTTTCTGCCAGGCGTGTTGTTACAGCAGTTTGCAGATAATGATGTGTCAAGATTCAAGGCAGTTAAGGCT  1680
       C  T  F  G  F  S  A  R  R  V  L  Q  Q  F  A  D  N  D  V  S  R  F  K  A  V  K  A      560

1681  CGTTTTGCAAAACCAGTATATCCAGGAGACATAAACTCTACAAACTGAGATGTGGAAGAAGGAAACAGAATTCATTTCAAAC  1760
       R  F  A  K  P  V  Y  P  G  Q  T  L  Q  T  E  M  W  K  E  G  N  R  I  H  F  Q  T      587

1761  CAAGGTCCAAGAAACTGGAGACATTGTCATTTCAAATGCATATGTGGATCTTGCACCAACATCTGGTACTTCAGCTAAGA  1840
       K  V  Q  E  T  G  D  I  V  I  S  N  A  Y  V  D  L  A  P  T  S  G  T  S  A  K        613

1841  CACCCCTCTGAGGGCGGAAGCTTCAGAGTACCTTGTATTTGAGGAAATAGGACGCGCTAAAGGATATTGGGCCTGAG  1920
       T  P  S  E  G  G  K  L  Q  S  T  F  V  F  E  E  I  G  R  R  L  K  D  I  G  P  E      640

1921  GTGGTGAAGAAGTAAATGCTGTATTTGAGTGGCATATAACCAAAGGCGGAAATATTGGGGCTAAGTGGACTATTGACCT  2000
       V  V  K  K  V  N  A  V  F  E  W  H  I  T  K  G  G  N  I  G  A  K  W  T  I  D  L      667

2001  GAAAAGTGGTTCTGGAAGTGTACCAAGGCCCTGCTGATACAACAATCATACTTTCAGATGAAGATT  2080
       K  S  G  S  G  K  V  Y  Q  G  P  A  K  G  A  A  D  T  T  I  I  L  S  D  E  D        693

2081  TCATGGAGGTGGTGGTCCTGGCAAGCTTGACCCTCAGAAGGCATTCTTTAGTGGCAGGCTGAAGGCTAGAGGAAACATCATG  2160
       F  M  E  V  V  L  G  K  L  D  P  Q  K  A  F  F  S  G  R  L  K  A  R  G  N  I  M      720

2161  CTGAGCCAGAAACTTCAGATGATTCTTAAAGACTACGCCAAGCTCTGAAGGGCACACTATTAATAAAAATGGAAT  2240
       L  S  Q  K  L  Q  M  I  L  K  D  Y  A  K  L                                          735
```

FIG. 12C

```
2241  CATTAAATACTCTCTTCACCCAAATATGCTTGATTATTCTGCAAAAGTGATTAGAACTAAGATGCAGGGGAAATTGCTTA  2320
2321  ACATTTCAGATATCAGATAACTGCAGATTTTCATTTTCTACTAATTTTCATGTATCATTATTTTACAAGGAACTATA     2400
2401  TATAAGCTAGCACATAATTATCCTTCTGTTCTTAGATCTGTATCTTCATAATAAAAAATTTGCCCAAGTCCTGTTCC    2480
2481  TTAGAATTGTGATAGCATTGATAAGTTGAAAGGAAAATTAAATCAATAAAGGCCTTTGATACCTTTAAAAAAAAAAA   2560
      AAAAAAAAAA
```

FIG. 12D

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

GCAAAGCAGG AGAAACCAC                                                    19

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

GGGTCCATCT GATAGATATG AGAG                                           24

(2) INFORMATION FOR SEQ ID NO:3:

(i) SEQUENCE CHARACTERISTICS:
       (A) LENGTH: 48 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: modified_base
       (B) LOCATION: 36
       (D) OTHER INFORMATION: /mod_base= i (ix) FEATURE:
       (A) NAME/KEY: modified_base
       (B) LOCATION: 37
       (D) OTHER INFORMATION: /mod_base= i (ix) FEATURE:
       (A) NAME/KEY: modified_base
       (B) LOCATION: 41
       (D) OTHER INFORMATION: /mod_base= i (ix) FEATURE:
       (A) NAME/KEY: modified_base
       (B) LOCATION: 42
       (D) OTHER INFORMATION: /mod_base= i (ix) FEATURE:
       (A) NAME/KEY: modified_base
       (B) LOCATION: 46
       (D) OTHER INFORMATION: /mod_base= i (ix) FEATURE:
       (A) NAME/KEY: modified_base
       (B) LOCATION: 47
       (D) OTHER INFORMATION: /mod_base= i (xi) SEQUENCE DESCRIPTION: SEQ ID NO:3:

CUACUACUAC UAGGCCACGC GTCGACTACT ACGGGNNGGG NNGGGNNG                 48

(2) INFORMATION FOR SEQ ID NO:4:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:4:

TCCTGATGTT GCTGTAGACG                                                20

(2) INFORMATION FOR SEQ ID NO:5:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:5:

GCACGACTAG TATGATTTGC                                                20

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:6:

```
Thr Gly Ala Gly Ala Gly Leu Gly
1               5
```

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:7:

```
Tyr Ser Ala Ala Lys
1               5
```

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: DNA (ix) FEATURE:
        (A) NAME/KEY: CDS
        (B) LOCATION: 1..27

(xi) SEQUENCE DESCRIPTION: SEQ ID NO:8:

```
GAC TGG CTG GAA TTC CCC ATG GCG TCC                          27
Asp Trp Leu Glu Phe Pro Met Ala Ser
1               5
```

(2) INFORMATION FOR SEQ ID NO:9:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:9:

```
Asp Trp Leu Glu Phe Pro Met Ala Ser
1               5
```

(2) INFORMATION FOR SEQ ID NO:10:

(i) SEQUENCE CHARACTERISTICS:
        (A) LENGTH: 2940 base pairs
        (B) TYPE: nucleic acid
        (C) STRANDEDNESS: unknown
        (D) TOPOLOGY: unknown (ii) MOLECULE TYPE: cDNA (ix) FEATURE:

-continued (A) NAME/KEY: CDS
(B) LOCATION: 47..1663

(xi) SEQUENCE DESCRIPTION: SEQ ID NO:10:

```
CTAACTTCAG CGGTGGCACC GGGATCGGTT GCCTTGAGCC TGAAAT ATG ACC ACC              55
                                                    Met Thr Thr
                                                      1

CCA GGA AAA GAG AAC TTT CGC CTG AAA AGT TAC AAG AAC AAA TCT CTG            103
Pro Gly Lys Glu Asn Phe Arg Leu Lys Ser Tyr Lys Asn Lys Ser Leu
          5                  10                  15

AAT CCC GAT GAG ATG CGC AGG AGG AGG GAG GAA GGA CTG CAG TTA                151
Asn Pro Asp Glu Met Arg Arg Arg Arg Glu Glu Gly Leu Gln Leu
 20              25                  30                  35

CGA AAG CAG AAA AGA GAA GAG CAG TTA TTC AAG CGG AGA AAT GTT GCT            199
Arg Lys Gln Lys Arg Glu Glu Gln Leu Phe Lys Arg Arg Asn Val Ala
                 40                  45                  50

ACA GCA GAA GAA GAA ACA GAA GAA GAA GTT ATG TCA GAT GGA GGC TTT            247
Thr Ala Glu Glu Glu Thr Glu Glu Glu Val Met Ser Asp Gly Gly Phe
                     55                  60                  65

CAT GAG GCT CAG ATT AGT AAC ATG GAG ATG GCA CCA GGT GGT GTC ATC            295
His Glu Ala Gln Ile Ser Asn Met Glu Met Ala Pro Gly Gly Val Ile
             70                  75                  80

ACT TCT GAC ATG ATT GAG ATG ATA TTT TCC AAA AGC CCA GAG CAA CAG            343
Thr Ser Asp Met Ile Glu Met Ile Phe Ser Lys Ser Pro Glu Gln Gln
 85                  90                  95

CTT TCA GCA ACA CAG AAA TTC AGG AAG CTG CTT TCA AAA GAA CCT AAC            391
Leu Ser Ala Thr Gln Lys Phe Arg Lys Leu Leu Ser Lys Glu Pro Asn
100                 105                 110                 115

CCT CCT ATT GAT GAA GTT ATC AGC ACA CCA GGA GTA GTG GCC AGG TTT            439
Pro Pro Ile Asp Glu Val Ile Ser Thr Pro Gly Val Val Ala Arg Phe
                120                 125                 130

GTG GAG TTC CTC AAA CGA AAA GAG AAT TGT TCA CTG CAG TTT GAA TCA            487
Val Glu Phe Leu Lys Arg Lys Glu Asn Cys Ser Leu Gln Phe Glu Ser
                135                 140                 145

GCT TGG GTA CTG ACA AAT ATT GCT TCA GGA AAT TCT CTT CAG ACC CGA            535
Ala Trp Val Leu Thr Asn Ile Ala Ser Gly Asn Ser Leu Gln Thr Arg
            150                 155                 160

ATT GTG ATT CAG GCA AGA GCT GTG CCC ATC TTC ATA GAG TTG CTC AGC            583
Ile Val Ile Gln Ala Arg Ala Val Pro Ile Phe Ile Glu Leu Leu Ser
165                 170                 175

TCA GAG TTT GAA GAT GTC CAG GAA CAG GCA GTC TGG GCT CTT GGC AAC            631
Ser Glu Phe Glu Asp Val Gln Glu Gln Ala Val Trp Ala Leu Gly Asn
180                 185                 190                 195

ATT GCT GGA GAT AGT ACC ATG TGC AGG GAC TAT GTC TTA GAC TGC AAT            679
Ile Ala Gly Asp Ser Thr Met Cys Arg Asp Tyr Val Leu Asp Cys Asn
                200                 205                 210

ATC CTT CCC CCT CTT TTG CAG TTA TTT TCA AAG CAA AAC CGC CTG ACC            727
Ile Leu Pro Pro Leu Leu Gln Leu Phe Ser Lys Gln Asn Arg Leu Thr
            215                 220                 225

ATG ACC CGG AAT GCA GTA TGG GCT TTG TCT AAT CTC TGT AGA GGG AAA            775
Met Thr Arg Asn Ala Val Trp Ala Leu Ser Asn Leu Cys Arg Gly Lys
                230                 235                 240

AGT CCA CCT CCA GAA TTT GCA AAG GTT TCT CCA TGT CTG AAT GTG CTT            823
Ser Pro Pro Pro Glu Phe Ala Lys Val Ser Pro Cys Leu Asn Val Leu
245                 250                 255

TCC TGG TTG CTG TTT GTC AGT GAC ACT GAT GTA CTG GCT GAT GCC TGC            871
Ser Trp Leu Leu Phe Val Ser Asp Thr Asp Val Leu Ala Asp Ala Cys
260                 265                 270                 275

TGG GCC CTC TCA TAT CTA TCA GAT GGA CCC AAT GAT AAA ATT CAA GCG            919
Trp Ala Leu Ser Tyr Leu Ser Asp Gly Pro Asn Asp Lys Ile Gln Ala
```

-continued

```
            280              285              290
GTC ATC GAT GCG GGA GTA TGT AGG AGA CTT GTG GAA CTG CTG ATG CAT        967
Val Ile Asp Ala Gly Val Cys Arg Arg Leu Val Glu Leu Leu Met His
            295              300              305

AAT GAT TAT AAA GTG GTT TCT CCT GCT TTG CGA GCT GTG GGA AAC ATT       1015
Asn Asp Tyr Lys Val Val Ser Pro Ala Leu Arg Ala Val Gly Asn Ile
            310              315              320

GTC ACA GGG GAT GAT ATT CAG ACA CAG GTA ATT CTG AAT TGC TCA GCT       1063
Val Thr Gly Asp Asp Ile Gln Thr Gln Val Ile Leu Asn Cys Ser Ala
            325              330              335

CTG CAG AGT TTA TTG CAT TTG CTG AGT AGC CCA AAG GAA TCT ATC AAA       1111
Leu Gln Ser Leu Leu His Leu Leu Ser Ser Pro Lys Glu Ser Ile Lys
340              345              350              355

AAG GAA GCA TGT TGG ACG ATA TCT AAT ATT ACA GCT GGA AAT AGG GCA       1159
Lys Glu Ala Cys Trp Thr Ile Ser Asn Ile Thr Ala Gly Asn Arg Ala
                 360              365              370

CAG ATC CAG ACT GTG ATA GAT GCC AAC ATT TTC CCA GCC CTC ATT AGT       1207
Gln Ile Gln Thr Val Ile Asp Ala Asn Ile Phe Pro Ala Leu Ile Ser
            375              380              385

ATT TTA CAA ACT GCT GAA TTT CGG ACA AGA AAA GAA GCA GCT TGG GCC       1255
Ile Leu Gln Thr Ala Glu Phe Arg Thr Arg Lys Glu Ala Ala Trp Ala
            390              395              400

ATC ACA AAT GCA ACT TCT GGA GGA TCA GCT GAA CAG ATC AAG TAC CTA       1303
Ile Thr Asn Ala Thr Ser Gly Gly Ser Ala Glu Gln Ile Lys Tyr Leu
            405              410              415

GTA GAA CTG GGT TGT ATC AAG CCG CTC TGT GAT CTC CTC ACG GTC ATG       1351
Val Glu Leu Gly Cys Ile Lys Pro Leu Cys Asp Leu Leu Thr Val Met
420              425              430              435

GAC TCT AAG ATT GTA CAG GTT GCC CTA AAT GGC TTG GAA AAT ATC CTG       1399
Asp Ser Lys Ile Val Gln Val Ala Leu Asn Gly Leu Glu Asn Ile Leu
                 440              445              450

AGG CTT GGA GAA CAG GAA GCC AAA AGG AAC GGC ACT GGC ATT AAC CCT       1447
Arg Leu Gly Glu Gln Glu Ala Lys Arg Asn Gly Thr Gly Ile Asn Pro
            455              460              465

TAC TGT GCT TTG ATT GAA GAA GCT TAT GGT CTG GAT AAA ATT GAG TTC       1495
Tyr Cys Ala Leu Ile Glu Glu Ala Tyr Gly Leu Asp Lys Ile Glu Phe
            470              475              480

TTA CAG AGT CAT GAA AAC CAG GAG ATC TAC CAA AAG GCC TTT GAT CTT       1543
Leu Gln Ser His Glu Asn Gln Glu Ile Tyr Gln Lys Ala Phe Asp Leu
            485              490              495

ATT GAG CAT TAC TTC GGG ACC GAA GAT GAA GAC AGC AGC ATT GCA CCC       1591
Ile Glu His Tyr Phe Gly Thr Glu Asp Glu Asp Ser Ser Ile Ala Pro
500              505              510              515

CAG GTT GAC CTT AAC CAG CAG CAG TAC ATC TTC CAA CAG TGT GAG GCT       1639
Gln Val Asp Leu Asn Gln Gln Gln Tyr Ile Phe Gln Gln Cys Glu Ala
                 520              525              530

CCT ATG GAA GGT TTC CAG CTT TGA AGCAATACTC TGCTTTCACG TACCTGTGCT      1693
Pro Met Glu Gly Phe Gln Leu  *
            535

CAGACCAGGC TACCCAGTCG AGTCCTCTTG TGGAGCCCAC AGTCCTCATG GAGCTAACTT     1753

CTCAAATGTT TTCCATAATA CTGTTTGCGC TCATTTGCTT GCCTTGCGCA CCTGCTCTCT     1813

TACACACATC TGGAAAACCT CCGGCTCTCT GTGGTGGGAT ACCCTTCTAA TAAAAGGGTA     1873

ACCAGAACGG CCCACTCTCT TTTACGGAAA AATCCCTAGG CTTTGGAGAT CCGCACTTAC     1933

ATTAGAGTTA TGGGAATATA CACATATTAA TGTGGCTCCC TTTTTCTTGT GGGGGAATAA     1993

AAGAGGACTC CTCCTCATTC CCTTTAACAT GGGGGAAAAA ACTGACATTA AAAGATGAGA     2053

CTAAATCTTT ATCTTGAATT TTACACAACT ACTTACGACA AGGGAGATGT TTAGACCTGT     2113
```

-continued

```
TGGTATACTT CAGAGTACTT TTCATGAGTT CTTCCACAGT GAACCCTTGG ATTACCTGGT    2173

GGCTTTTTCT AGCCAGATTG CATTAATCCT TACTGAGATT GGATGGTTTT CTTTCCTCTA    2233

TTGGCGCCAT TCTTCAGATA TTAAAGTTAA ACCATCCACT CCCTCACCTT CAGCCTTCAG    2293

TGAATGTGCT TTCTAGTTGT CAGGAATGCT GAAGAATTAA CACTTTGACT CCTAAATGTG    2353

ATACTGGTGG GTAAGAGCAG GGCACATTTA ATTTGTTCGC TTTTGCTTCT CTTTGGTCTG    2413

GGCACATTTA ATTTGTTCGC TTTTGCTTCT CTTTGGTCTT TTCGAATACT TAGTAATCGA    2473

AAACCATATC CTGTAATTTA ATAAAAAAAA CTAAGGACGA AAAAACCCCT CCAATTTTCC    2533

CAAATGCAAT CAGTGTAACT AGGGGCTGTG TTTCTGCATT AAAATAAATG TTTCAGGCTT    2593

TGTGGTCCTG ATCAAGGTCC TCATTAAAAA ATTGGAGTTC ACCCTAGGCT TTTCCCCTCT    2653

GTGACTGGCA GATAACACAT ACTTTTGAAA GTAACTTTGG GATTTTTTTT CTTAGGTGCA    2713

GCTCGATTCT AATCTTTTCA TGCTGCACAC GATTCCTTTA ATCGATAGCA TCCTTATCTG    2773

AAAGAAATAA CCATCTTCTC AACATGACCT GCTTAACCCA AATAAGAACA GTGATCTTAT    2833

AACCTCATTG TTTCCTAATC TATTTTATTT CATCTCCTGC TAGTACTGTG CCGCTTCCCC    2893

CTCCCCCCAC ACAAAATAAA AACAGTATCT CGCTTCTGGC TCATTTT                  2940
```

(2) INFORMATION FOR SEQ ID NO:11:

(i) SEQUENCE CHARACTERISTICS:
        (A) LENGTH: 538 amino acids
        (B) TYPE: amino acid
        (D) TOPOLOGY: linear (ii) MOLECULE TYPE: protein (xi) SEQUENCE DESCRIPTION: SEQ ID NO:11:

```
Met Thr Thr Pro Gly Lys Glu Asn Phe Arg Leu Lys Ser Tyr Lys Asn
  1               5                  10                  15

Lys Ser Leu Asn Pro Asp Glu Met Arg Arg Arg Glu Glu Gly
             20                  25                  30

Leu Gln Leu Arg Lys Gln Lys Arg Glu Glu Gln Leu Phe Lys Arg Arg
         35                  40                  45

Asn Val Ala Thr Ala Glu Glu Thr Glu Glu Val Met Ser Asp
     50                  55                  60

Gly Gly Phe His Glu Ala Gln Ile Ser Asn Met Glu Met Ala Pro Gly
 65                  70                  75                  80

Gly Val Ile Thr Ser Asp Met Ile Glu Met Ile Phe Ser Lys Ser Pro
                 85                  90                  95

Glu Gln Gln Leu Ser Ala Thr Gln Lys Phe Arg Lys Leu Leu Ser Lys
                100                 105                 110

Glu Pro Asn Pro Pro Ile Asp Glu Val Ile Ser Thr Pro Gly Val Val
            115                 120                 125

Ala Arg Phe Val Glu Phe Leu Lys Arg Lys Glu Asn Cys Ser Leu Gln
        130                 135                 140

Phe Glu Ser Ala Trp Val Leu Thr Asn Ile Ala Ser Gly Asn Ser Leu
145                 150                 155                 160

Gln Thr Arg Ile Val Ile Gln Ala Arg Ala Val Pro Ile Phe Ile Glu
                165                 170                 175

Leu Leu Ser Ser Glu Phe Glu Asp Val Gln Glu Gln Ala Val Trp Ala
            180                 185                 190

Leu Gly Asn Ile Ala Gly Asp Ser Thr Met Cys Arg Asp Tyr Val Leu
        195                 200                 205
```

```
Asp Cys Asn Ile Leu Pro Pro Leu Leu Gln Leu Phe Ser Lys Gln Asn
    210                 215                 220

Arg Leu Thr Met Thr Arg Asn Ala Val Trp Ala Leu Ser Asn Leu Cys
225                 230                 235                 240

Arg Gly Lys Ser Pro Pro Glu Phe Ala Lys Val Ser Pro Cys Leu
                245                 250                 255

Asn Val Leu Ser Trp Leu Leu Phe Val Ser Asp Thr Asp Val Leu Ala
                260                 265                 270

Asp Ala Cys Trp Ala Leu Ser Tyr Leu Ser Asp Gly Pro Asn Asp Lys
            275                 280                 285

Ile Gln Ala Val Ile Asp Ala Gly Val Cys Arg Arg Leu Val Glu Leu
        290                 295                 300

Leu Met His Asn Asp Tyr Lys Val Val Ser Pro Ala Leu Arg Ala Val
305                 310                 315                 320

Gly Asn Ile Val Thr Gly Asp Asp Ile Gln Thr Gln Val Ile Leu Asn
                325                 330                 335

Cys Ser Ala Leu Gln Ser Leu Leu His Leu Leu Ser Ser Pro Lys Glu
                340                 345                 350

Ser Ile Lys Lys Glu Ala Cys Trp Thr Ile Ser Asn Ile Thr Ala Gly
            355                 360                 365

Asn Arg Ala Gln Ile Gln Thr Val Ile Asp Ala Asn Ile Phe Pro Ala
    370                 375                 380

Leu Ile Ser Ile Leu Gln Thr Ala Glu Phe Arg Thr Arg Lys Glu Ala
385                 390                 395                 400

Ala Trp Ala Ile Thr Asn Ala Thr Ser Gly Gly Ser Ala Glu Gln Ile
                405                 410                 415

Lys Tyr Leu Val Glu Leu Gly Cys Ile Lys Pro Leu Cys Asp Leu Leu
                420                 425                 430

Thr Val Met Asp Ser Lys Ile Val Gln Val Ala Leu Asn Gly Leu Glu
            435                 440                 445

Asn Ile Leu Arg Leu Gly Glu Gln Glu Ala Lys Arg Asn Gly Thr Gly
450                 455                 460

Ile Asn Pro Tyr Cys Ala Leu Ile Glu Glu Ala Tyr Gly Leu Asp Lys
465                 470                 475                 480

Ile Glu Phe Leu Gln Ser His Glu Asn Gln Glu Ile Tyr Gln Lys Ala
                485                 490                 495

Phe Asp Leu Ile Glu His Tyr Phe Gly Thr Glu Asp Glu Asp Ser Ser
            500                 505                 510

Ile Ala Pro Gln Val Asp Leu Asn Gln Gln Gln Tyr Ile Phe Gln Gln
            515                 520                 525

Cys Glu Ala Pro Met Glu Gly Phe Gln Leu
            530                 535
```

(2) INFORMATION FOR SEQ ID NO:12:

(i) SEQUENCE CHARACTERISTICS:
      (A) LENGTH: 542 amino acids
      (B) TYPE: amino acid
      (C) STRANDEDNESS:
      (D) TOPOLOGY: unknown (ii) MOLECULE TYPE: protein (xi) SEQUENCE DESCRIPTION: SEQ ID NO:12:

```
Met Asp Asn Gly Thr Asp Ser Ser Thr Ser Lys Phe Val Pro Glu Tyr
1               5                   10                  15
```

-continued

```
Arg Arg Thr Asn Phe Lys Asn Lys Gly Arg Phe Ser Ala Asp Glu Leu
            20                  25                  30
Arg Arg Arg Arg Asp Thr Gln Gln Val Glu Leu Arg Lys Ala Lys Arg
            35                  40                  45
Asp Glu Ala Leu Ala Lys Arg Arg Asn Phe Ile Pro Pro Thr Asp Gly
            50                  55                  60
Ala Asp Ser Asp Glu Glu Asp Glu Ser Ser Val Ser Ala Asp Gln Gln
 65                  70                  75                  80
Phe Tyr Ser Gln Leu Gln Gln Glu Leu Pro Gln Met Thr Gln Gln Leu
                85                  90                  95
Asn Ser Asp Asp Met Gln Glu Gln Leu Ser Ala Thr Val Lys Phe Arg
                100                 105                 110
Gln Ile Leu Ser Arg Glu His Arg Pro Pro Ile Asp Val Val Ile Gln
                115                 120                 125
Ala Gly Val Val Pro Arg Leu Val Glu Phe Met Arg Glu Asn Gln Pro
            130                 135                 140
Glu Met Leu Gln Leu Glu Ala Ala Trp Ala Leu Thr Asn Ile Ala Ser
145                 150                 155                 160
Gly Thr Ser Ala Gln Thr Lys Val Val Asp Ala Asp Ala Val Pro
                165                 170                 175
Leu Phe Ile Gln Leu Leu Tyr Thr Gly Ser Val Glu Val Lys Glu Gln
                180                 185                 190
Ala Ile Trp Ala Leu Gly Asn Val Ala Gly Asp Ser Thr Asp Tyr Arg
            195                 200                 205
Asp Tyr Val Leu Gln Cys Asn Ala Met Glu Pro Ile Leu Gly Leu Phe
            210                 215                 220
Asn Ser Asn Lys Pro Ser Leu Ile Arg Thr Ala Thr Trp Thr Leu Ser
225                 230                 235                 240
Asn Leu Cys Arg Gly Lys Lys Pro Gln Pro Asp Trp Ser Val Val Ser
                245                 250                 255
Gln Ala Leu Pro Thr Leu Ala Lys Leu Ile Tyr Ser Met Asp Thr Glu
                260                 265                 270
Thr Leu Val Asp Ala Cys Trp Ala Ile Ser Tyr Leu Ser Asp Gly Pro
            275                 280                 285
Gln Glu Ala Ile Gln Ala Val Ile Asp Val Arg Ile Pro Lys Arg Leu
            290                 295                 300
Val Glu Leu Leu Ser His Glu Ser Thr Leu Val Gln Thr Pro Ala Leu
305                 310                 315                 320
Arg Ala Val Gly Asn Ile Val Thr Gly Asn Asp Leu Gln Thr Gln Val
                325                 330                 335
Val Ile Asn Ala Gly Val Leu Pro Ala Leu Arg Leu Leu Ser Ser
                340                 345                 350
Pro Lys Glu Asn Ile Lys Lys Glu Ala Cys Trp Thr Ile Ser Asn Ile
            355                 360                 365
Thr Ala Gly Asn Thr Glu Gln Ile Gln Ala Val Ile Asp Ala Asn Leu
            370                 375                 380
Ile Pro Pro Leu Val Lys Leu Leu Glu Val Ala Glu Tyr Lys Thr Lys
385                 390                 395                 400
Lys Glu Ala Cys Trp Ala Ile Ser Asn Ala Ser Ser Gly Gly Leu Gln
                405                 410                 415
Arg Pro Asp Ile Ile Arg Tyr Leu Val Ser Gln Gly Cys Ile Lys Pro
            420                 425                 430
```

-continued

```
Leu Cys Asp Leu Leu Glu Ile Ala Asp Asn Arg Ile Ile Glu Val Thr
        435                 440                 445

Leu Asp Ala Leu Glu Asn Ile Leu Lys Met Gly Glu Ala Asp Lys Glu
450                 455                 460

Ala Arg Gly Leu Asn Ile Asn Glu Asn Ala Asp Phe Ile Glu Lys Ala
465                 470                 475                 480

Gly Gly Met Glu Lys Ile Phe Asn Cys Gln Gln Asn Glu Asn Asp Lys
                485                 490                 495

Ile Tyr Glu Lys Ala Tyr Lys Ile Ile Glu Thr Tyr Phe Gly Glu Glu
                500                 505                 510

Glu Asp Ala Val Asp Glu Thr Met Ala Pro Gln Asn Ala Gly Asn Thr
            515                 520                 525

Phe Gly Phe Gly Ser Asn Val Asn Gln Gln Phe Asn Phe Asn
530                 535                 540
```

(2) INFORMATION FOR SEQ ID NO:13:

(i) SEQUENCE CHARACTERISTICS:
        (A) LENGTH: 170 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:13:

```
GGAGGCACCG AAGGGCAGCG CCGAGTCGGA GGGGGCGAAG ATTGACGCCA GTAAGAACGA      60

GGAGGATGAA GGCCATTCAA ACTCCTCCCC ACGACACTCT GAAGCAGCGA CGGCACAGCG     120

GGAAGAATGG AAAATGTTTA TAGGAGGCCT TAGCTGGGAC ACTACAAAGA                170
```

(2) INFORMATION FOR SEQ ID NO:14:

(i) SEQUENCE CHARACTERISTICS:
        (A) LENGTH: 1827 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..1362

(xi) SEQUENCE DESCRIPTION: SEQ ID NO:14:

```
GAG GTC AAT GTG GAG CTG AGG AAA GCT AAG AAG GAT GAC CAG ATG CTG       48
Glu Val Asn Val Glu Leu Arg Lys Ala Lys Lys Asp Asp Gln Met Leu
1               5                   10                  15

AAG AGG AGA AAT GTA AGC TCA TTT CCT GAT GAT GCT ACT TCT CCG CTG       96
Lys Arg Arg Asn Val Ser Ser Phe Pro Asp Asp Ala Thr Ser Pro Leu
            20                  25                  30

CAG GAA AAC CGC AAC AAC CAG GGC ACT GTA AAT TGG TCT GTT GAT GAC      144
Gln Glu Asn Arg Asn Asn Gln Gly Thr Val Asn Trp Ser Val Asp Asp
        35                  40                  45

ATT GTC AAA GGC ATA AAT AGC AGC AAT GTG GAA AAT CAG CTC CAA GCT      192
Ile Val Lys Gly Ile Asn Ser Ser Asn Val Glu Asn Gln Leu Gln Ala
50                  55                  60

ACT CAA GCT GCC AGG AAA CTA CTT TCC AGA GAA AAA CAG CCC CCC ATA      240
Thr Gln Ala Ala Arg Lys Leu Leu Ser Arg Glu Lys Gln Pro Pro Ile
65                  70                  75                  80

GAC AAC ATA ATC CGG GCT GGT TTG ATT CCG AAA TTT GTG TCC TTC TTG      288
Asp Asn Ile Ile Arg Ala Gly Leu Ile Pro Lys Phe Val Ser Phe Leu
```

```
                85                     90                     95
GGC AGA ACT GAT TGT AGT CCC ATT CAG TTT GAA TCT GCT TGG GCA CTC              336
Gly Arg Thr Asp Cys Ser Pro Ile Gln Phe Glu Ser Ala Trp Ala Leu
            100                 105                 110

ACT AAC ATT GCT TCT GGG ACA TCA GAA CAA ACC AAG GCT GTG GTA GAT              384
Thr Asn Ile Ala Ser Gly Thr Ser Glu Gln Thr Lys Ala Val Val Asp
            115                 120                 125

GGA GGT GCC ATC CCA GCA TTC ATT TCT CTG TTG GCA TCT CCC CAT GCT              432
Gly Gly Ala Ile Pro Ala Phe Ile Ser Leu Leu Ala Ser Pro His Ala
        130                 135                 140

CAC ATC AGT GAA CAA GCT GTC TGG GCT CTA GGA AAC ATT GCA GGT GAT              480
His Ile Ser Glu Gln Ala Val Trp Ala Leu Gly Asn Ile Ala Gly Asp
145                 150                 155                 160

GGC TCA GTG TTC CGA GAC TTG GTT ATT AAG TAC GGT GCA GTT GAC CCA              528
Gly Ser Val Phe Arg Asp Leu Val Ile Lys Tyr Gly Ala Val Asp Pro
                165                 170                 175

CTG TTG GCT CTC CTT GCA GTT CCT GAT ATG TCA TCT TTA GCA TGT GGC              576
Leu Leu Ala Leu Leu Ala Val Pro Asp Met Ser Ser Leu Ala Cys Gly
            180                 185                 190

TAC TTA CGT AAT CTT ACC TGG ACA CTT TCT AAT CTT TGC CGC AAC AAG              624
Tyr Leu Arg Asn Leu Thr Trp Thr Leu Ser Asn Leu Cys Arg Asn Lys
            195                 200                 205

AAT CCT GCA CCC CCG ATA GAT GCT GTT GAG CAG ATT CTT CCT ACC TTA              672
Asn Pro Ala Pro Pro Ile Asp Ala Val Glu Gln Ile Leu Pro Thr Leu
        210                 215                 220

GTT CGG CTC CTG CAT CAT GAT GAT CCA GAA GTG TTA GCA GAT ACC TGC              720
Val Arg Leu Leu His His Asp Asp Pro Glu Val Leu Ala Asp Thr Cys
225                 230                 235                 240

TGG GCT ATT TCC TAC CTT ACT GAT GGT CCA AAT GAA CGA ATT GGC ATG              768
Trp Ala Ile Ser Tyr Leu Thr Asp Gly Pro Asn Glu Arg Ile Gly Met
                245                 250                 255

GTG GTG AAA ACA GGA GTT GTG CCC CAA CTT GTG AAG CTT CTA GGA GCT              816
Val Val Lys Thr Gly Val Val Pro Gln Leu Val Lys Leu Leu Gly Ala
            260                 265                 270

TCT GAA TTG CCA ATT GTG ACT CCT GCC CTA AGA GCC ATA GGG AAT ATT              864
Ser Glu Leu Pro Ile Val Thr Pro Ala Leu Arg Ala Ile Gly Asn Ile
            275                 280                 285

GTC ACT GGT ACA GAT GAA CAG ACT CAG GTT GTG ATT GAT GCA GGA GCA              912
Val Thr Gly Thr Asp Glu Gln Thr Gln Val Val Ile Asp Ala Gly Ala
        290                 295                 300

CTC GCC GTC TTT CCC AGC CTG CTC ACC AAC CCC AAA ACT AAC ATT CAG              960
Leu Ala Val Phe Pro Ser Leu Leu Thr Asn Pro Lys Thr Asn Ile Gln
305                 310                 315                 320

AAG GAA GCT ACG TGG ACA ATG TCA AAC ATC ACA GCC GGC CGC CAG GAC             1008
Lys Glu Ala Thr Trp Thr Met Ser Asn Ile Thr Ala Gly Arg Gln Asp
                325                 330                 335

CAG ATA CAG CAA GTT GTG AAT CAT GGA TTA GTC CCA TTC CTT GTC AGT             1056
Gln Ile Gln Gln Val Val Asn His Gly Leu Val Pro Phe Leu Val Ser
            340                 345                 350

GTT CTC TCT AAG GCA GAT TTT AAG ACA CAA AAG GAA GCT GTG TGG GCC             1104
Val Leu Ser Lys Ala Asp Phe Lys Thr Gln Lys Glu Ala Val Trp Ala
            355                 360                 365

GTG ACC AAC TAT ACC AGT GGT GGA ACA GTT GAA CAG ATT GTG TAC CTT             1152
Val Thr Asn Tyr Thr Ser Gly Gly Thr Val Glu Gln Ile Val Tyr Leu
        370                 375                 380

GTT CAC TGT GGC ATA ATA GAA CCG TTG ATG AAC CTC TTA ACT GCA AAA             1200
Val His Cys Gly Ile Ile Glu Pro Leu Met Asn Leu Leu Thr Ala Lys
385                 390                 395                 400

GAT ACC AAG ATT ATT CTG GTT ATC CTG GAT GCC ATT TCA AAT ATC TTT             1248
Asp Thr Lys Ile Ile Leu Val Ile Leu Asp Ala Ile Ser Asn Ile Phe
```

-continued

```
Asp Thr Lys Ile Ile Leu Val Ile Leu Asp Ala Ile Ser Asn Ile Phe
            405                 410                 415
CAG GCT GCT GAG AAA CTA GGT GAA ACT AGC TGC CCG TCT TCA CAG ATT      1296
Gln Ala Ala Glu Lys Leu Gly Glu Thr Ser Cys Pro Ser Ser Gln Ile
        420                 425                 430
CAA GAA CAA GGG AAA AGA CAG TAC AGA AAT GAG GCG TCC GAG GCG TCG      1344
Gln Glu Gln Gly Lys Arg Gln Tyr Arg Asn Glu Ala Ser Glu Ala Ser
                435                 440                 445
CAG AAT AGA GAA ACT TAG TATAATGATT GAAGAATGTG GAGGCTTAGA             1392
Gln Asn Arg Glu Thr  *
        450

CAAAATTGAA GCTCTACAAA ACCATGAAAA TGAGTCTGTG TATAAGGCTT CGTTAAGCTT    1452

AATTGAGAAG TATTTCTCTG TAGAGGAAGA GGAAGATCAA AACGTTGTAC CAGAAACTAC    1512

CTCTGAAGGC TACACTTTCC AAGTTCAGGA TGGGGCTCCT GGGACCTTTA ACTTTTAGAT    1572

CATGTAGCTG AGACATAAAT TGTTGTGTA CTACGTTTGG TATTTTGTCT TATTGTTTCT     1632

CTACTAAGAA CTCTTTCTTA AATGTGGTTT GTTACTGTAG CACTTTTTAC ACTGAAACTA    1692

TACTTGAACA GTTCCAACTG TACATACATA CTGTATGAAG CTTGTCCTCT GACTAGGTTT    1752

CTAATTTCTA TGTGGAATTT CCTATCTTGC AGCATCCTGT AAATAAACAT TCAAGTCCAC    1812

CCTTTTCTTG ACTTC                                                    1827
```

(2) INFORMATION FOR SEQ ID NO:15:

(i) SEQUENCE CHARACTERISTICS:
        (A) LENGTH: 453 amino acids
        (B) TYPE: amino acid
        (D) TOPOLOGY: linear (ii) MOLECULE TYPE: protein (xi) SEQUENCE DESCRIPTION: SEQ ID NO:15:

```
Glu Val Asn Val Glu Leu Arg Lys Ala Lys Lys Asp Asp Gln Met Leu
 1               5                  10                  15

Lys Arg Arg Asn Val Ser Ser Phe Pro Asp Asp Ala Thr Ser Pro Leu
            20                  25                  30

Gln Glu Asn Arg Asn Asn Gln Gly Thr Val Asn Trp Ser Val Asp Asp
        35                  40                  45

Ile Val Lys Gly Ile Asn Ser Ser Asn Val Glu Asn Gln Leu Gln Ala
    50                  55                  60

Thr Gln Ala Ala Arg Lys Leu Leu Ser Arg Glu Lys Gln Pro Pro Ile
65                  70                  75                  80

Asp Asn Ile Ile Arg Ala Gly Leu Ile Pro Lys Phe Val Ser Phe Leu
                85                  90                  95

Gly Arg Thr Asp Cys Ser Pro Ile Gln Phe Glu Ser Ala Trp Ala Leu
            100                 105                 110

Thr Asn Ile Ala Ser Gly Thr Ser Glu Gln Thr Lys Ala Val Val Asp
        115                 120                 125

Gly Gly Ala Ile Pro Ala Phe Ile Ser Leu Leu Ala Ser Pro His Ala
    130                 135                 140

His Ile Ser Glu Gln Ala Val Trp Ala Leu Gly Asn Ile Ala Gly Asp
145                 150                 155                 160

Gly Ser Val Phe Arg Asp Leu Val Ile Lys Tyr Gly Ala Val Asp Pro
                165                 170                 175

Leu Leu Ala Leu Leu Ala Val Pro Asp Met Ser Ser Leu Ala Cys Gly
            180                 185                 190
```

-continued

```
Tyr Leu Arg Asn Leu Thr Trp Thr Leu Ser Asn Leu Cys Arg Asn Lys
            195                 200                 205
Asn Pro Ala Pro Pro Ile Asp Ala Val Glu Gln Ile Leu Pro Thr Leu
    210                 215                 220
Val Arg Leu Leu His His Asp Asp Pro Glu Val Leu Ala Asp Thr Cys
225                 230                 235                 240
Trp Ala Ile Ser Tyr Leu Thr Asp Gly Pro Asn Glu Arg Ile Gly Met
                245                 250                 255
Val Val Lys Thr Gly Val Val Pro Gln Leu Val Lys Leu Leu Gly Ala
                260                 265                 270
Ser Glu Leu Pro Ile Val Thr Pro Ala Leu Arg Ala Ile Gly Asn Ile
                275                 280                 285
Val Thr Gly Thr Asp Glu Gln Thr Gln Val Val Ile Asp Ala Gly Ala
            290                 295                 300
Leu Ala Val Phe Pro Ser Leu Leu Thr Asn Pro Lys Thr Asn Ile Gln
305                 310                 315                 320
Lys Glu Ala Thr Trp Thr Met Ser Asn Ile Thr Ala Gly Arg Gln Asp
                325                 330                 335
Gln Ile Gln Gln Val Val Asn His Gly Leu Val Pro Phe Leu Val Ser
            340                 345                 350
Val Leu Ser Lys Ala Asp Phe Lys Thr Gln Lys Glu Ala Val Trp Ala
        355                 360                 365
Val Thr Asn Tyr Thr Ser Gly Gly Thr Val Glu Gln Ile Val Tyr Leu
    370                 375                 380
Val His Cys Gly Ile Ile Glu Pro Leu Met Asn Leu Leu Thr Ala Lys
385                 390                 395                 400
Asp Thr Lys Ile Ile Leu Val Ile Leu Asp Ala Ile Ser Asn Ile Phe
                405                 410                 415
Gln Ala Ala Glu Lys Leu Gly Glu Thr Ser Cys Pro Ser Ser Gln Ile
            420                 425                 430
Gln Glu Gln Gly Lys Arg Gln Tyr Arg Asn Glu Ala Ser Glu Ala Ser
        435                 440                 445
Gln Asn Arg Glu Thr
450
```

(2) INFORMATION FOR SEQ ID NO:16:

(i) SEQUENCE CHARACTERISTICS:
        (A) LENGTH: 259 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:16:

```
GAACGACCAA GAGGGTGTTC GACTGCTAGA GCCGAGCAGA AGCGTGCCTA AATCAAAGGA      60

ACTTGTTTCT TCAAGCTCTT CTGGCAGTGA TTCTGACAGT GAGGTTGACA AAAAGTTAAG     120

CAGGAAAAAG CAAGTTGCTC CAGAAAAACC TGTAAAGAAA CAAAAGACAG GTGAGACTTC     180

GAGAGCCCTG TCATCTTCTA AACAGAGCAG CAGCAGCAGA GATGATAACA TGTTTCAGAT     240

TGGGAAAATG AGGTCAGTT                                                  259
```

(2) INFORMATION FOR SEQ ID NO:17:

(i) SEQUENCE CHARACTERISTICS:
        (A) LENGTH: 221 base pairs (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:17:

```
TGTCGACTGT GGCTTTGAGC ATCCGTCAGA AGTCCAGCAT GAGTGCATCC CTCAGGCCAT      60

TCTGGGAATG GATGTCCTGT GCCAGGCCAA GTCGGGCATG GGAAAGACAG CAGTGTTTGT     120

CTTGGCCACA CTGCAACAGC TGGAGCCAGT TACTGGGCAG GTGTCTGTAC TGGTGATGTG     180

TCACACTCGG GAGTTGGCTT TTCAGATCAG CAAGGAATAT G                         221
```

(2) INFORMATION FOR SEQ ID NO:18:

(i) SEQUENCE CHARACTERISTICS:
        (A) LENGTH: 372 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:18:

```
ATTTGTAAAC CCCGGAGCGA GGTTCTGCTT ACCCGAGGCC GCTGCTGTGC GGAGACCCCC      60

GGGTGAAGCC ACCGTCATCA TGTCTGACCA GGAGGCAAAA CCTTCAACTG AGGACTTGGG     120

GGATAAGAAG GAAGGTGAAT ATATTAAACT CAAAGTCATT GGACAGGATA GCAGTGAGAT     180

TCACTTCAAA GTGAAAATGA CAACACATCT CAAGAAACTC AAAGAATCAT ACTGTCAAAG     240

ACAGGGTGTT CCAATGAATT CACTCAGGTT TCTCTTTGAG GGTCAGAGAA TTGCTGATAA     300

TCATACTCCA AAAGAACTGG GAATGGAGGA AGAAGTTGTG ATTGAAGTTT ATCAGGAACA     360

AACGGGGGGT CA                                                         372
```

(2) INFORMATION FOR SEQ ID NO:19:

(i) SEQUENCE CHARACTERISTICS:
        (A) LENGTH: 2675 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 104..2311

(xi) SEQUENCE DESCRIPTION: SEQ ID NO:19:

```
TCTGACCCTC GTCCCGCCCC CGCCATTCGC CGCCTCCTCC TGTCCCGCAG TCGGCGTCCA                 60

GCGGCTCTGC TTGTTCGTGT GTGTGTCGTT GCAGGCCTTA TTC ATG GGC TCA CCG               115
                                                Met Gly Ser Pro
                                                    1

CTG AGG TTC GAC GGG CGG GTG GTA CTG GTC ACC GGC GCG GGG GCA GGA               163
Leu Arg Phe Asp Gly Arg Val Val Leu Val Thr Gly Ala Gly Ala Gly
  5                  10                  15                  20

TTG GGC CGA GCC TAT GCC CTG GCT TTT GCA GAA AGA GGA GCG TTA GTT               211
Leu Gly Arg Ala Tyr Ala Leu Ala Phe Ala Glu Arg Gly Ala Leu Val
             25                  30                  35

GTT GTG AAT GAT TTG GGA GGG GAC TTC AAA GGA GTT GGT AAA GGC TCC               259
Val Val Asn Asp Leu Gly Gly Asp Phe Lys Gly Val Gly Lys Gly Ser
         40                  45                  50

TTA GCT GAT AAG GTT GTT GAA GAA ATA AGA AGG AGA GGT GGA AAA GCA               307
```

```
                Leu Ala Asp Lys Val Val Glu Ile Arg Arg Gly Gly Lys Ala
                         55                  60                  65

GTG GCC AAC TAT GAT TCA GTG GAA GAA GGA GAG AAG GTT GTG AAG ACA         355
Val Ala Asn Tyr Asp Ser Val Glu Glu Gly Glu Lys Val Val Lys Thr
         70                  75                  80

GCC CTG GAT GCT TTT GGA AGA ATA GAT GTT GTG GTC AAC AAT GCT GGA         403
Ala Leu Asp Ala Phe Gly Arg Ile Asp Val Val Val Asn Asn Ala Gly
85                  90                  95                 100

ATT CTG AGG GAT CAT TCC TTT GCT AGG ATA AGT GAT GAA GAC TGG GAT         451
Ile Leu Arg Asp His Ser Phe Ala Arg Ile Ser Asp Glu Asp Trp Asp
                        105                 110                 115

ATA ATC CAC AGA GTT CAT TTG CGG GGT TCA TTC CAA GTG ACA CGG GCA         499
Ile Ile His Arg Val His Leu Arg Gly Ser Phe Gln Val Thr Arg Ala
                    120                 125                 130

GCA TGG GAA CAC ATG AAG AAA CAG AAG TAT GGA AGG ATT ATT ATG ACT         547
Ala Trp Glu His Met Lys Lys Gln Lys Tyr Gly Arg Ile Ile Met Thr
                135                 140                 145

TCA TCA GCT TCA GGA ATA TAT GGC AAC TTT GGC CAG GCC AAT TAT AGT         595
Ser Ser Ala Ser Gly Ile Tyr Gly Asn Phe Gly Gln Ala Asn Tyr Ser
            150                 155                 160

GCT GCA AAG TTG GGT CTT CTG GGC CTT GCA AAT TCT CTT GCA ATT GAA         643
Ala Ala Lys Leu Gly Leu Leu Gly Leu Ala Asn Ser Leu Ala Ile Glu
165                 170                 175                 180

GGC AGG AAA AGC AAC ATT CAT TGT AAC ACC ATT GCT CCT AAT GCG GGA         691
Gly Arg Lys Ser Asn Ile His Cys Asn Thr Ile Ala Pro Asn Ala Gly
                        185                 190                 195

TCA CGG ATG ACT CAG ACA GTT ATG CCT GAA GAT CTT GTG GAA GCC TTG         739
Ser Arg Met Thr Gln Thr Val Met Pro Glu Asp Leu Val Glu Ala Leu
                    200                 205                 210

AAG CCA GAG TAT GTG GCA CCT CTT GTC CTT TGG CTT TGT CAC GAG AGT         787
Lys Pro Glu Tyr Val Ala Pro Leu Val Leu Trp Leu Cys His Glu Ser
                215                 220                 225

TGT GAG GAG AAT GGT GGC TTG TTT GAG GTT GGT GCA GGA TGG ATT GGA         835
Cys Glu Glu Asn Gly Gly Leu Phe Glu Val Gly Ala Gly Trp Ile Gly
            230                 235                 240

AAA TTA CGC TGG GAG CGG ACT CTT GGA GCT ATT GTA AGA CAA AAG AAT         883
Lys Leu Arg Trp Glu Arg Thr Leu Gly Ala Ile Val Arg Gln Lys Asn
245                 250                 255                 260

CAC CCA ATG ACT CCT GAG GCA GTC AAG GCT AAC TGG AAG AAG ATC TGT         931
His Pro Met Thr Pro Glu Ala Val Lys Ala Asn Trp Lys Lys Ile Cys
                        265                 270                 275

GAC TTT GAG AAT GCC AGC AAG CCT CAG AGT ATC CAA GAA TCA ACT GGC         979
Asp Phe Glu Asn Ala Ser Lys Pro Gln Ser Ile Gln Glu Ser Thr Gly
                    280                 285                 290

AGT ATA ATT GAA GTT CTG AGT AAA ATA GAT TCA GAA GGA GGT GTT TCA         1027
Ser Ile Ile Glu Val Leu Ser Lys Ile Asp Ser Glu Gly Gly Val Ser
                295                 300                 305

GCA AAT CAT ACT AGT CGT GCA ACG TCT ACA GCA ACA TCA GGA TTT GCT         1075
Ala Asn His Thr Ser Arg Ala Thr Ser Thr Ala Thr Ser Gly Phe Ala
            310                 315                 320

GGA GCT ATT GGC CAG AAA CTC CCT CCA TTT TCT TAT GCT TAT ACG GAA         1123
Gly Ala Ile Gly Gln Lys Leu Pro Pro Phe Ser Tyr Ala Tyr Thr Glu
325                 330                 335                 340

CTG GAA GCT ATT ATG TAT GCC CTT GGA GTG GGA GCG TCA ATC AAG GAT         1171
Leu Glu Ala Ile Met Tyr Ala Leu Gly Val Gly Ala Ser Ile Lys Asp
                        345                 350                 355

CCA AAA GAT TTG AAA TTT ATT TAT GAA GGA AGT TCT GAT TTC TCC TGT         1219
Pro Lys Asp Leu Lys Phe Ile Tyr Glu Gly Ser Ser Asp Phe Ser Cys
                    360                 365                 370
```

-continued

```
TTG CCC ACC TTC GGA GTT ATC ATA GGT CAG AAA TCT ATG ATG GGT GGA      1267
Leu Pro Thr Phe Gly Val Ile Ile Gly Gln Lys Ser Met Met Gly Gly
        375                 380                 385

GGA TTA GCA GAA ATT CCT GGA CTT TCA ATC AAC TTT GCA AAG GTT CTT      1315
Gly Leu Ala Glu Ile Pro Gly Leu Ser Ile Asn Phe Ala Lys Val Leu
        390                 395                 400

CAT GGA GAG CAG TAC TTA GAG TTA TAT AAA CCA CTT CCC AGA GCA GGA      1363
His Gly Glu Gln Tyr Leu Glu Leu Tyr Lys Pro Leu Pro Arg Ala Gly
405                 410                 415                 420

AAA TTA AAA TGT GAA GCA GTT GTT GCT GAT GTC CTA GAT AAA GGA TCC      1411
Lys Leu Lys Cys Glu Ala Val Val Ala Asp Val Leu Asp Lys Gly Ser
                    425                 430                 435

GGT GTA GTG ATT ATT ATG GAT GTC TAT TCT TAT TCT GAG AAG GAA CTT      1459
Gly Val Val Ile Ile Met Asp Val Tyr Ser Tyr Ser Glu Lys Glu Leu
                440                 445                 450

ATA TGC CAC AAT CAG TTC TCT CTC TTT CTT GTT GGC TCT GGA GGC TTT      1507
Ile Cys His Asn Gln Phe Ser Leu Phe Leu Val Gly Ser Gly Gly Phe
            455                 460                 465

GGT GGA AAA CGG ACA TCA GAC AAA GTC AAG GTA GCT GTA GCC ATA CCT      1555
Gly Gly Lys Arg Thr Ser Asp Lys Val Lys Val Ala Val Ala Ile Pro
        470                 475                 480

AAT AGA CCT CCT GAT GCT GTA CTT ACA GAT ACC ACC TCT CTT AAT CAG      1603
Asn Arg Pro Pro Asp Ala Val Leu Thr Asp Thr Thr Ser Leu Asn Gln
485                 490                 495                 500

GCT GCT TTG TAC CGC CTC AGT GGA GAC CGG AAT CCC TTA CAC ATT GAT      1651
Ala Ala Leu Tyr Arg Leu Ser Gly Asp Arg Asn Pro Leu His Ile Asp
                    505                 510                 515

CCT AAC TTT GCT AGT CTA GCA GGT TTT GAC AAG CCC ATA TTA CAT GGA      1699
Pro Asn Phe Ala Ser Leu Ala Gly Phe Asp Lys Pro Ile Leu His Gly
                520                 525                 530

TTA TGT ACA TTT GGA TTT TCT GCC AGG CGT GTG TTA CAG CAG TTT GCA      1747
Leu Cys Thr Phe Gly Phe Ser Ala Arg Arg Val Leu Gln Gln Phe Ala
            535                 540                 545

GAT AAT GAT GTG TCA AGA TTC AAG GCA GTT AAG GCT CGT TTT GCA AAA      1795
Asp Asn Asp Val Ser Arg Phe Lys Ala Val Lys Ala Arg Phe Ala Lys
        550                 555                 560

CCA GTA TAT CCA GGA CAA ACT CTA CAA ACT GAG ATG TGG AAG GAA GGA      1843
Pro Val Tyr Pro Gly Gln Thr Leu Gln Thr Glu Met Trp Lys Glu Gly
565                 570                 575                 580

AAC AGA ATT CAT TTT CAA ACC AAG GTC CAA GAA ACT GGA GAC ATT GTC      1891
Asn Arg Ile His Phe Gln Thr Lys Val Gln Glu Thr Gly Asp Ile Val
                    585                 590                 595

ATT TCA AAT GCA TAT GTG GAT CTT GCA CCA ACA TCT GGT ACT TCA GCT      1939
Ile Ser Asn Ala Tyr Val Asp Leu Ala Pro Thr Ser Gly Thr Ser Ala
                600                 605                 610

AAG ACA CCC TCT GAG GGC GGG AAG CTT CAG AGT ACC TTT GTA TTT GAG      1987
Lys Thr Pro Ser Glu Gly Gly Lys Leu Gln Ser Thr Phe Val Phe Glu
            615                 620                 625

GAA ATA GGA CGC CGC CTA AAG GAT ATT GGG CCT GAG GTG GTG AAG AAA      2035
Glu Ile Gly Arg Arg Leu Lys Asp Ile Gly Pro Glu Val Val Lys Lys
        630                 635                 640

GTA AAT GCT GTA TTT GAG TGG CAT ATA ACC AAA GGC GGA AAT ATT GGG      2083
Val Asn Ala Val Phe Glu Trp His Ile Thr Lys Gly Gly Asn Ile Gly
645                 650                 655                 660

GCT AAG TGG ACT ATT GAC CTG AAA AGT GGT TCT GGA AAA GTG TAC CAA      2131
Ala Lys Trp Thr Ile Asp Leu Lys Ser Gly Ser Gly Lys Val Tyr Gln
                    665                 670                 675

GGC CCT GCA AAA GGT GCT GCT GAT ACA ACA ATC ATA CTT TCA GAT GAA      2179
Gly Pro Ala Lys Gly Ala Ala Asp Thr Thr Ile Ile Leu Ser Asp Glu
                680                 685                 690
```

```
GAT TTC ATG GAG GTG GTC CTG GGC AAG CTT GAC CCT CAG AAG GCA TTC     2227
Asp Phe Met Glu Val Val Leu Gly Lys Leu Asp Pro Gln Lys Ala Phe
        695                 700                 705

TTT AGT GGC AGG CTG AAG GCC AGA GGG AAC ATC ATG CTG AGC CAG AAA     2275
Phe Ser Gly Arg Leu Lys Ala Arg Gly Asn Ile Met Leu Ser Gln Lys
    710                 715                 720

CTT CAG ATG ATT CTT AAA GAC TAC GCC AAG CTC TGA AGGGCACACT          2321
Leu Gln Met Ile Leu Lys Asp Tyr Ala Lys Leu  *
725                 730                 735

ACACTATTAA TAAAAATGGA ATCATTAAAT ACTCTCTTCA CCCAAATATG CTTGATTATT    2381

CTGCAAAAGT GATTAGAACT AAGATGCAGG GGAAATTGCT TAACATTTTC AGATATCAGA   2441

TAACTGCAGA TTTTCATTTT CTACTAATTT TTCATGTATC ATTATTTTTA CAAGGAACTA   2501

TATATAAGCT AGCACATAAT TATCCTTCTG TTCTTAGATC TGTATCTTCA TAATAAAAAA   2561

ATTTTGCCCA AGTCCTGTTT CCTTAGAATT TGTGATAGCA TTGATAAGTT GAAAGGAAAA   2621

TTAAATCAAT AAAGGCCTTT GATACCTTTA AAAAAAAAAA AAAAAAAAAA AAAA         2675

(2) INFORMATION FOR SEQ ID NO:20:

(i) SEQUENCE CHARACTERISTICS:
        (A) LENGTH:  735 amino acids
        (B) TYPE: amino acid
        (D) TOPOLOGY: linear (ii) MOLECULE TYPE: protein (xi) SEQUENCE DESCRIPTION: SEQ ID NO:20:

Met Gly Ser Pro Leu Arg Phe Asp Gly Arg Val Val Leu Val Thr Gly
 1               5                  10                  15

Ala Gly Ala Gly Leu Gly Arg Ala Tyr Ala Leu Ala Phe Ala Glu Arg
            20                  25                  30

Gly Ala Leu Val Val Val Asn Asp Leu Gly Gly Asp Phe Lys Gly Val
        35                  40                  45

Gly Lys Gly Ser Leu Ala Asp Lys Val Val Glu Glu Ile Arg Arg Arg
    50                  55                  60

Gly Gly Lys Ala Val Ala Asn Tyr Asp Ser Val Glu Glu Gly Glu Lys
65                  70                  75                  80

Val Val Lys Thr Ala Leu Asp Ala Phe Gly Arg Ile Asp Val Val Val
                85                  90                  95

Asn Asn Ala Gly Ile Leu Arg Asp His Ser Phe Ala Arg Ile Ser Asp
            100                 105                 110

Glu Asp Trp Asp Ile Ile His Arg Val His Leu Arg Gly Ser Phe Gln
        115                 120                 125

Val Thr Arg Ala Ala Trp Glu His Met Lys Lys Gln Lys Tyr Gly Arg
    130                 135                 140

Ile Ile Met Thr Ser Ser Ala Ser Gly Ile Tyr Gly Asn Phe Gly Gln
145                 150                 155                 160

Ala Asn Tyr Ser Ala Ala Lys Leu Gly Leu Leu Gly Leu Ala Asn Ser
                165                 170                 175

Leu Ala Ile Glu Gly Arg Lys Ser Asn Ile His Cys Asn Thr Ile Ala
            180                 185                 190

Pro Asn Ala Gly Ser Arg Met Thr Gln Thr Val Met Pro Glu Asp Leu
        195                 200                 205

Val Glu Ala Leu Lys Pro Glu Tyr Val Ala Pro Leu Val Leu Trp Leu
    210                 215                 220
```

```
Cys His Glu Ser Cys Glu Asn Gly Gly Leu Phe Glu Val Gly Ala
225                 230                 235                 240

Gly Trp Ile Gly Lys Leu Arg Trp Glu Arg Thr Leu Gly Ala Ile Val
            245                 250                 255

Arg Gln Lys Asn His Pro Met Thr Pro Glu Ala Val Lys Ala Asn Trp
                260                 265                 270

Lys Lys Ile Cys Asp Phe Glu Asn Ala Ser Lys Pro Gln Ser Ile Gln
            275                 280                 285

Glu Ser Thr Gly Ser Ile Ile Glu Val Leu Ser Lys Ile Asp Ser Glu
        290                 295                 300

Gly Gly Val Ser Ala Asn His Thr Ser Arg Ala Thr Ser Thr Ala Thr
305                 310                 315                 320

Ser Gly Phe Ala Gly Ala Ile Gly Gln Lys Leu Pro Pro Phe Ser Tyr
                325                 330                 335

Ala Tyr Thr Glu Leu Glu Ala Ile Met Tyr Ala Leu Gly Val Gly Ala
            340                 345                 350

Ser Ile Lys Asp Pro Lys Asp Leu Lys Phe Ile Tyr Glu Gly Ser Ser
        355                 360                 365

Asp Phe Ser Cys Leu Pro Thr Phe Gly Val Ile Gly Gln Lys Ser
370                 375                 380

Met Met Gly Gly Leu Ala Glu Ile Pro Gly Leu Ser Ile Asn Phe
385                 390                 395                 400

Ala Lys Val Leu His Gly Glu Gln Tyr Leu Glu Leu Tyr Lys Pro Leu
                405                 410                 415

Pro Arg Ala Gly Lys Leu Lys Cys Glu Ala Val Val Ala Asp Val Leu
            420                 425                 430

Asp Lys Gly Ser Gly Val Val Ile Ile Met Asp Val Tyr Ser Tyr Ser
        435                 440                 445

Glu Lys Glu Leu Ile Cys His Asn Gln Phe Ser Leu Phe Leu Val Gly
        450                 455                 460

Ser Gly Gly Phe Gly Gly Lys Arg Thr Ser Asp Lys Val Lys Val Ala
465                 470                 475                 480

Val Ala Ile Pro Asn Arg Pro Pro Asp Ala Val Leu Thr Asp Thr Thr
                485                 490                 495

Ser Leu Asn Gln Ala Ala Leu Tyr Arg Leu Ser Gly Asp Arg Asn Pro
        500                 505                 510

Leu His Ile Asp Pro Asn Phe Ala Ser Leu Ala Gly Phe Asp Lys Pro
        515                 520                 525

Ile Leu His Gly Leu Cys Thr Phe Gly Phe Ser Ala Arg Arg Val Leu
        530                 535                 540

Gln Gln Phe Ala Asp Asn Asp Val Ser Arg Phe Lys Ala Val Lys Ala
545                 550                 555                 560

Arg Phe Ala Lys Pro Val Tyr Pro Gly Gln Thr Leu Gln Thr Glu Met
                565                 570                 575

Trp Lys Glu Gly Asn Arg Ile His Phe Gln Thr Lys Val Gln Glu Thr
            580                 585                 590

Gly Asp Ile Val Ile Ser Asn Ala Tyr Val Asp Leu Ala Pro Thr Ser
        595                 600                 605

Gly Thr Ser Ala Lys Thr Pro Ser Glu Gly Gly Lys Leu Gln Ser Thr
        610                 615                 620

Phe Val Phe Glu Glu Ile Gly Arg Arg Leu Lys Asp Ile Gly Pro Glu
625                 630                 635                 640

Val Val Lys Lys Val Asn Ala Val Phe Glu Trp His Ile Thr Lys Gly
```

-continued

```
                        645                    650                    655
Gly Asn Ile Gly Ala Lys Trp Thr Ile Asp Leu Lys Ser Gly Ser Gly
                660                    665                    670

Lys Val Tyr Gln Gly Pro Ala Lys Gly Ala Ala Asp Thr Thr Ile Ile
            675                    680                    685

Leu Ser Asp Glu Asp Phe Met Glu Val Val Leu Gly Lys Leu Asp Pro
        690                    695                    700

Gln Lys Ala Phe Phe Ser Gly Arg Leu Lys Ala Arg Gly Asn Ile Met
705                    710                    715                    720

Leu Ser Gln Lys Leu Gln Met Ile Leu Lys Asp Tyr Ala Lys Leu
                725                    730                    735
```

IDENTIFICATION AND USE OF ANTIVIRAL COMPOUNDS THAT INHIBIT INTERACTION OF HOST CELL PROTEINS AND VIRAL PROTEINS REQUIRED FOR VIRAL REPLICATION

This application is a continuation-in-part of application Ser. No. 08/246,583, filed May 20, 1994 now U.S. Pat. No. 5,750,394, which is hereby incorporated by reference in its entirety.

1. INTRODUCTION

The present invention relates to the identification of new cellular targets for viral intervention, the identification of antiviral compounds that act on the new targets, and the therapeutic use of such antiviral compounds.

2. BACKGROUND OF THE INVENTION

Influenza A virus is a negative strand RNA virus belonging to the orthomyxovirus family. The genome of the virus consists of 8 segments and encodes 10 polypeptides. Experimental evidence generated in the laboratory of Scholtissek indicates that the nucleoprotein (NP) is a major determinant of species specificity of influenza viruses (Scholtissek, et al., 1985, Virology 147: 287–294). Phylogenetic analysis divides NP genes into two families: one containing NPs predominantly of avian origin, and one containing those of human origin (Bean, 1984, Virology 133:438–442; Buckler-White & Murphy, 1986, Virology 155: 345–355; Gammelin, et al., 1989, Virology 170:71–80; Scholtissek, et al., 1985, supra). The human virus A/HK/1/68 and viruses having genetically related NPs cannot rescue mutants of the avian virus A/FPV/Rostock/1/34 with ts defects in the NP following double infection of chicken embryo fibroblasts (CEF) at 40° C. (Scholtissek, et al., 1985, supra; Scholtissek, et al., 1978, Virology 91: 79–85). However, the human viruses which failed to rescue the ts mutants on CEF cells were able to do so on Madin-Darby canine kidney(MDCK) cells (Scholtissek, et al., 1978, supra). Additionally, A/HK/1/68 virus and A/FPV/Rostock/1/34 virus reassortants containing the A/HK/1/68 virus-derived NP replicate in MDBK cells but not in CEFs (Scholtissek, et al., 1978, supra). The host-specific rescue of FPV ts mutants and the host restriction of A/HK/1/68 virus reassortants suggest that a factor(s) of host origin, which differs between mammalian and avian cells, is responsible for this phenomenon, and that this factor may interact with the influenza A virus NP. However, heretofore, no host protein has been identified.

Replication and transcription of influenza virus RNA requires four virus encoded proteins: the NP and the three components of the viral RNA-dependent RNA polymerase, PB1, PB2 and PA (Huang, et al., 1990, J. Virol. 64: 5669–5673). The NP is the major structural component of the virion which interacts with genomic RNA, and is required for antitermination during RNA synthesis (Beaton & Krug, 1986, Proc. Natl. Acad. Sci. USA 83:6282–6286). NP is also required for elongation of RNA chains (Shapiro & Krug, 1988, J. Virol. 62: 2285–2290) but not for initiation (Honda, et al., 1988, J. Biochem. 104: 1021–1026).

NS1 is a major non-structural protein expressed by influenza A viruses in infected cells, whose role in infection is not clear. Studies of viruses carrying temperature-sensitive NS1 alleles point to a regulatory role for NS1 in viral gene-expression and/or replication (Wolstenholme, et al., 1980, J. Virol. 35:1–7; Koennecke, et al., 1981, Virol. 110:16–25; Hatada, et al., 1990, J. Gen. Virol. 71: 1283–1292), which is also consistent with its preferentially nuclear accumulation (Greenspan, et al., 1988, J. Virol. 62: 3020–3026). Its expression has been shown to interfere with cellular functions in a variety of ways. (Fortes, et al., 1994, EMBO J. 13: 704–712; Qiu & Krug, 1994, J. Virol. 68: 2425–2432; Lu, et al., 1994, Genes Dev. 8: 1817–1828). These effects have been suggested to be mediated through NS1's observed interactions with a variety of RNA's, including single- and double-stranded influenza vRNA (Hatada & Fukuda, 1992, J. Gen. Virol. 73: 3325–3329; Hatada, et al., 1992, J. Gen Virol. 73: 17–25), poly-adenosine RNA (Qiu & Krug, 1994, supra), and spliceosomal U6 RNA (Lu, et al., 1994, supra). Despite these studies involving the interaction of NS1 with various RNAs, no host proteins that interact with NS1 during infection have previously been identified or characterized.

Little is known about host cell functions which contribute to the intracellular replication of influenza viruses, and cellular factors have not been characterized which directly interact with the viral proteins, much less cellular factor/viral interactions that can be used as targets for therapeutic intervention.

3. SUMMARY OF THE INVENTION

The present invention relates to the identification of host cell proteins that interact with viral proteins required for virus replication, and high throughput assays to identify compounds that interfere with the specific interaction between the viral and host cell protein. Interfering compounds that inhibit viral replication can be used therapeutically to treat viral infection.

The invention is based, in part, on the Applicants' discovery of a novel interaction between influenza viral proteins, such as NP and NS1, and human host cell proteins referred to herein as NPI-1, NPI-2, NPI-3, NPI-4, NPI-5, NPI-6, and NS1I-1, respectively. The host cell proteins such as NPI-1 and NS1I-1 may be accessory proteins required for replication of influenza virus. Compounds that interfere with the binding of the host cell and viral proteins and inhibit viral replication can be useful for treating viral infection in vivo.

4. DESCRIPTION OF THE FIGURES

FIGS. 1A and 1B: The interactive trap system, as used in the identification of NP-interacting proteins. FIG. 1A: R100 contains the reporter gene LexAop-LEU2 and a transcriptionally inactive LexA-NP fusion protein (left). Library proteins are synthesized in R100 transformants in media containing galactose. If the library protein does not interact with the LexA-NP fusion protein, then the LEU2 gene is not transcribed (middle). If the library protein does interact with the LexA-NP fusion protein, then the LEU2 gene is transcriptionally active, and the cell forms a colony on leu medium (right). FIG. 1B: The pLexA-NP bait plasmid used in the interactive trap. The coding region of influenza A/PR/8/34 virus nucleoprotein (NP) was subcloned into the EcoRl and Sal I restriction sites of pEG202. This construction encodes a fusion protein which includes 202 amino acids of LexA and the entire coding region of NP (498 amino acids) separated by 3 amino acids encoded by polylinker sequences derived from the cloning process (SEQ ID NO:8) and (SEQ ID NO:9).

FIGS. 2A–2H. Nucleotide sequence of NPI-1 cDNA (SEQ ID NO: 10) and deduced protein sequence (SEQ ID NO:11). The coding sequence starts at nucleotide 1 and ends at nucleotide 1581. The 5' terminus of the library clone is indicated by an asterisk. Regions complementary to nested reverse transcription and 5'RACE primers are underlined.

FIGS. 3A and 3B. Comparison of NPI-1 (SEQ ID NO: 11) and SRP1 (SEQ ID NO:12). Vertical lines indicate identity; colons and periods indicate conservative changes (Deveraux et al., 1984, Nucl. Acids Res. 12: 387–395). 42 amino acid ARM repeats are aligned vertically according to Peifer et al., 1994, Cell 76: 789–791. For a complete comparison of SRP1 to other ARM repeat containing proteins, see Peifer et al., 1994, supra. The ARM consensus sequence is indicated at the bottom; "+" indicates K,R, or H; "−" indicates D or E; "~" indicates a gap. Since other residues are conserved within the repeats of NPI-1 and SRP1, a consensus sequence derived from only these two proteins is also shown.

Figure 4:
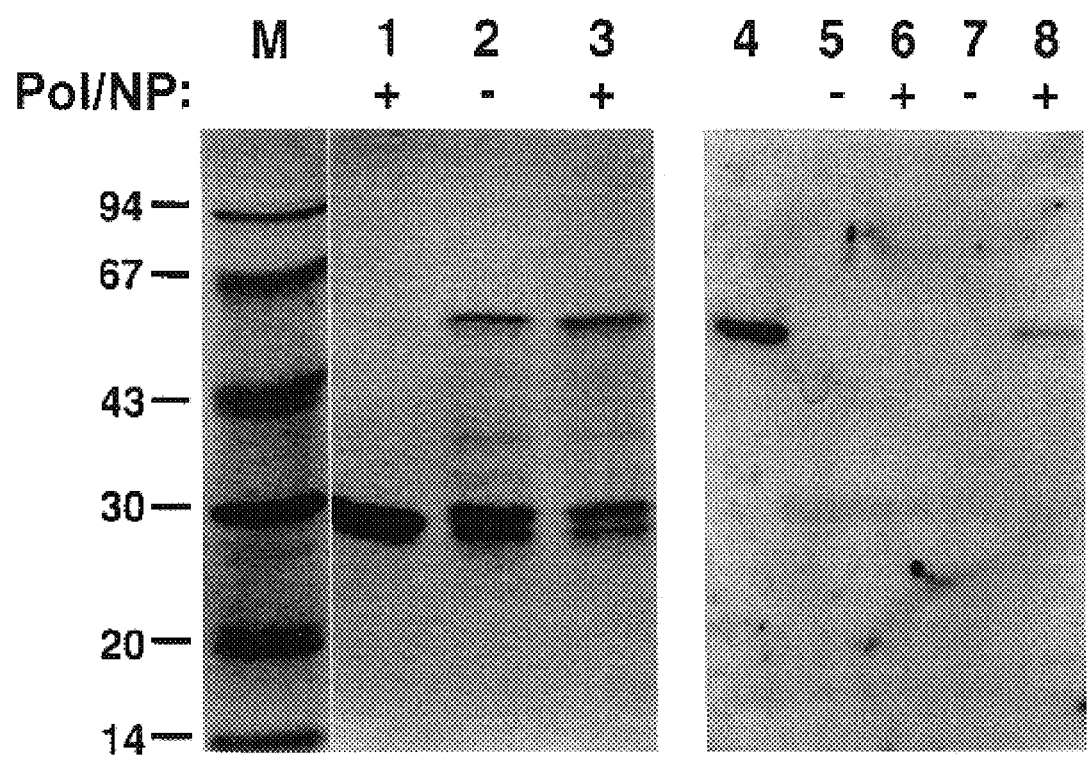

FIG. 4. GST-NPI-1 binds to NP in vitro. GST (lanes 1,5,6) and GST-NPI-1 (lanes 2,3,7,8) were expressed in bacteria and precipitated from cell lysates on glutathione agarose beads. The complexed beads were then incubated with partially purified influenza virus NP and polymerase preparations (Pol/NP) as indicated. Precipitated proteins were fractionated on a 12.5% SDS polyacrylamide gel, and either stained with Coomassie blue (lanes 1 to 3), or immunoblotted using the monoclonal antibody HT103 directed against the viral nucleoprotein (lanes 4 to 8). Unprecipitated Pol/NP was separated in lane 4. M, protein molecular weight markers; *, GST-NPI-1 fusion protein; arrows indicate major fusion protein degradation products.

Figure 5:
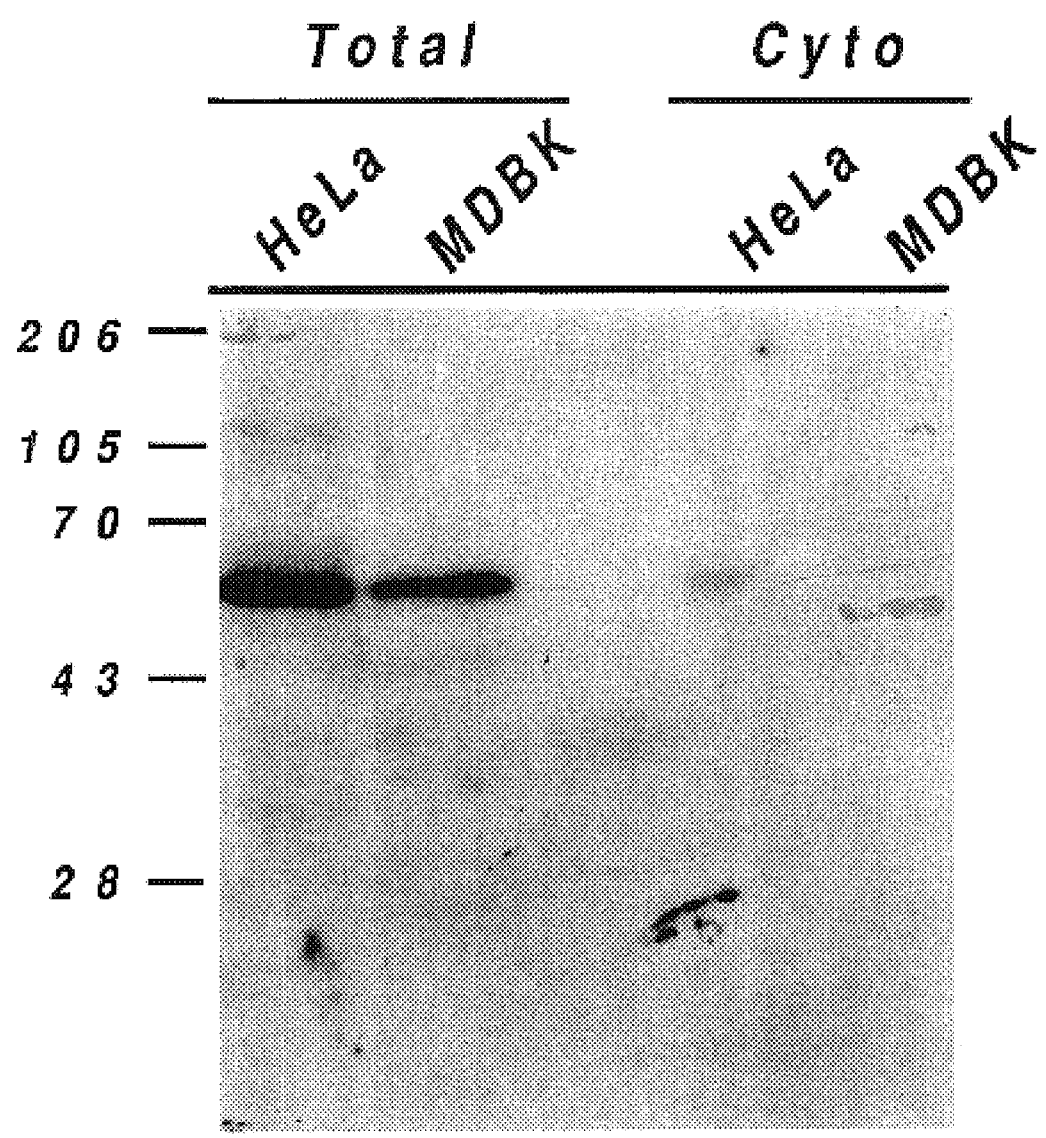

FIG. 5. Immunoblot of total cellular proteins using polyclonal rabbit sera against NPI-1. Total cell lysates and cytoplasmic cell extracts from HeLa and MDBK cell lines were separated by SDS-PAGE, transferred to nitrocellulose, immunoblotted with anti-NPI-1 sera, and developed by $^{125}$I-protein A. Each lane contains protein from 1×10⁵ cells.

Figure 6:
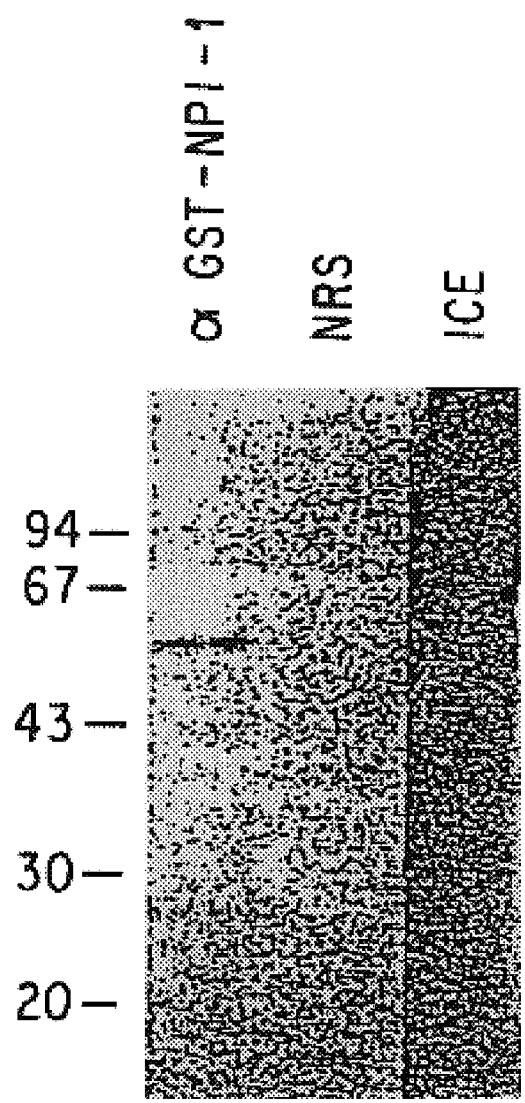

FIG. 6. NP is co-immunoprecipitated from influenza A virus infected cells by antisera against NPI-1. Infected HeLa cell proteins were labeled with $^{35}$S-methionine and $^{35}$S-cysteine, and total cell lysates were made as described in the text. Complexes of NPI-1 and NP were precipitated using anti-NPI-1 sera. Precipitated proteins were then fractionated by SDS-PAGE and detected by autoradiography.

FIGS. 7–11. Partial DNA sequences of isolated coding regions of five different proteins that interact with the NP of influenza A, as detected using the interactive trap system in yeast. The proteins whose sequences are provided are as follows:

FIG. 7: Partial nucleotide sequence of NPI-2 (SEQ ID NO: 13).

FIGS. 8A–8E: Partial nucleotide sequence of NPI-3 (SEQ ID NO: 14) and (SEQ ID NO: 15).

FIG. 9: Partial nucleotide sequence of NPI-4 (SEQ ID NO: 16).

FIG. 10: Partial nucleotide sequence of NPI-5 (SEQ ID NO: 17).

FIG. 11: Partial nucleotide sequence of NPI-6 (SEQ ID NO: 18).

FIGS. 12A–12D: Nucleotide sequence of the NS1I-1 gene (SEQ ID NO: 19) and the encoded amino acid sequence of the NS1I-1 protein (SEQ ID NO: 20). The sequence of 2572 bp was determined by dideoxy sequencing of two overlapping clones. The first clone, pK5, was isolated from the yeast library and contains the HeLa cell cDNA comprising nucleotide positions 791 to 2572. The second clone, pRACENS1I-1, resulted from the 5'RACE procedure used to obtain cDNA derived from the 5'-end of NS1I-1 mRNA, and comprises nucleotide positions 1 to 944.

Figure 13:
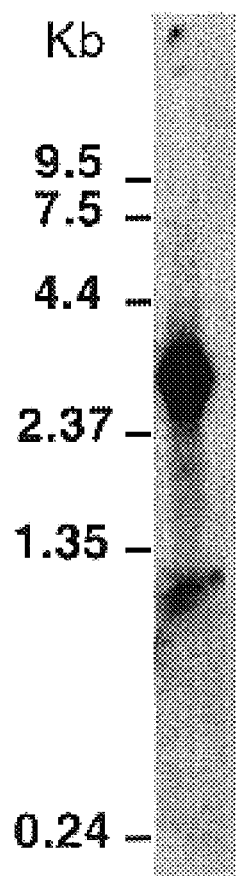

FIG. 13. Northern blot analysis of HeLa cell poly(A)-RNA using an NS1I-1-specific probe.

Figure 14:
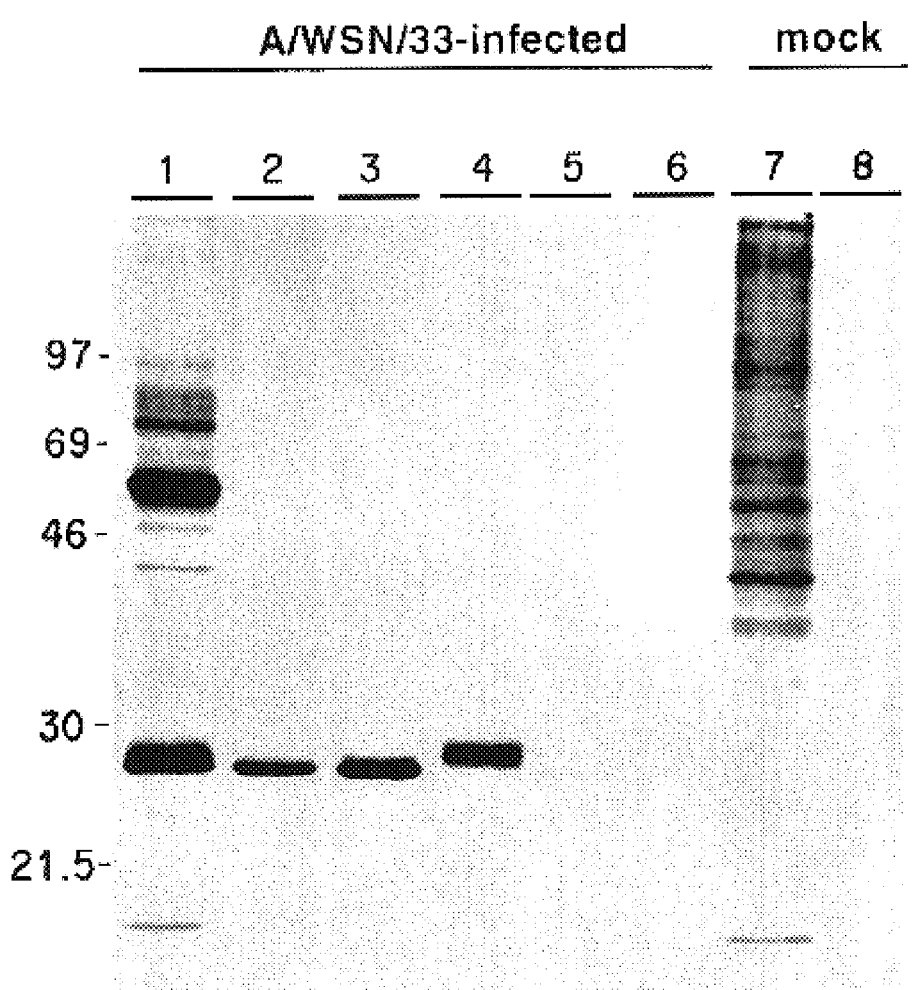

FIG. 14. Co-precipitation of NS1 protein from extracts of A/WSN/33-infected MDCK cells by GST-NS1I-1 and glutathione sepharose. Monolayers of MDCK cells were either infected with influenza A/WSN/33 virus at an m.o.i. of 10 or mock-infected, and labeled with $^{35}$S-methionine and cysteine from 5 to 6 hours p.i. Proteins were extracted and used for binding to glutathione sepharose coated with GST-NS1I-1 (lanes 3 and 8) or GST-protein (lane 6). As controls, extracts were immunoprecipitated with α-NS1 (lane 2), α-M1 (lane 4), or non-immune serum (lane 5). Proteins were analyzed by SDS gel electrophoresis and fluorography. Aliquots of the total extracts corresponding to 10% used for the glutathione agarose precipitations are shown (lanes 1 and 7). The positions of virus proteins and molecular weight markers are indicated to the left.

FIGS. 15A–15E. GST-NS1I-1 co-precipitates NS1 proteins of influenza A and B virus strains. Extracts of $^{35}$S-labeled MDCK cells infected with the influenza viruses A/duck/Alberta/76 (Panel A), A/turkey/Oregon (Panel B), A/Beijing/32/92 (Panel C), A/Berkeley/1/68 (Panel D), and B/Lee/40 (Panel E) were prepared and used in precipitations of viral proteins by glutathione-sepharose coated with GST-NS1I-1 (lanes "GST-K5") or GST-protein (lanes "GST") as described in FIG. 14. In addition, viral proteins were immunoprecipitated using α-NS1-, α-M1- or non-immune serum (lanes "α-NS1", "α-M1", "NI", respectively). Analysis was by SDS gel electrophoresis and fluorography. Aliquots of the total extracts corresponding to 10% (Panels C and E) or 6.7% (Panels A, B, and D), respectively, are also shown (lanes "T"). The positions of viral proteins are indicated to the right.

5. DETAILED DESCRIPTION OF THE INVENTION

The present invention relates to the identification of host cellular proteins that interact with viral proteins important to viral replication and infection; the identification of compounds that interfere with the specific interaction of the host cell and viral proteins; and the evaluation and use of such compounds as antivirals in the treatment of viral infections in animals, including humans.

The invention is described in this section and in the examples, below for the identification and inhibition of interactions between human host cell proteins and influenza viral proteins. For clarity of discussion, particular detail is provided for the isolation of two particular host cell proteins. The first such protein is nucleoprotein interactor 1 (NPI-1), a human cell protein that interacts with the influenza virus NP protein. The NPI-1 gene and protein, and the protein's interaction with NP protein are described in detail in the example in Section 6, below. Other host cell proteins which interact with the NP protein include, but are not limited to, NPI-2, NPI-3, NPI-4, NPI-5, and NPI-6, and are also described, below. Since the interactions between NP and the NPI-1 through NPI-6 host cell proteins have never before been identified, they provide novel targets for antiviral treatment and serve as excellent models for detailing the aspects of the invention. However, the principles may be analogously applied to the identification of other host cell proteins that interact with any of the four influenza virus proteins (PA, PB1, PB2, in addition to NP) required for viral RNA replication.

Particular detail is also provided in the example in Section 7, below, for the identification of nonstructural protein 1 interactor 1 (NS1I-1). NS1I-1 is a human cell protein that interacts with the influenza virus NS1 protein. This interaction also has never before been described, and, therefore, provides yet another novel target for antiviral treatment. The present invention also contemplates identifying interactions between host cell proteins and other viral proteins (in addition to $NS_1$) required for infection, such as, in the case of influenza virus, NS, HA, NA, $M_1$, and $M_2$ proteins.

The principles may also be analogously applied to other RNA viruses, including but not limited to paramyxoviruses, such as parainfluenza viruses, measles viruses, respiratory syncytial virus, bunyviruses, arena viruses, the orthomyxo-like insect virus called Dhori, etc. The host cell proteins so identified may include completely novel proteins, or previously described proteins that have not yet been shown to interact with viral proteins. Any method suitable for detecting protein-protein interactions may be employed for identifying novel viral-host protein interactions, and are considered within the scope of the present invention. For example, some traditional methods are co-immunoprecipitation, crosslinking and copurification through gradients or chromatographic columns. Newer methods result in the simultaneous identification of the genes coding for the protein interacting with a target protein. These methods include probing expression libraries with labeled target protein in a manner similar to antibody probing of Ngtll libraries. One such method which detects protein interactions in vivo, the yeast interactive trap system, was successfully used as described herein to identify the host cell proteins NPI-1 through NPI-6, and NS1I-1, described herein, and is described in detail for illustration only and not by way of limitation.

The host cell/viral protein interactions identified are considered targets for antiviral intervention. Assays, such as the ones described herein, can be used to identify compounds that interfere with such interactions. The compounds so identified which inhibit virus infection, replication, assembly, or release can be used as antivirals. In accordance with the invention, a given compound found to inhibit one virus may be tested for antiviral activity against a wide range of different viruses that have analogous dependencies on host cell proteins, including but not limited to paramyxoviruses, such as parainfluenza viruses, measles viruses, respiratory syncytial virus, bunyviruses, arena viruses, the orthomyxo-like insect virus called Dhori, etc.

Elucidation of the roles of the interacting proteins will lead to identifying other viruses as targets for intervention. For example, we have found that NPI-1 is important to the import of viral nucleic acid-protein complex into the nucleus of the host cell. Therefore, methods described below that disrupt this process, through interfering with the activity of NPI-1, for example, may be effective in treating viruses with nuclear phases, in addition to those viruses listed above. Such additional viruses include, but are not limited to, human immunodeficiency virus (HIV), members of the herpes virus family, and adenoviruses.

The various aspects of the invention are described in the subsections below with specific reference to host cell proteins that interact with NP (NPI-1 through NPI-6) and NS1 (NS1I-1), with particular emphasis on NPI-1; however, the invention is not limited to NPI-1 and encompasses any viral/host cell protein interactions as targets for therapeutic intervention.

5.1. Identification of Host Cell Proteins that Interact with Viral Proteins Required for Replication The previously unidentified gene for the host cell protein NPI-1 was cloned based on its ability to interact with the influenza A virus NP. The NPI-1 is the human homolog of the yeast protein SRP1. Interaction of NPI-1 and NP was demonstrated in yeast by the interactive trap system; in vitro coprecipitation of the NP with a bacterially expressed NPI-1 protein; and in infected cell extracts by coprecipitation of the NP with NPI-1, using anti-NPI-1 sera. The demonstration of this previously unknown interaction is illustrated in the working examples (see Section 6, infra). The data generated indicate that NPI-1 plays a role in the replication of influenza A viruses. NPI-1 is the first cellular protein characterized which interacts with a protein encoded by influenza viruses. This role, therefore, makes the inhibition of the NP-NPI-1 interaction an excellent target for antiviral therapy. It has not yet been demonstrated at what stage in the replication cycle NPI-1 functions. The NPI-1 could affect any of a number of NP functions which may include: (1) movement of the ribonucleoprotein complex (RNP) to the nucleus during viral entry; (2) vRNA synthesis, including antitermination and elongation; (3) mRNA synthesis, including elongation, polyadenylation, and transport to the cytoplasm; and (4) exit of the RNP from the nucleus during virion assembly.

The fact that both NPI-1 and SRP1 interact with proteins involved in RNA synthesis implies that there may be fundamental similarities between cellular DNA-dependent transcription and influenza viral RNA-dependent RNA synthesis. Cellular factors, like NPI-1, may be shared by the viral and the cellular RNA synthesis machinery to perform similar functions. In addition, the NPI-1 may tether the viral RNP to areas of the nuclear matrix where splicing and polyadenylation of mRNA occur. It should be noted that although NPI-1 was isolated from HeLa cells, this cell line is not productively infected by influenza A virus. However, HeLa cells synthesize influenza viral RNAs and proteins (see FIG. 6, lane 3), and have previously been used to examine viral RNA synthesis (Beaton & Krug, 1986, supra).

The viral NP exists in two forms in the infected cell. One form is associated with ribonucleoprotein complexes (RNP), and the other is a free form (Shapiro & Krug, 1988, supra). Pol/NP preparations used in coprecipitation experiments with NPI-1 were purified over cesium chloride/glycerol gradients (Honda et al., 1988, supra), which dissociate and purify virion proteins away from vRNA. The NP but not the polymerase proteins were detected on Coomassie stained gels in this experiment (FIG. 4, lane 3); however, coprecipitation of the viral polymerase proteins was not rigorously tested by immunoblot experiments. Only the NP was coprecipitated from infected HeLa cell extracts (FIG. 6) suggesting that it is free NP which is bound by NPI-1.

Only one host factor has been assigned a definitive function in the replication process of a negative strand RNA virus. The cellular casein kinase II has been shown to phosphorylate the phosphoprotein P of the vesicular stomatitis virus (VSV) RNA-dependent RNA polymerase. This is a step which appears to be required in order to activate the viral polymerase (Barik and Banerjee, 1992, Proc. Natl. Acad. Sci. USA 89: 6570–6574; Barik and Banerjee, 1992, J. Virol. 66: 1109–1118).

NPI-1 and SRP1 are 50% identical and 81% conserved at the amino acid level. This is a very high degree of conservation between proteins belonging to organisms as distantly related as humans and yeast, and suggests that the NPI-1/SRP1 performs a very basic function in the cell. NPI-1 and SRP1 have eight internal repeats, each of approximately 42-amino acids (FIG. 3). This repeat, termed the ARM motif, was originally identified in the Drosophila segment polarity gene armadillo (Riggleman, et al., 1989, Genes Dev. 3: 96–113), and it has been identified in a number of other proteins including β-catenin, plakoglobin, p120, APC and smGDS (Peifer et al., 1994, supra, and references therein). Several ARM proteins are associated with cell adhesion structures. Armadillo and its homologues bind to the C-terminal cytoplasmic tail of cadherins, a calcium-dependent class of cell adhesion molecules(CAMs), linking the CAMs to the underlying cytoskeleton at cell-cell junctions (McCrea, et al., 1991, Science 254: 1359–1361). In contrast to the armadillo protein, SRP1 and NPI-1 appear to be localized to the nucleus. If NPI-1, like SRP1 (Yano, et al., 1992, Mol. Cell. Biol. 12: 5640–5651), is associated with the nuclear membrane, it is possible that NPI-1 functions to tether viral RNP to the nuclear membranes (Jackson, et al., 1982, Nature 296: 366–368). It should be noted that NPI-1 may be related to (or identical with) a nuclear protein that has been found to be involved in V(D)J recombination (Cuomo et al., 1994, Meeting abstract F015, Keystone Symposium on Recombination).

The carboxyl terminal 265 amino acids of the NPI-1, which were sufficient for interaction with the viral NP, contain four and one-half ARM repeats. Individual repeats, in general, are approximately 30% identical with the ARM consensus sequence. This is consistent with the degree of conservation in ARM repeats of other proteins (Peifer et al., 1994, supra).

Using the same interactive trap system in yeast, five additional DNA sequences were isolated which partially encode proteins that interact with the NP of influenza A virus. Also, using this system, a DNA sequence encoding the NS1I-1 protein was identified based the interaction between NS1I-1 and the NS1 protein of influenza A virus. This protein is the human homolog of porcine 17β-estradiol dehydrogenase. Several proteins with a dehydrogenase function have recently been shown to be involved in post-transcriptional events of gene expression (Hentze, 1994, Trends Biochem. Sci. 19: 101–103). This supports an important functional role for the NS1I-1 interaction during the viral life cycle. The various proteins so identified are listed in Table I.

TABLE I

INTERACTING HOST CELL PROTEINS

| Host Cell Proteins | FIG. | Comments |
|---|---|---|
| NPI-1 | FIGS. 2A–2B (SEQ ID NO:13) | New protein sequence, homologous to SRP1 of Yeast |
| NPI-2 | FIG. 7 (SEQ ID NO:13) | Identical to sequences of hnRNP C proteins (Lahiri & Thomas, 1986, Nucl. Acids Res. 14: 4077–4094) |
| NPI-3 | FIGS. 8A–8C (SEQ ID NO:14) | New protein sequence |
| NPI-4 | FIG. 9 (SEQ ID NO:16) | New protein sequence |
| NPI-5 | FIG. 10 (SEQ ID NO: 17) | New protein sequence |
| NPI-6 | FIG. 11 (SEQ ID NO: 18) | New protein sequence |
| NS1I-1 | FIGS. 12A–12B (SEQ ID NO: 19) | New protein sequence, homologous to porcine 17β-estradiol dehydrogenase |

Note Recently performed searches of Genebank have revealed that subsequent to Applicants identification of NPI-3, NPI-4, and NPI-5 these sequences were described by other groups and designated Rch1, PC4, and BAT1, respectively.

The coding sequence for NPI-2 is identical to sequences coding for the previously identified hnRNP C proteins (Lahiri & Thomas, 1986, supra). The NPI-3, NPI-4, NPI-5, and NPI-6 coding sequences were unknown prior their identification by Applicants. The NS1I-1 gene is also novel, as explained in detail in the example in Section 7, below.

The invention contemplates, in addition to the DNA sequences disclosed herein, 1) any DNA sequence that encodes the same amino acid sequence as encoded by the DNA sequences shown in FIGS. 2A–2D, 7, 8A–8C, 9, 10, 11, and 12A–12B; 2) any DNA sequence that hybridizes to the complement of the coding sequences disclosed herein (see FIGS. 2A–2D, 7, 8A–8C, 9, 10, 11, and 12A–12B) under highly stringent conditions, e.g., washing in 0.1×SSC/ 0.1% SDS at 68° C. (Ausubel, F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and/or 3) any DNA sequence that hybridizes to the complement of the coding sequences disclosed herein (see FIGS. 2A–2D, 7, 8A–8C, 9, 10, 11 and 12A–12B) under less stringent conditions, such as moderately stringent conditions, e.g., washing in 0.2×SSC/0.1% SDS at 42° C. (Ausubel, et al., 1989, supra), yet which still encodes a functionally equivalent gene product.

The invention also encompasses 1) DNA vectors that contain any of the coding sequences disclosed herein (see FIGS. 2A–2D, 7, 8A–8C, 9, 10, 11 and 12A–12B), and/or their complements (i.e., antisense); 2) DNA expression vectors that contain any of the coding sequences disclosed herein (see FIGS. 2A–2D, 7, 8A–8C, 9, 10, 11 and 12A–12B), and/or their complements (i.e., antisense), operatively associated with a regulatory element that directs the expression of the coding and/or antisense sequences; and 3) genetically engineered host cells that contain any of the coding sequences disclosed herein (see FIGS. 2A–2D, 7, 8A–8C, 9, 10, 11 and 12A–12B), and/or their complements (i.e., antisense), operatively associated with a regulatory element that directs the expression of the coding and/or antisense sequences in the host cell. Regulatory element includes but is not limited to inducible and non-inducible promoters, enhancers, operators and other elements known to those skilled in the art that drive and regulate expression. The invention includes fragments of any of the DNA sequences disclosed herein.

Once the host cell proteins are obtained, they can be used to detect interactions with proteins from other viruses, in accordance with the invention. The following description is provided to illustrate this approach and not by way of limitation. Influenza B virus ribonucleoprotein complex was isolated and using a Western immunoblot assay, it was found that the cellular NPI-1 was associated with this complex. This result indicates that NPI-1, isolated based on its interaction with influenza A virus NP, also interacts with influenza B virus NP. Thus, compounds that inhibit NP-NPI-1 interactions in influenza A virus and thereby inhibit influenza A viral infection should be similarly effective as antivirals against influenza B virus.

Host cell genes that are homologous to those identified herein may be obtained by several methods. In some cases, different host cell proteins that share the property of interacting with the same viral protein, e.g. influenza A virus NP, may also share genetic homology. Thus, the genes identified through the interactive trap selection may be homologous to one another.

Once a host cell gene is identified in accordance with the invention, any homologous gene may be obtained using cloning methods well known to those skilled in the art, including but not limited to the use of appropriate probes to detect the homologous genes within an appropriate cDNA or gDNA (genomic DNA) library. (See, for example, Sambrook et al., 1989, Molecular Cloning: A Laboratory Manual, Cold Spring Harbor Laboratories, which is incorporated by reference herein in its entirety.) This method is especially useful for obtaining proteins that may not share the property of binding to the same viral protein, but may nonetheless be genetically homologous.

Such homologous proteins may interact with proteins of viruses other than the virus used in the interactive trap. For example, a host cell gene whose product was detected through its interaction with an influenza A viral protein may be homologous to another gene whose product does not interact with influenza A virus, but which does interact with influenza B viral protein. To optimize the detection of such a homologous gene, cDNA libraries may be constructed from cells infected with a virus of interest. Besides influenza B virus, this procedure may be applied analogously to other viruses as well, including but not limited to paramyxoviruses, such as parainfluenza viruses, measles viruses, respiratory syncytial virus, bunyviruses, arena viruses, the orthomyxo-like insect virus called Dhori, as well as human immunodeficiency virus (HIV), members of the herpes virus family, and adenoviruses.

5.2. Screening Assays for Compounds that Interfere with the Interaction of Host Cell and Viral Proteins Required for Viral Replication The host cell protein and the viral protein which interact and bind are sometimes referred to herein as "binding partners". This term also includes peptide fragments, produced as described in the subsections below, comprising the binding domain of each respective protein. Any of a number of assay systems may be utilized to test compounds for their ability to interfere with the interaction of the binding partners. However, rapid high throughput assays for screening large numbers of compounds, including but not limited to ligands (natural or synthetic), peptides, or small organic molecules are preferred. Compounds that are so identified to interfere with the interaction of the binding partners should be further evaluated for antiviral activity in cell based assays, animal model systems and in patients as described herein.

The basic principle of the assay systems used to identify compounds that interfere with the interaction between the viral and host cell proteins involves preparing a reaction mixture containing the viral protein and the host cell protein under conditions and for a time sufficient to allow the two proteins to interact and bind, thus forming a complex. In order to test a compound for inhibitory activity, the reaction is conducted in the presence and absence of the test compound, i.e., the test compound may be initially included in the reaction mixture, or added at a time subsequent to the addition of the viral and host cell protein; controls are incubated without the test compound or with a placebo. The formation of any complexes between the viral protein and the host cell protein is then detected. The formation of a complex in the control reaction, but not in the reaction mixture containing the test compound indicates that the compound interferes with the interaction of the viral protein and host cell protein.

The assay components and various formats that may be utilized are described in the subsections below.

5.2.1. Assay Components

The host cell protein and viral protein binding partners used as components in the assay may be derived from natural sources, e.g., purified from cells and virus, respectively, using protein separation techniques well known in the art; produced by recombinant DNA technology using techniques known in the art (see e.g., Sambrook et al., 1989, Molecular Cloning: A Laboratory Manual, Cold Spring Harbor Laboratories Press, Cold Spring Harbor, N.Y.); and/or chemically synthesized in whole or in part using techniques known in the art; e.g., peptides can be synthesized by solid phase techniques, cleaved from the resin and purified by preparative high performance liquid chromatography (see, e.g., Creighton, 1983, Proteins: Structures and Molecular Principles, W. H. Freeman & Co., N.Y., pp. 50–60). The composition of the synthetic peptides may be confirmed by amino acid analysis or sequencing; e.g., using the Edman degradation procedure (see e.c., Creighton, 1983, supra at pp. 34–49).

The peptide fragments should be produced to correspond to the binding domains of the respective proteins. Any number of methods routinely practiced in the art can be used to identify and isolate the protein's binding site. These methods include but are not limited to mutagenesis of one of the genes encoding the protein and screening for disruption of binding in a co-immunoprecipitation assay, or mutagenesis of the host cell gene and selecting for resistance to viral infection. Compensating mutations in the viral gene can be selected which allow for viral growth in this mutant host. Sequence analysis of the genes encoding the respective proteins will reveal the mutations that correspond to the region of the protein involved in interactive binding. Alternatively, one protein can be anchored to a solid surface using methods described in section 5.2.2. intra, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene for the protein is obtained, short gene segments can be engineered to express peptide fragments of the protein, which can then be tested for binding activity and purified or synthesized.

Whether produced by molecular cloning methods or by chemical synthetic methods, the amino acid sequence of the binding partners which may be used in the assays of the invention need not be identical to the reported sequence of the genes encoding them. The binding partners may comprise altered sequences in which amino acid residues are deleted, added, or substituted resulting in a functionally equivalent product.

For example, functionally equivalent amino acid residues may be substituted for residues within the sequence resulting in a change of sequence. Such substitutes may be selected from other members of the class to which the amino acid belongs; e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic and glutamic acid.

One of the binding partners used in the assay system should be labeled, either directly or indirectly, to facilitate detection of a complex formed between the viral and host cell proteins. Any of a variety of suitable labeling systems may be used including but not limited to radioisotopes such as $^{125}I$; enzyme labelling systems that generate a detectable calorimetric signal or light when exposed to substrate; and fluorescent labels.

Where recombinant DNA technology is used to produce the viral and host cell binding partners of the assay it may be advantageous to engineer fusion proteins that can facilitate labeling, immobilization and/or detection. For example, the coding sequence of the viral or host cell protein can be fused to that of a heterologous protein that has enzyme activity or serves as an enzyme substrate in order to facilitate labeling and detection. The fusion constructs should be designed so that the heterologous component of the fusion product does not interfere with binding of the host cell and viral protein.

Indirect labeling involves the use of a third protein, such as a labeled antibody, which specifically binds to one of the binding partners, i.e., either the host cell protein or viral protein used. Such antibodies include but are not limited to polyclonal, monoclonal, chimeric, single chain, Fab fragments and fragments produced by an Fab expression library.

For the production of antibodies, various host animals may be immunized by injection with the host cell protein or the viral protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72, Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to one of the binding partners.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.2.2. Assay Formats

The assay can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the viral protein and host cell protein. On the other hand, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, one binding partner, e.g., either the viral protein or the host cell protein, is anchored onto a solid surface, and its binding partner, which is not anchored, is labeled, either directly or indirectly. In practice, microtiter plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the host cell and viral protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt the viral protein-host cell protein interaction can be identified.

For example, in a particular embodiment for NPI-1, NPI-1 can be prepared for immobilization using recombinant DNA techniques described in section 5.2.1., supra. Its coding region can be fused to the glutathione-S-transferase (GST) gene using the fusion vector pGEX-5X-1, in such a manner that its binding activity is maintained in the resulting fusion protein. NP can be purified and used to raise a monoclonal antibody, specific for NP, using methods routinely practiced in the art and described above. This antibody can be labeled with the radioactive isotope $^{125}$I, for example, by methods routinely practiced in the art. In a heterogeneous assay, e.a., the GST-NPI-1 fusion protein can be anchored to glutathione-agarose beads. NP can then be added in the presence or absence of the test compound in a manner that allows NP to interact with and bind to the NPI-1 portion of the fusion protein. After the test compound is added, unbound material can be washed away, and the NP-specific labeled monoclonal antibody can be added to the system and allowed to bind to the complexed binding partners. The interaction between NP and NPI-1 can be detected by measuring the amount of radioactivity that remains associated with the glutathione-agarose beads. A successful inhibition of the interaction by the test compound will result in a decrease in measured radioactivity.

Alternatively, the GST-NPI-1 fusion protein and NP can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by measuring the radioactivity associated with the beads.

In another embodiment of the invention, these same techniques can be employed using peptide fragments that correspond to the binding domains of NP and NPI-1, respectively, in place of one or both of the full length proteins. These binding domains can be identified, as described in section 5.2.1., supra. For example, and not by way of limitation, NPI-1 can be anchored to a solid material as described above in this section by making a GST-NPI-1 fusion protein and allowing it to bind to glutathione agarose beads. NP can be labeled with a radioactive isotope, such as $^{35}$S, and cleaved with a proteolytic enzyme such as trypsin. Cleavage products can then be added to the anchored GST-NPI-1 fusion protein and allowed to bind. After washing away unbound peptides, labeled bound material, representing the NP binding domain, can be eluted, purified, and analyzed for amino acid sequence by methods described in section 5.2.1., supra. Peptides so identified can be produced synthetically or fused to appropriate facilitative proteins using recombinant DNA technology, as described in section 5.2.1., supra.

In accordance with the invention, a given compound found to inhibit one virus may be tested for general antiviral activity against a wide range of different viruses that have analogous dependencies on host cell proteins. For example, and not by way of limitation, a compound which inhibits the interaction of influenza virus NP with NPI-1 by binding to the NP binding site can be tested, according to the assays described in section 5.3. infra, against other viruses, particularly those which have similar proteins, e.g., parainfluenza viruses.

5.3. Assays for Antiviral Activity

Any of the inhibitory compounds which are identified in the foregoing assay systems may be tested for antiviral activity.

5.3.1. Viral Growth Assays

The ability of an inhibitor identified in the foregoing assay systems to prevent viral growth can be assayed by plaque formation or by other indices of viral growth, such as the $TCID_{50}$ or growth in the allantois of the chick embryo. In these assays, an appropriate cell line or embryonated eggs are infected with wild-type influenza virus, and the test compound is added to the tissue culture medium either at or after the time of infection. The effect of the test compound is scored by quantitation of viral particle formation as indicated by hemagglutinin (HA) titers measured in the supernatants of infected cells or in the allantoic fluids of infected embryonated eggs; by the presence of viral plaques; or, in cases where a plaque phenotype is not present, by an index such as the $TCID_{50}$ or growth in the allantois of the chick embryo, or with a hemagglutination assay.

An inhibitor can be scored by the ability of a test compound to depress the HA titer or plaque formation, or to reduce the cytopathic effect in virus-infected cells or the allantois of the chick embryo, or by its ability to reduce viral particle formation as measured in a hemagglutination assay.

5.3.2 Animal Model Assays

The ability of an inhibitor to prevent replication of influenza virus can be assayed in animal models that are natural or adapted hosts for influenza. Such animals may include mammals such as pigs, ferrets, mice, monkeys, horses, and primates, or birds. As described in detail in Section 5.5 infra, such animal models can be used to determine the $LD_{50}$ and the $ED_{50}$ in animal subjects, and such data can be used to derive the therapeutic index for the inhibitor of the viral/host cell protein interaction.

5.4. Inhibitory Compounds

Inhibitory compounds identified in the foregoing screening assays which may be used in accordance with the invention may include but are not limited to small organic molecules, peptides and antibodies.

For example, peptides having an amino acid sequence corresponding to the domain of the host cell protein that binds to the viral protein may be used to compete with the native viral protein and, therefore, may be useful as inhibitors in accordance with the invention. Similarly, peptides having an amino acid sequence corresponding to the domain of the viral protein that binds to the host cell protein may be used. Such peptides may be synthesized chemically or produced via recombinant DNA technology using methods well known in the art (e.g., see Creighton, 1983, supra; and Sambrook et al., 1989, supra). Lipofectin or liposomes may be used to deliver the peptides to cells.

Alternatively, antibodies that are both specific for the binding domains of either the host cell or viral proteins and interfere with their interaction may be used. Such antibodies may be generated using standard techniques described in Section 5.2.1., supra, against the proteins themselves or against peptides corresponding to the binding domains of the proteins. Such antibodies include but are not limited to polyclonal, monoclonal, Fab fragments, single chain antibodies, chimeric antibodies, etc. Where whole antibodies are used, internalizing antibodies are preferred. However, lipofectin may be used to deliver the antibody or a fragment of the Fab region which binds to the viral or host cell protein epitope into cells. Where fragments of the antibody are used, the smallest inhibitory fragment which binds to the target protein's binding domain is preferred.

5.5. Pharmaceutical Preparations and Methods of Administration

The identified compounds that inhibit viral replication can be administered to a patient at therapeutically effective doses to treat viral infection. A therapeutically effective dose refers to that amount of the compound sufficient to result in amelioration of symptoms of viral infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of infection in order to minimize damage to uninfected cells and reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal infection, or a half-maximal inhibition) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

6. EXAMPLE

The Identification of NPI-1 and Its Interaction with Influenza Nucleoprotein

The yeast interactive trap system was used to identify a cellular protein which interacts with the nucleoprotein of influenza A viruses. This protein, nucleoprotein interactor 1 (NPI-1) is the human homologue of the yeast protein SRP1. SRP1 was previously identified as a suppressor of temperature-sensitive RNA polymerase I mutations (Yano, et. al., 1992, Mol. Cell. Biol. 12:5640–5651). A full length cDNA clone of NPI-1 was generated from HeLa cell poly A+ RNA. The viral NP, which had been partially purified from influenza A/PR/8/34 virus-infected embryonated eggs, could be coprecipitated from solution by glutathione agarose beads complexed with a bacterially expressed glutathione-S-transferase (GST)-NPI-1 fusion protein, confirming the results of the yeast genetic system. Antisera raised against NPI-1 identified a 65 kDa polypeptide from total cellular extracts of both HeLa and MDBK cells. In addition, the viral nucleoprotein was co-immunoprecipitated from influenza A/WSN/33 virus-infected HeLa cells by antisera directed against NPI-1, demonstrating an interaction of these two proteins in infected cells, and suggesting that NPI-1 plays a role during influenza virus replication.

6.1. Materials and Methods
6.1.1. Yeast, Bacteria and Plasmids

Yeast strain EGY48 (Mata trpl ura3 his3 LEU2::pLEXAop6-LEU2) (Zervos et al., 1993, Cell 72: 222–232) and plasmids pEG202, pSH18-34, and pRFHM1 and the HeLa cell cDNA library constructed in pJG4-5 (Gyuris et al., 1993, Cell 75: 791–803) were previously described. Similar versions of these plasmids and this yeast host strain are available commercially from Clontech as part of a two fusion protein system. pLexA-NP was constructed by subcloning the cDNA of influenza A/PR/8/34 NP as a LexA translational fusion gene into pEG202 (FIG. 1). Yeast strains constructed as part of these studies are described in Table 2. *Escherichia coli* MH3 (trpC araD lacX hsdR galU galK) and W31005 were previously described (Hall et al., 1984, Cell 36: 1057–1065).

6.1.2. Selection of NP Interactors

An interactive trap selection was performed essentially as has been previously described (Gyuris, et al., 1993, supra; Zervos, et al., 1993, supra). Strain R100 was transformed by the HeLa cDNA library using the lithium acetate method (Ito, et al., 1983, J. Bacteriol. 153: 163–168). $2 \times 10^6$ primary yeast transformants were selected on twelve 25×25 cm$^2$ his$^-$ trp$^-$-glucose plates, pooled and stored at $-70°$ C. Library transformants were selected for leu+ phenotype on his$^-$leu$^-$-galactose plates; the efficiency of plating was approximately $10^{-4}$ leu+ colonies per galactose+ colony. Plasmid DNA was isolated from leu+ library transformants as described by Hoffman and Winston (Hoffman & Winston, 1987, Gene 57: 267–272) and introduced into MH3 cells by electroporation. Library plasmids were selected by plating the transformation mix on 1xA+amp+glucose plates (Miller, 1972, Experiments in Molecular Genetics, Cold Spring Harbor Laboratory Press, Cold Spring Harbor, N.Y.).

cDNAs were analyzed by checking the specificity of interaction with the NP. Each isolated plasmid was introduced into strains R101 and R102. These strains harbor pSH18-34, a reporter plasmid encoding β-galactosidase with a GAL1 promoter transcriptionally controlled from upstream LexA binding sites. Strain R102 was used as a negative control for NP-specificity of cloned cDNAs. It contains pRFHM1, which encodes LexA fused to a transcriptionally inert fragment of the *Drosophila melanogaster* bicoid protein. β-Galactosidase activity was assayed on nitrocellulose replicas of the colonies by freeze fracturing the cells and incubating in buffer containing 5-bromo-4-chloro-3-indolyl-β-D-galactoside (X-gal) (Miller, 1972, supra). Plasmids which conferred both a leu+ and β-gal+ phenotypes in the presence of pLexA-NP but not in the presence of pRFHM1 were saved for further study.

6.1.3. Cloning of the 5' Terminus of NPI-1

The 5' terminus of NPI-1 was cloned by rapid amplification of cDNA ends ("RACE") by the method of Frohman (Frohman, 1990, in PCR Protocols: A Guide to Methods and Applications, Innis et. al., eds., Academic Press Inc., San Diego, p. 28–38; Frohman, et al., 1988, Proc. Natl. Acad. Sci. USA 85: 8998–9002). Reverse transcription of 1 µg of poly A+ HeLa cell RNA was performed using the NPI-1 specific oligonucleotide (SEQ ID NO: 1) 5'GCAAAGCAG-GAGAAACCAC3'. First strand cDNA was tailed with dCTP by terminal transferase. PCR amplification of the reverse transcription product was performed with the nested NPI-1 primer (SEQ ID NO: 2) 5'GGGTCCATCTGATA-GATATGAGAG3' and the 5' RACE anchor primer (SEQ ID NO: 3) 5'CUACUACUACUAGGCCACGCGTCGAC-TACTACGGGIIGGGIIGGGIIG3' (Gibco/BRL). The PCR product was subcloned into pGEM-T (Promega) and was sequenced by standard protocols. 5'RACE products from three independant experiments were cloned and sequenced in order to avoid errors introduced by PCR.

6.1.4 Bacterial Expression and Purification of GST-NPI-1

The NPI-1 cDNA derived from a HeLa cDNA library was subcloned into the EcoRl and XhoI restriction endonuclease sites of the glutathione-S-transgerase fusion vector pGEX-5X-1 (Pharmacia) to generate the plasmid pGST-NPI-1. Protein was induced from bacterial expression plasmids in W31005 cells with isopropyl-β-D-galactopyranoside according to standard protocols (Smith & Johnson, 1988, Gene 67: 31–40). Bacteria were pelleted 4 h after induction, washed in ice cold phosphate buffered saline (PBS), and resuspended in one-tenth culture volume PBS+1% Triton X-100. Bacteria were lysed on ice with four 15 s pulses in a Raytheon sonicator at an output setting of 1 amp. Insoluble material was pelleted at 50,000×g for 30 min in a Beckman TL-100.3 rotor.

GST-NPI-1 and GST were purified from bacterial lysates on glutathione-agarose beads (Sigma Chemical Corp.). Beads were swelled according to the manufacturer's instructions and equilibrated in PBS. Typical binding reactions were done in 500 µl of PBS/0.1% Triton X-100, and included 50 µl bacterial lysate and 10 µl of a 50% slurry of glutathione-agarose beads. Binding reactions were incubated for 5 min at room temperature on a rotating wheel. Beads were collected by centrifugation for 5 s in a microfuge, and were washed three times in PBS.

6.1.5. NP Binding Assay

To assay binding of NP to GST-NPI-1/bead complexes typical reactions were performed in 500 µl of ice cold PBS+ 0.05% Nonidet P-40 and contained washed GST-NP1-1/bead complexes and 10 µg partially purified influenza virus polymerase and nucleoprotein preparations (Pol/NP). Virus was prepared from embryonated eggs infected by influenza A/PR/8/34 virus and POL/NP preparations were purified as previously described (Enami, et al., 1990, Proc. Natl. Acad. Sci. USA 87: 3802–3805; Parvin, et al., 1989, J. Virol. 63: 5142–5152). NP was bound for 1 h at 4° C. on a rotating wheel. Beads were collected by centrifugation for 5 s in a microfuge, and were washed three times in PBS+0.05% NP-40. Washed beads were resuspended in 50 µl SDS sample buffer (Sambrook, et al., 1989, Molecular Cloning: A Laboratory Manual, Cold Spring Harbor Laboratories Press, Cold Spring Harbor, N.Y.), boiled for 5 min, and pelleted in a microfuge. 10 µl of each supernatant was separated by electrophoresis on a 12.5% SDS-polyacrylamide gel. Gels were either stained with Coomassie blue or processed for immunoblot analysis. NP was detected by immunoblotting with the monoclonal antibody HT103.

6.1.6. Antisera and Immunoblotting

Polyclonal rabbit antisera against NPI-1 was generated by immunization of a female NZY Rabbit (Buckshire Farms) with 200 µg of purified GST-NPI-1 in complete Freund's adjuvant, followed by two boosts of 100 µg in incomplete Freund's adjuvant at three week intervals. The specificity of antisera was demonstrated by immunoblot analysis of GST-NPI-1 in bacterial lysates. Immunoblots were performed by standard methods (Harlow and Lane, 1998, Antibodies: A Laboratory Manual, Cold Spring Harbor Laboratories Press, Cold Spring Harbor, N.Y.). Sera were used at a dilution of 1:1000.

6.1.7. Viruses and Cells

Total cell lysates from HeLa and MDBK cells were generated by direct lysing of cells in SDS-sample buffer, followed by shearing of chromosomal DNA by passage through a 21 ga. syringe. Cytoplasmic extracts were generated by lysing cells in ice cold NP-40 lysis buffer (10 mM Tris-Cl, pH 8.0; 100 mM NaCl; 1 mM EDTA; 1 mM DTT; 1% Nonidet P-40; 1 mM 4-(2-aminoethyl) benzenesulfonylfluoride-hydrochloride (Pefabloc)). After 10 min on ice nuclei were removed by centrifugation. Proteins were separated by SDS-PAGE, transferred to nitrocellulose and visualized by immunoblotting.

To generate infected cell lysates containing metabolically labeled proteins $4 \times 10^6$ HeLa cells were infected with influenza A/WSN/33 virus at a multiplicity of 10 for 45 min at 37° C. Infection was allowed to proceed in DMEM+0.1% BSA for 5 h at which time cells were labeled with 50 μCi $^{35}$S-methionine+50 μCi $^{35}$S-cystine in MEM-cys-met for 1 h. Extracts were prepared by resuspending infected cells in 650 μl ice cold NP-40 lysis buffer followed by two 15 s pulses in a Raytheon sonicator to disrupt nuclei. Insoluble cell debris was removed by centrifugation at 100,000×g in a TL-100.3 Beckman rotor. 5 μl anti-NPI-1 sera was incubated on ice for 1 h with 100 μl infected cell lysates. Immune complexes were precipitated from solution by incubation with Sepharose-4B linked protein G beads (Sigma) for 1 h. Beads were collected by centrifugation, washed three times in NP-40 lysis buffer, and resuspended in SDS-sample buffer. Precipitated proteins were separated by SDS-PAGE and visualized by autoradiography.

6.2. Results 6.2.1. Isolation of NPI-1

The interactive trap was used to identify proteins which specifically interact with the influenza A virus nucleoprotein (NP). The interactive trap is one of several genetic systems recently developed which uses the modular nature of transcription activators to detect protein:protein interactions (Chien, et al., 1991, Proc. Natl. Acad. Sci. USA 88: 9578–9582; Dalton & Treisman, 1992, Cell 68: 597–612; Durfee, et al., 1993, Genes Dev. 7: 555–569; Gyuris, et al., 1993, supra; Vojtek, et al., 1993, Cell 74: 205–214; Zervos, et al., 1993, supra). The interactive trap consists of three components: (1) a reporter gene that has no basal transcription; (2) a fusion protein which contains a LexA DNA binding domain that is transcriptionally inert; and (3) proteins encoded by an expression library, which are expressed as fusion proteins containing an activation domain (FIG. 1A). Interaction of the LexA fusion protein and the fusion protein containing the activation domain will constitute a bimolecular transcriptional activator which, in this case, will confer the ability to grow on media lacking leucine (Gyuris, et al., 1993, supra; Zervos, et al., 1993, supra). In the absence of this interaction the leu2 gene is not transcribed.

Figure 1B:
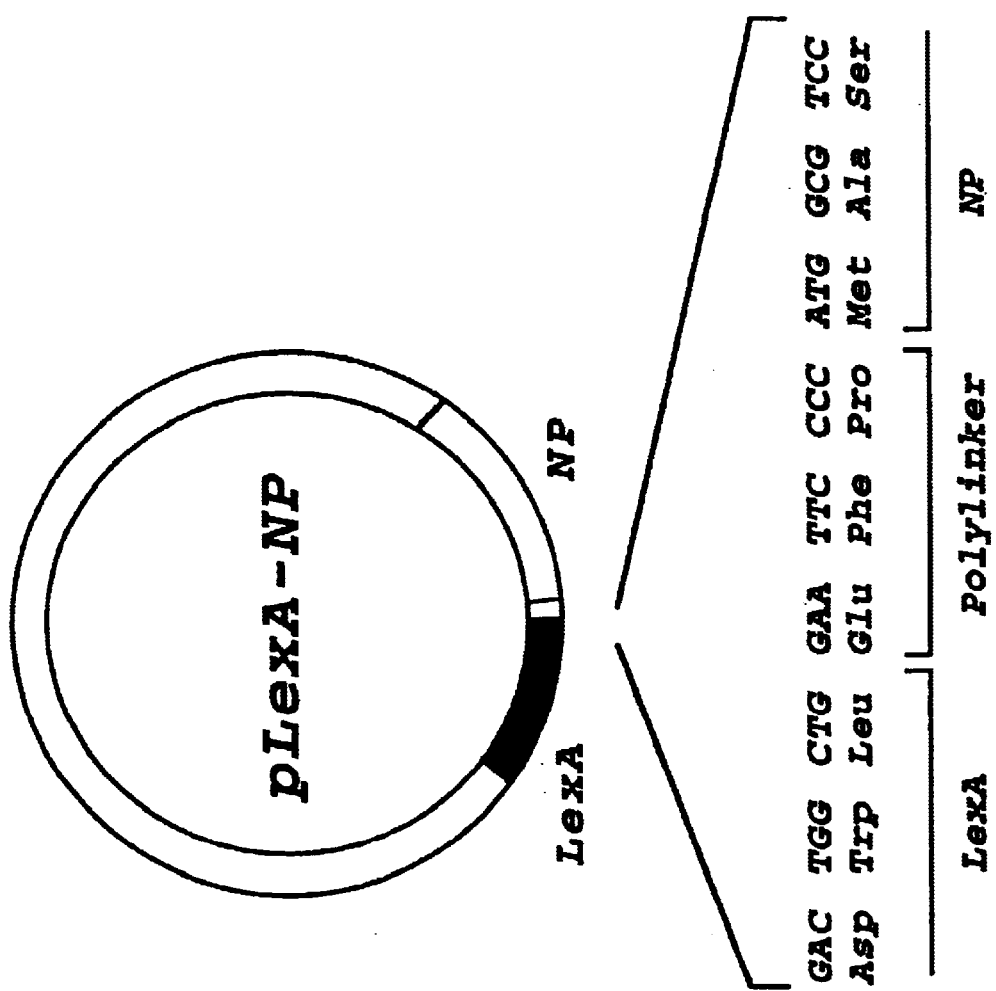

The NP gene of influenza A/PR/8/34 virus was subcloned as a translational fusion gene with the LexA gene into pEG202 to generate pLexA-NP (FIG. 1B). Strain R100 (Table II), which contains pLexA-NP, was transformed with a HeLa cell cDNA library constructed in pJG4-5. pJG4-5 contains an activation domain under control of a GAL1 promoter (Gyuris, et al., 1993, supra).

TABLE II

YEAST STRAINS USED

| Strains | Genotype |
| --- | --- |
| EGY48 | Mata trp1 ura3 his3 LEU2::pLEXAop6-LEU2 |
| R100 | EGY48, pLexA-NP (TRP1) |
| R101 | GY48, pLexA-NP, pSH18-34 (HIS3) |
| R102 | EGY48, pRFHM1 (TRP1), pSH18-34 |

Library plasmids were rescued from 100 leu+ colonies. Reproducibility of the interaction of the NP with the encoded library proteins was tested by transforming library plasmids into strain R101. Transformants were screened for galactose-dependent β-galactosidase activity and growth on media lacking leucine. Specificity for NP was analyzed by checking the ability of library plasmids to confer growth on leu media and β-galactosidase activity in connection with a different LexA fusion plasmid, pRFHM1, encoding a fragment of the *Drosophila melanogaster* bicoid protein. Twenty-three library plasmids were confirmed to encode NP-interactive proteins. Twelve identical 2.1 kbp clones encoded the carboxy terminal fragment of a protein termed nucleoprotein interactor 1 (NPI-1). Partial DNA sequencing showed that NPI-1 is the human homologue of the yeast SRP1 gene (infra).

6.2.2. Cloning and Sequencing of the NPI-1 cDNA

The 2.1 kbp NPI-1 cDNA in pJG4-5 was sequenced by standard protocols. The 5' cDNA terminus of the NPI-1 gene was cloned by 5' RACE. cDNAs from 3 independently derived NPI-1 5'RACE products were cloned and sequenced. Nucleotide and derived amino acid sequences of NPI-1 are shown in FIGS. 2A–2D. The sequence reveals a 2.9 kbp cDNA which encodes a protein of 527 amino acids with a calculated molecular weight of 58,754 Da and a pI=4.74. The carboxyl terminal 265 amino acids were encoded by the interactive trap library plasmid and interact with the viral NP.

Comparison of the deduced amino acid sequences in the GenBank and EMBL data bases using the FASTA and TFASTA programs (Deveraux, et al., 1984, Nucleic Acids Res. 12: 387–395) demonstrated that NPI-1 is the human homologue of the *Saccharomyces cerevisiae* protein SRP1 (Yano, et al., 1992, Mol. and Cell. Biol. 12: 5640–5651). SRP1 was cloned as an allele-specific suppressor of ts mutations in the zinc-binding domain of the A190 subunit of RNA polymerase I. The amino acid sequence is highly conserved between NPI-1 and SRP1: 50% identity and 81% similarity at the amino acid level. The amino terminus of NPI-1 has a potential nuclear localization signal (Chelsky, et al., 1989, Mol. Cell. Biol. 9:2487–2492); amino acids 25 to 49 are rich in arginine, and contain a stretch of four consecutive arginines at amino acids 28 to 31. NPI-1, like SRP1, contains a series of 8 consecutive ARM motifs, which are 42 amino acid protein subsequences originally identified in the Drosophila armadillo protein (Peifer et al., Cell 76: 789–791, 1994; Yano, et al., 1992, supra) (FIG. 3, infra).

6.2.3. NPI-1 Binds to NP In Vitro

In order to demonstrate that the NPI-1 binds to the viral NP, the NPI-1 cDNA fragment (amino acids 262 to 527) was subcloned into the bacterial expression vector pGEX-5X-1 yielding a glutathione S-transferase fusion gene. The expressed fusion protein was purified from bacterial lysates on glutathione agarose beads. NP, which had been partially purified with the viral polymerase from influenza A/PR/8/34 virus was specifically precipitated from solution by glutathione agarose beads complexed with GST-NPI-1 (FIG. 4). The NP band migrates slightly faster than that of the GST-NPI-1 fusion protein. The identity of this protein was confirmed by immunoblot analysis using the anti-NP monoclonal antibody HT103 (FIG. 4, lane 8).

6.2.4. Immunodetection of NPI-1 In Cell Extracts

Rabbit antisera raised against GST-NPI-1 were used to identify a polypeptide from total cellular extracts of both HeLa and MDBK cells with an apparent molecular weight of 65 kDa (FIG. 5). The molecular weight predicted from the derived amino acid sequence of the cDNA is slightly smaller (59 kDa). A lower amount of NPI-1 was present in the cytoplasmic fraction generated by lysis of cells in the presence of NP-40 than in the total cellular extract suggesting that most of NPI-1 is located in the nucleus (FIG. 5). This is consistent with results localizing the NPI-1 homologue SRP1 to the nucleus of yeast cells by immunofluorescence (Yano, et al., 1992, supra). Localization of NPI-1 to a particular intracellular compartment by immunofluorescence experiments has not been posssible due to the high background fluorescence of the antisera preparations used.

6.2.5. NPI-1 Interacts with NP in Infected Cells

Since NP formed a complex with NPI-1 in vitro, we examined whether NP and NPI-1 form a complex in infected cells. NP was specifically coimmunoprecipitated from extracts of influenza A/WSN virus infected HeLa cells by antisera directed against NPI-1 (FIG. 6). This demonstrates an interaction of the viral NP and the cellular NPI-1 during influenza A virus infection.

7. EXAMPLE

The Identification of NS1I-1 and its Interaction with Influenza Nucleoprotein NS1

In the example described below, the yeast interactive trap system was used to identify a human protein, NS1I-1 (NS1-interactor-1), from a HeLa cell cDNA library on the basis of its binding to NS1 of influenza A virus. NS1I-1 is shown herein to be recognized not only by NS1 proteins from five human and avian influenza A strains, but also by NS1 of influenza B virus. Surprisingly, NS1I-1 is homologous to a steroid dehydrogenase isolated from pigs (Leenders, et al., 1994, Eur. J. Biochem. 222: 221–227). Several proteins with a dehydrogenase function have recently been shown not only to have enzymatic activity but also to be involved in post-transcriptional events of gene-expression (Hentze, 1994, supra). This strong conservation supports an important functional role of the NS1I-1 interaction during the viral life cycle.

7.1. Materials and Methods 7.1.1. Yeast, *E.coli* Strains, and Plasmids

Manipulations of nucleic acids, *Escherichia coli* and yeast followed essentially standard procedures as described elsewhere (Ausubel, et al., 1992, Current Protocols in Molecular Biology, Green Publishing Associates, Inc., and John Wiley & sons, Inc., New York). The yeast strains EGY40 (Mata trp1 ura3 his3) and EGY48 (Mata trp1 ura3 his3 LEU2::pLEX-Aop6-LEU2) as well as plasmids pEG202, pRFHM1, and pSH18-34, and the HeLa cell cDNA constructed in pJG4-5 have been described (Gyuris, et al., 1993, supra; Zervos, et al., 1993, supra). *E. coli* strains used for cloning and expression were MH3 (trpC arad lacX hsdR galU galK), DH5α (F $\Phi$80dlacZ$\Delta$M15 $\Delta$(lacZY-argF)U169 deoR recA1 endA1 hsdR17($r_K^-$-$m_K^+$) supE44$\lambda$-thi-gyrA96 relA1), and BL26 (F$^-$ompT hsdS$_B$($r_B^-$m$_B^-$) gal dcm). pLexA-NS1 was constructed by subcloning the cDNA of the NS segment of influenza virus A/PR/8/34 downstream of the LexA gene in pEG202. pGEX-NS1I-1 was constructed by subcloning the HeLa cDNA-insert of library plasmid pK5 as an EcoRI/XboI-fragment into pGEX-5X-1 (Pharmacia). DNA-oligonucleotides used were: GSP-I, (SEQ ID NO: 4) 5'-dTCCTGATGTTGCTGTAGACG-3', GSP-II, (SEQ ID NO: 5) 5'-dGCACGACTAGTATGATTTGC-3', and the 5'RACE anchor primer (SEQ ID NO: 3) (BRL), 5'-dCUACUACUAGGCCACGCGTCGACTAGTACGGGIIGGGIIGGGIIG-3'

7.1.2. Identification of NS1-Interactors

The interactive trap selection was performed essentially as described for NPI-1 in Section 6.1.2, above. The selection strain was constructed by transforming EGY48 with the bait plasmid pLexA-NS1 and the lacZ-reporter plasmid pSH18-34. Expression of lacZ from pSH18-34 is transcriptionally controlled by a GAL1 promoter and LeXA-dependent operator sites. A HeLa cell cDNA library was introduced into the selection strain using the lithium acetate method (Ito, et al., 1983, supra). Primary transformants were selected on trp$^-$his$^-$ura$^-$ glucose plates. 1×10$^6$ cells representing 3.3×10$^5$ independent transformants were plated on 150 mm trp$^-$his$^-$ura$^-$leu$^-$-galactose plates to select for clones expressing NS1-interacting proteins. Viable cells were replica-transferred to a nitrocellulose filter and assayed for β-galactosidase activity using 5-bromo-4-chloro-3-indolyl β-D-galactoside (X-gal) as described (Ausubel et al., 1992, supra). Positive clones were tested in a second round of selection by replica plating onto X-gal trp his ura galactose plates. Plasmid DNA was isolated from yeast clones expressing β-galactosidase activity only on galactose plates and library plasmids were recovered by transformation into *E.coli* MH3 as described in Section 6.1.2, above. The specificity of the isolated plasmids was tested by co-transformation with pLexA-NS1 or pRFHM1 into EGY40 harboring pSH18-34. pRFRM1 expresses an unrelated LexA-bicoid fusion protein. The resulting strains were assayed for β-galactosidase activity on X-gal trp$^-$his$^-$ura$^-$ plates containing glucose or galactose. Plasmids that induced β-galactosidase only in the presence of galactose and only in conjunction with pLexA-NS1 were considered to encode true interacting proteins.

7.1.3. Cloning of NS1I-1 5'-End cDNA

Cloning of cDNA derived from the 5'-end of NS1I-1 mRNA followed a RACE-procedure (rapid amplification of cDNA ends) (Frohmanm, et al., 1988, supra) using a 5'RACE-kit (BRL). First strand cDNA was synthesized from 1 μg of HeLa cell poly(A)-RNA hybridized to 2.5 pmol NS1I-1-specific oligonucleotide GSP-I using reverse transcriptase. The cDNA was tailed at the 5'-end with dC by terminal transferase. The product was used as a template for the amplification of a 5'RACE-product by PCR using a nested oligonucleotide GSP-II and an anchor primer provided by the kit. The resulting fragment was subcloned in pGEM-T (Promega) to form pRACENS1I-1, and sequenced by the standard dideoxy method. The NCBI-search was conducted using Fasta, Tfasta. Sequence comparison was conducted using Bestfit.

7.1.4. Northern Blot Analysis

1 μg of HeLa cell poly(A)-RNA was separated on a 1% agarose-formaldehyde gel, transferred to a nylon membrane (Nytran, Amersham), and UV-crosslinked. The RNA was hybridized to a $^{32}$P-labled, NS1I-1-specific probe derived form a fragment (corresponding to positions +791 to +1745) of the original pK5 library isolate as described (Ausubel, et al., 1992, supra).

7.1.5. Viruses, Cells, and Extracts

Influenza strains A/WSN/33 (H1N1), A/Berkeley/1/68 (H2N2), A/Beijing/32/92 (H3N2), A/duck/Alberta/76 (N12N5), A/turkey/Oregon/71 (H7N5), and B/Lee/40 were grown in the allantoic cavity of 10 days old embryonated chicken eggs. Confluent monolayers of Madin Darby canine kidney-(MDCK)-cells were infected with influenza viruses at an m.o.i. of 10 for one hour in 35 mm dishes. Infection was continued at 37° C. (influenza A viruses) or 35° C. (influenza B/Lee/40) for 5 hours in MEM-medium containing 0.1% bovine serum albumin. Cells were labeled with 100 μCi of $^{35}$S-methionine and $^{35}$S-cysteine (ICN) per dish for one hour in MEM-met$^-$cys$^-$-medium. Cells were washed and scraped in ice-cold phosphate buffered saline (PBS). Cells from one dish were lysed with 500 μl NET-N buffer (10 mm Tris/HCL pH 8.0, 1 mM EDTA, 150 mM Nacl, 0.05% Nonidet P 40) and two 30 second pulses in a Raytheon sonicator at a setting of 1A. Lysates were centrifuged for 10 minutes at 20,000 rpm in a TL100.3 rotor. The supernatants were used for precipitation of proteins.

7.1.6. Expression of GST-NS1I-1 Fusion Protein in *E. coli* and Precipitation of Viral Proteins from Cell Extracts NS1I-1 was expressed in *E. coli* BL26 from pGEX-NS1I-1 as a GST (glutathione-S-transferase)-NS1I-1 fusion protein with a predicted molecular weight of 77 kDa. Production of GST-NS1I-1 was induced using isopropyl-β-D-galactopyranoside essentially as described (Smith, et al., 1988, supra). GST-NS1I-1 was adsorbed from bacterial lysates to glutathione sepharose beads (Pharmacia) as recommended by the manufacturer. Beads were washed three times with PBS to remove contaminating proteins. 10 µl of glutathione sepharose coated with GST-NS1I-1 fusion protein was rotated with 100 µl extract of virus-infected MDCK-cells (see above) in 750 µl NET-100 buffer (20 mM Hepes,pH 8.0, 100 mM NaCl, 0.5 mM DTT) for 90 minutes at 4° C. The beads were washed three times with PBS/0.05% NP-40 and precipitated proteins were analyzed by SDS-gel electrophoresis and autoradiography. In parallel reactions, viral proteins were immunoprecipitated from 50 µl of infected cell extracts using 5 µl of anti-NS1 or anti-M1 antiserum and protein A agarose as described (Harlow & Lane, 1988, supra). As a negative control, GST protein was expressed in BL26 from pGEX-5X-1 and used the same way in the co-precipitation assay.

7.2. Results 7.2.1. Isolation of NS1-Interacting Factors

The yeast interaction trap system (Gyuris, et al., 1993, supra; Zervos, et al., 1993, supra) was used to identify cellular proteins that interact with the non-structural protein NS1 of influenza A virus. A LexA-NS1 fusion protein was used as bait to screen library in which HeLa cell cDNAs were expressed as fusions with an acidic transcription activation domain (Gyuris, 1993 #159). Colonies were selected, in which either of two reporter genes, LEU2 and lacZ, were activated by the cDNA-encoded proteins. This double selection scheme was used to increase the stringency, because in an initial screen a high proportion of candidates scored negative in subsequent genetic tests. The library plasmids were isolated from the selected clones.

The binding specificity of the encoded fusion proteins was tested by assaying the activation of a lacZ-reporter gene encoded on pSH18-34. Expression of β-galactosidase from this plasmid is transcriptionally controlled by LexA-specific operator sites. The isolated library plasmids were co-transformed with pLexA-NS1 or pRFHM1 into EGY40 harboring pSH18-34. pRFHM1 expresses a LexA-bicoid fusion protein and was used as a non-specific operator-binding control. The resulting strains were assayed for β-galactosidase activity specifically on X-gal plates containing galactose, but not glucose. From $3.3 \times 10^5$ independent library transformants, three plasmids were isolated that induced galactose-specific activation of the lacZ reporter gene only in combination with pLexA-NS1. Sequence analysis indicated that the three plasmids were each derived from different cellular cDNAs.

7.2.2. Cloning and Sequence Analysis of NS1I-1

One of the isolated plasmids, pK5, was analyzed further. It carried a cDNA-insert of 1781 bp with an open reading frame of 1413 nucleotides followed by 368 nucleotides of a potentially untranslated region (FIGS. 12A–12B). The cDNA terminated with an oligo(A)-tract and had a consensus poly(A)-site at positions 2526–2531. Northern blot analysis of HeLa cell poly(A)-RNA using a NS1I-1-specific probe detected one single transcript of about 3.0 kb suggesting that the pK5 insert represented an incomplete cDNA (FIG. 13). The remaining NS1I-1 cDNA was cloned by a 5'RACE procedure (Frohman, et al., 1988, supra). Four independent clones were sequenced that differed only in length at the very 5'-end. The longest 5'RACE product, contained in pRACENS1I-1, extended the NS1I-1 sequence for 893 nucleotides upstream totalling in a cDNA of 2674 bp (FIGS. 12A–12B). The sequence has one long open reading frame encoding a protein of 735 amino acids with a predicted molecular mass of 79.5 kDa and a pI of 9.06. The putative ATG-start codon is located 103 nucleotides downstream of the 5'-end and is in the context of a sequence consistent with its being a translational start (Kozak, 1989, J. Cell Biol. 108: 229–241).

Sequence comparisons through the EMBL- and Genbank databases using the FASTA- and TFASTA-analysis programs revealed that NS1I-1 is highly homologous to porcine 17β-estradiol dehydrogenase (Leenders, et al., 1994, supra). The two cDNAs are 86% identical on the nucleic acid level. The encoded proteins are 84% identical and are 92% similar when allowing for conserved amino acid substitutions. NS1I-1 cDNA also shows strong homology to ten human cDNA fragments that have been isolated as expressed sequence tags, as revealed by a BLAST-analysis of the NCBI-database (fragments are between 134 to 556 bp in length). These cDNAs were derived from different tissues including liver, spleen, brain, adipose tissue, and adrenals tissue indicating a broad expression of NS1I-1 in the body.

The encoded NS1I-1 protein features two conserved sequence motifs of the short-chain alcohol dehydrogenase family (Persson, et al., 1991, Eur. J. Biochem. 200: 537–543). Specifically, amino acids 15 to 22 (SEQ ID NO:6) (TGAGAGG) are similar to the potential co-factor binding site, and residues 163 to 167 (SEQ ID NO: 7). (YSAAK) correspond to a short stretch that has been suggested to participate in catalysis (Chen, et al., 1993, Biochemistry 32: 3342–3346). The presence of the tri-peptide AKL at the carboxy-terminus was also noted. Similar tri-peptide motifs have been found to serve as targeting signals for import into microbodies (for a review, see de Hoop & Ab, 1992, Biochem. J. 286: 657–669). However, the presence of this signal does not automatically direct a protein to these organelles (de Hoop & Ab, 1992, supra).

7.2.3. NS1I-1 Binds NS1 Protein from Extracts of Influenza Virus Infected Cells

In order to confirm a physical interaction between NS1I-1 protein and NS1 expressed in influenza virus infected cells, a co-precipitation assay was performed as similarly described in Section 6.2.3, above, for NPI-1. A glutathione-S-transferase(GST)-NS1I-1 fusion gene was constructed and expressed in *E.coli*. GST-NS1I-1 fusion protein from bacterial lysate was absorbed to the affinity matrix glutathione agarose and purified from contaminating bacterial proteins. The immobilized fusion protein was used to bind and precipitate $^{35}$S-labeled proteins from extracts of MDCK cells infected with human influenza A/WSN/33 viruses (FIG. 14). The NS1 protein of this strain is 98% identical to its counterpart from A/PR/8/34 used in the yeast interaction screen. Aliquots of the same extract were used to in parallel reactions to immunoprecipitate influenza virus proteins NS1 and M1. The precipitated proteins were analyzed by SDS-gel electrophoresis and visualized by fluorography. FIG. 14 shows, that GST-NS1I-1 efficiently precipitated a protein band co-migrating with immunoprecipitated NS1 protein from infected cell extract (compare lanes 2 and 3). This interaction was specific for NS1I-1 since no proteins were detected in precipitates using GST only (lane 6). In addition, no proteins were precipitated by GST-NS1I-1 from mock-infected cells (lane 8), showing that a virus induced protein was recognized by NS1I-1. This experiment confirmed, that NS1I-I interacts specifically with the NS1 protein of influenza A virus.

If this interaction is important for the viral life-cycle one would expect it to be conserved. Consequently, the binding of NS1I-1 to NS1 proteins from other influenza A strains should be detectable despite of their considerable variation in the primary structure (Baez, et al., 1981, Virology 113: 397–402; Ludwig, et al., 1991, Virology 183: 566–577). Therefore the interaction between NS1I-1 and NS1 was examined using the same co-precipitation assay described above, with extracts front cells infected with different influenza A and B virus strains.

Figure 15A:
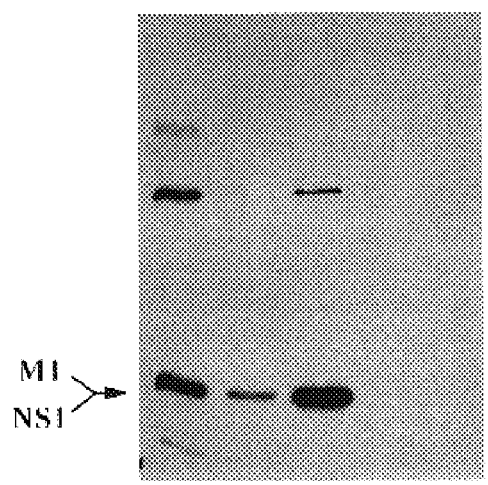
Figure 15B:
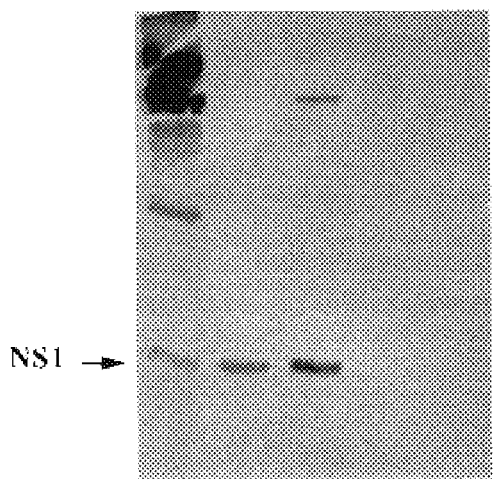
Figure 15C:
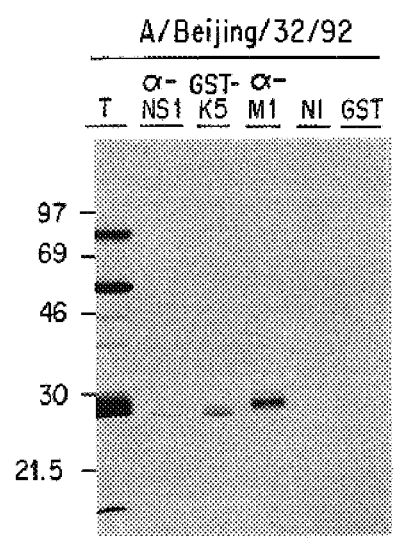
Figure 15D:
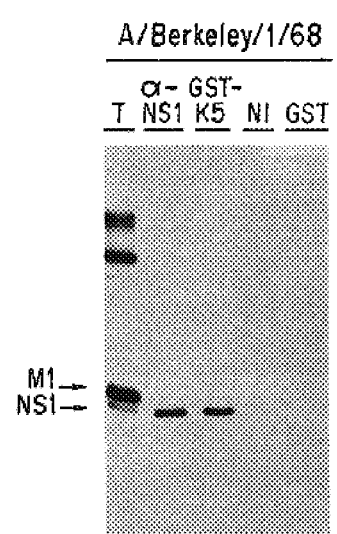
Figure 15E:
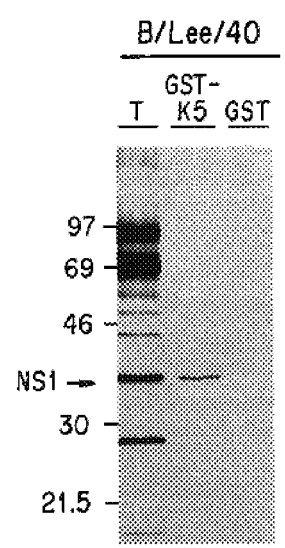

Mutations accumulate in the NS1 gene at a steady rate over time (Buonagurio, et al., 1985, Science 232: 980–982). Thus, the time-span between the isolation of two strains is reflected in the sequence variation of its NS1 proteins (Ludwig, et al., 1991, supra; Buonagurio, et al., 1985, supra). NS1I-1 binding to NS1 proteins from two recently isolated human influenza A strains A/Beijing/32/92 and A/Berkeley/1/68 was examined. As can be seen in FIG. 15B, Panels C and D, respectively; NS1 proteins from both strains were specifically precipitated (FIG. 15B, Panels C and D, lanes "GST-K5"). A low immunoprecipitation efficiency of NS1 protein from the Beijing-strain (Panel C) was reproducibly observed. The NS1 proteins of A/Berkeley/1/68 and A/WSN/33 are 90.8% identical to each other. The NS1 sequence of A/Beijing/32/92 is not known.

The following analyses were conducted to examine whether GST-NS1I-1 is also recognized by the more divergent NS1 proteins of the avian influenza strains A/duck/Alberta/76 and A/turkey/Oregon/71. The NS1 proteins of these strains are 66.5% and 63.6% identical, respectively, to A/WSN/33. Significantly, NS1 of A/turkey/Oregon/71 is only 124 amino acids in length, lacking most of the carboxy-terminal half of other NS1 proteins, which consist of 207 to 237 amino acids (Norton, et al., 1987, Virology 156: 204–213). Nevertheless, precipitation of a protein band co-migrating with NS1 from both strains was observed (FIG. 15A, Panels A and B, lanes "GST-K5"). The NS1 and M1 proteins of A/duck/Alberta/76 could not be separated by the gel system used. Significant amounts of nucleoprotein in the GST-NS1I-1 precipitates of these avian strains were reproducibly detected for undetermined reasons.

Finally, the co-precipitation assay was used to test the human influenza B virus B/Lee/40. Surprisingly, GST-NS1I-1 precipitated specifically the influenza B virus NS1 protein, although it is only 20.6% identical to NS1 from A/WSN/33 (FIG. 15B, Panel E, lane "GST-K5"). Taken together, the binding of GST-NS1I-1 to NS1 proteins expressed by several influenza A and B virus stains could be demonstrated, despite the great divergence of their primary structures. This result strongly supports an important function of this interaction during the viral life cycle, and indicates that the NS1I-1 interaction is an excellent target for antiviral intervention.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An assay for identifying a substance that inhibits the interaction of an influenza virus nucleoprotein with a host cell protein comprising:

(a) contacting an influenza virus nucleoprotein with a host cell protein, under conditions and for a time sufficient to permit the influenza virus nucleoprotein to bind to and form a complex with the host cell protein, in the presence of a test substance, wherein the host cell protein is nucleoprotein interactor (NPI)-1, NPI-2, NPI-3, NPI-4, NPI-5 or NPI-6; and (b) detecting the formation of a complex, wherein a decrease in the complex detected as compared to the amount of complex detected in the absence of the substance indicates that a substance that inhibits the interaction between the influenza virus nucleoprotein and the host cell protein.

2. The assay of claim 1 in which the host cell protein is NPI-1.

3. The assay of claim 2 in which the host cell protein is NPI-2.

4. The assay of claim 2 in which the host cell protein is NPI-3.

5. The assay of claim 2 in which the host cell protein is NPI-4.

6. The assay of claim 2 in which the host cell protein is NPI-5.

7. The assay of claim 2 in which the host cell protein is NPI-6.

8. The assay of claim 1 in which the influenza virus nucleoprotein is immobilized.

9. The assay of claim 8 in which an immobilized antibody is used to anchor the immobilized influenza virus nucleoprotein.

10. The assay of claim 8 in which the influenza virus nucleoprotein is immobilized prior to the reaction so that the reaction is conducted in a solid-liquid phase.

11. The assay of claim 1 in which the proteins are contacted in a liquid phase to form a complex which is separated from the liquid phase at the end of the reaction.

12. The assay of claim 11, in which the complex formed is separated from the liquid phase by immobilizing the complex on a solid phase.

13. The assay of claim 12 in which the complex is captured by an immobilized antibody specific for one of the proteins binding partners.

14. An assay for identifying a substance that inhibits the interaction of an influenza virus nucleoprotein with NPI-1 comprising:

(a) contacting an influenza virus nucleoprotein with a peptide fragment of NPI-1, under conditions and for a time sufficient to permit the influenza virus nucleoprotein to bind to and form a complex with the peptide fragment NPI-1, in the presence of a substance, wherein the peptide fragment of NPI-1 consists of amino acid residues 262 to 527 of NPI-1 influenza virus; and (b) detecting the formation of a complex, wherein a decrease in the complex detected as compared to the amount of complex detected in the absence of the substance indicates that a substance that inhibits the interaction between the influenza virus nucleoprotein and the NPI-1 is identified.

15. An assay for identifying a substance that inhibits the interaction of an influenza virus nucleoprotein with NPI-1 comprising:

(a) contacting a fusion protein with influenza virus nucleoprotein, under conditions and for a time sufficient to permit the fusion protein to bind to and form a complex with the influenza virus nucleoprotein, in the presence of a substance, wherein the fusion protein comprises NPI-1 or amino acid residues 262 to 527 of NPI-1; and (b) detecting the formation of a complex, wherein a decrease in the complex detected as compared to the amount of complex detected in the absence of the substance indicates that a substance that inhibits the interaction between the influenza virus nucleoprotein and the NPI-1 is identified.

16. The assay of claim 1 in which the host cell protein is immobilized on a solid surface.

17. The assay of claim 16 in which an immobilized antibody is used to anchor the immobilized host cell protein.

18. The assay of claim 16 in which the host cell protein is immobilized prior to the reaction so that the reaction is conducted in a solid-liquid phase.

19. The assay of claim 14 in which the peptide fragment NPI-1 is immobilized on a solid surface.

20. The assay of claim 15 in which the influenza virus nucleoprotein is immobilized on a solid surface.

21. The assay of claim 1 or 8 in which the host cell protein is directly or indirectly labeled.

22. The assay of claim 1 or 16 in which the influenza virus nucleoprotein is directly or indirectly labeled.

23. The assay of claim 14 in which the peptide fragment is directly or indirectly labeled.

24. The assay of claim 15 in which the influenza virus nucleoprotein is directly or indirectly labeled.

25. The assay of claim 15 or 20 in which the fusion protein is directly or indirectly labeled.

26. The assay of claim 15 or 24 in which the fusion protein is immobilized on a solid surface.

27. The assay of claim 21, wherein the label is a radioisotope, an enzymatic label or a fluorescent label.

28. The assay of claim 22, wherein the label is a radioisotope, an enzymatic label or a fluorescent label.

29. The assay of claim 23 or 24, wherein the label is a radioisotope, an enzymatic label or a fluorescent label.

30. The assay of claim 25, wherein the label is a radioisotope, an enzymatic label or a fluorescent label.

31. The assay of claim 1, 14 or 15, wherein the test substance is a peptide, antibody, or small organic molecule.

* * * * *

UNITED STATES PATENT AND TRADEMARK OFFICE
CERTIFICATE OF CORRECTION

| | | Page 1 of 1 |
|---|---|---|
| PATENT NO. | : 6,890,710 B1 | |
| APPLICATION NO. | : 08/444994 | |
| DATED | : May 10, 2005 | |
| INVENTOR(S) | : Palese et al. | |

It is certified that error appears in the above-identified patent and that said Letters Patent is hereby corrected as shown below:

At column 1, line 11 of the patent, please insert the following:

--STATEMENT REGARDING FEDERALLY SPONSORED
RESEARCH OR DEVELOPMENT

This invention was made with government support under grant No. AI011823 awarded by the National Institutes of Health. The government has certain rights in the invention.--

Signed and Sealed this
Nineteenth Day of April, 2011

David J. Kappos
*Director of the United States Patent and Trademark Office*